United States Patent
Kumar et al.

(10) Patent No.: US 8,008,423 B2
(45) Date of Patent: Aug. 30, 2011

(54) STABILIZED POLYOLEFIN COMPOSITIONS

(75) Inventors: Vijayendra Kumar, Dracut, MA (US);
Rajesh Kumar, Groton, CT (US);
Ashish Dhawan, Lowell, MA (US);
Sui-Zhou Yang, Dracut, MA (US);
Ashok L. Cholli, Chelmsford, MA (US)

(73) Assignee: Polnox Corporation, Lowell, MA (US)

(*) Notice: Subject to any disclaimer, the term of this patent is extended or adjusted under 35 U.S.C. 154(b) by 0 days.

(21) Appl. No.: 12/789,832

(22) Filed: May 28, 2010

(65) Prior Publication Data

US 2010/0305251 A1     Dec. 2, 2010

Related U.S. Application Data

(63) Continuation of application No. 11/293,844, filed on Dec. 2, 2005, now Pat. No. 7,902,317.

(60) Provisional application No. 60/633,196, filed on Dec. 3, 2004.

(51) Int. Cl.
*C08G 63/00*     (2006.01)
*C08G 64/00*     (2006.01)

(52) U.S. Cl. .......... 528/183; 528/86; 562/357; 562/442

(58) Field of Classification Search .................. 528/86, 528/183; 562/357, 442
See application file for complete search history.

(56) References Cited

U.S. PATENT DOCUMENTS

| | | |
|---|---|---|
| 3,116,305 A | 12/1963 | Morris et al. |
| 3,294,836 A | 12/1966 | Peterson et al. |
| 3,441,545 A | 4/1969 | Blatz et al. |
| 3,459,704 A | 8/1969 | Peterson et al. |
| 3,557,245 A | 1/1971 | Phillips et al. |
| 3,632,785 A | 1/1972 | Bornstein |
| 3,645,970 A | 2/1972 | Kleiner |
| 3,649,667 A | 3/1972 | Song et al. |
| 3,655,831 A | 4/1972 | Friedman |
| 3,870,680 A | 3/1975 | Schurdak |
| 3,907,939 A | 9/1975 | Robin et al. |
| 3,953,402 A | 4/1976 | Kline |
| 3,965,039 A | 6/1976 | Chaplits et al. |
| 3,983,091 A | 9/1976 | Gloth et al. |
| 3,994,828 A | 11/1976 | Zaffaroni |
| 3,996,160 A | 12/1976 | Dale et al. |
| 3,996,198 A | 12/1976 | Wang et al. |
| 4,054,676 A | 10/1977 | Weinshenker et al. |
| 4,094,857 A | 6/1978 | Wolfe, Jr. |
| 4,096,319 A | 6/1978 | Willette et al. |
| 4,097,464 A | 6/1978 | Kline |
| 4,098,829 A | 7/1978 | Weinshenker et al. |
| 4,107,144 A | 8/1978 | Russell et al. |
| 4,136,055 A | 1/1979 | Lyons |
| 4,202,816 A | 5/1980 | Moser et al. |
| 4,205,151 A | 5/1980 | Dale et al. |
| 4,213,892 A | 7/1980 | Scott |
| 4,219,453 A | 8/1980 | Sakurai et al. |
| 4,267,358 A | 5/1981 | Hechenbleikner et al. |
| 4,281,192 A | 7/1981 | Jacquet et al. |
| 4,283,572 A | 8/1981 | Klicker |
| 4,317,933 A | 3/1982 | Parker |
| 4,341,879 A | 7/1982 | Sugio et al. |
| 4,355,148 A | 10/1982 | Layer et al. |
| 4,377,666 A | 3/1983 | Farrar |
| 4,380,554 A | 4/1983 | Serres, Jr. |
| 4,447,657 A | 5/1984 | Firth et al. |
| 4,465,871 A | 8/1984 | Firth et al. |
| 4,510,296 A | 4/1985 | Hergenrother |
| 4,511,491 A | 4/1985 | Ishii et al. |
| 4,634,728 A | 1/1987 | Dunski et al. |
| 4,690,995 A | 9/1987 | Keskey et al. |
| 4,761,247 A | 8/1988 | Rei et al. |
| 4,824,929 A | 4/1989 | Arimatsu et al. |
| 4,849,503 A | 7/1989 | Cotter et al. |
| 4,855,345 A | 8/1989 | Rosenberger et al. |
| 4,857,596 A | 8/1989 | MacLeay et al. |
| 4,870,214 A | 9/1989 | Mina et al. |
| 4,894,263 A | 1/1990 | Dubois et al. |
| 4,897,438 A | 1/1990 | Kikuchi et al. |
| 4,900,671 A | 2/1990 | Pokora et al. |
| 4,925,591 A | 5/1990 | Nakauchi et al. |
| 4,968,759 A | 11/1990 | Kikuchi et al. |
| 4,977,004 A | 12/1990 | Bettle, III et al. |
| 4,981,917 A | 1/1991 | MacLeay et al. |
| 4,994,628 A | 2/1991 | Goddard et al. |
| 5,013,470 A | 5/1991 | Benfaremo |
| 5,017,727 A | 5/1991 | Olivier |
| 5,082,358 A | 1/1992 | Tabata et al. |

(Continued)

FOREIGN PATENT DOCUMENTS

CS     111291     6/1964

(Continued)

OTHER PUBLICATIONS

Akkara, J.A., et al., "Hematin-Catalyzed Polymerization of Phenol Compounds," Macromolecules, 33(7):2377-2382 (2000).

Akkara, J.A., et al., "Synthesis and Characterization of Polymers Produced by Horseradish Peroxidase in Dioxane," J. of Polymer Science: Part A: Polymer Chemistry, 29(11):1561-1574 (1991).

Armengol, E., et al., "Acid Zeolites as Catalysts in Organic Reactions, tert-Butylation of Anthracene, Naphthalene and Thianthrene," Appl. Catal. A 149:411-423 (1997).

Ayyagari, M.S., et al., "Controlled Free-Radical Polymerization of Phenol Derivatives by Enzyme-Catalyzed Reactions in Organic Solvents," Macromolecules, 28(15):5192-5197 (1995).

Badamali, S.K., et al., "Influence of Aluminium Sources on the Synthesis and Catalytic Activity of Mesoporous AlMCM-41 Molecular Sieves," Catal. Today 63:291-295 (2000).

(Continued)

*Primary Examiner* — Terressa M Boykin
(74) *Attorney, Agent, or Firm* — Hamilton, Brook, Smith & Reynolds, P.C.

(57) ABSTRACT

Disclosed are compositions comprising antioxidants and stabilizers, such as, acid scavengers or organic phosphorus stabilizers, and optionally further comprising co-stabilizers. The disclosed compositions are useful as stabilizers for polyolefins and other polymeric materials. The disclosed compositions and methods generally provide longer shelf lifes and better oxidative resistance to materials than currently available antioxidants.

21 Claims, 2 Drawing Sheets

U.S. PATENT DOCUMENTS

| | | | |
|---|---|---|---|
| 5,102,962 A | 4/1992 | Kikuchi et al. |
| 5,117,063 A | 5/1992 | Stern et al. |
| 5,143,828 A | 9/1992 | Akkara et al. |
| 5,155,153 A | 10/1992 | Neri et al. |
| 5,185,391 A | 2/1993 | Stokich, Jr. |
| 5,185,407 A | 2/1993 | Wong |
| 5,188,953 A | 2/1993 | Johnson et al. |
| 5,191,008 A | 3/1993 | Frost et al. |
| 5,196,142 A | 3/1993 | Mollet et al. |
| 5,206,303 A | 4/1993 | Tse et al. |
| 5,207,939 A | 5/1993 | Farng et al. |
| 5,274,060 A | 12/1993 | Schadeli |
| 5,278,055 A | 1/1994 | Cyrus, Jr. et al. |
| 5,304,589 A | 4/1994 | Davidson et al. |
| 5,320,889 A | 6/1994 | Bettle, III |
| 5,449,715 A | 9/1995 | Plochocka et al. |
| 5,498,809 A | 3/1996 | Emert et al. |
| RE35,247 E | 5/1996 | Cyrus, Jr. et al. |
| 5,516,856 A | 5/1996 | Sanchez |
| 5,541,091 A | 7/1996 | Wheeler et al. |
| 5,565,300 A | 10/1996 | Uenishi et al. |
| 5,574,118 A | 11/1996 | Olivier |
| 5,652,201 A | 7/1997 | Papay et al. |
| 5,739,341 A | 4/1998 | Dubs et al. |
| 5,834,544 A | 11/1998 | Lin et al. |
| 5,837,798 A | 11/1998 | Hutchings et al. |
| 5,869,592 A | 2/1999 | Gagne et al. |
| 5,911,937 A | 6/1999 | Hekal |
| 5,994,498 A | 11/1999 | Tripathy et al. |
| 6,018,018 A | 1/2000 | Samuelson et al. |
| 6,046,263 A | 4/2000 | Rasberger et al. |
| 6,096,695 A | 8/2000 | Lam et al. |
| 6,096,859 A | 8/2000 | Akkara et al. |
| 6,150,491 A | 11/2000 | Akkara |
| 6,232,314 B1 | 5/2001 | Jarrott et al. |
| 6,342,549 B1 | 1/2002 | Hirose et al. |
| 6,444,450 B2 | 9/2002 | Akkara et al. |
| 6,646,035 B2 | 11/2003 | Koch et al. |
| 6,723,815 B2 | 4/2004 | Callaghan et al. |
| 6,743,525 B2 | 6/2004 | Berntsen et al. |
| 6,770,785 B1 | 8/2004 | Desai et al. |
| 6,794,480 B2 | 9/2004 | Goto et al. |
| 6,800,228 B1 | 10/2004 | Semen |
| 6,828,364 B2 | 12/2004 | Gugumus |
| 7,132,496 B2 | 11/2006 | Kerres et al. |
| 7,169,844 B2 | 1/2007 | Inokami |
| 7,205,350 B2 | 4/2007 | Thibaut |
| 7,223,432 B2 | 5/2007 | Cholli et al. |
| 7,262,319 B2 | 8/2007 | Rehm et al. |
| 7,705,176 B2 | 4/2010 | Cholli et al. |
| 2001/0041203 A1 | 11/2001 | Uno et al. |
| 2002/0007020 A1 | 1/2002 | Higashimura et al. |
| 2002/0128493 A1 | 9/2002 | Romanczyk, Jr. et al. |
| 2002/0143025 A1 | 10/2002 | Pratt et al. |
| 2002/0183470 A1 | 12/2002 | Tripathy et al. |
| 2003/0030033 A1 | 2/2003 | Duyck et al. |
| 2003/0078346 A1 | 4/2003 | Nakamura et al. |
| 2003/0091837 A1 | 5/2003 | Aoki |
| 2003/0176620 A1 | 9/2003 | Romanczyk, Jr. et al. |
| 2003/0191242 A1 | 10/2003 | Zedda et al. |
| 2003/0229196 A1 | 12/2003 | Braat et al. |
| 2003/0230743 A1 | 12/2003 | Cholli et al. |
| 2004/0015021 A1 | 1/2004 | Adams et al. |
| 2004/0164279 A1 | 8/2004 | Stevenson et al. |
| 2004/0180994 A1 | 9/2004 | Pearson et al. |
| 2004/0186167 A1 | 9/2004 | Dou et al. |
| 2004/0186214 A1 | 9/2004 | Li et al. |
| 2004/0198875 A1 | 10/2004 | Kaprinidis et al. |
| 2004/0214935 A1 | 10/2004 | Cholli et al. |
| 2005/0170978 A1 | 8/2005 | Migdal et al. |
| 2005/0209379 A1 | 9/2005 | Botkin et al. |
| 2005/0238789 A1 | 10/2005 | Cholli et al. |
| 2005/0242328 A1 | 11/2005 | Baranski |
| 2006/0029706 A1 | 2/2006 | Cholli et al. |
| 2006/0040833 A1 | 2/2006 | Al-Akhdar et al. |
| 2006/0041087 A1 | 2/2006 | Cholli |
| 2006/0041094 A1 | 2/2006 | Cholli |
| 2006/0128929 A1 | 6/2006 | Yang et al. |
| 2006/0128930 A1 | 6/2006 | Dhawan et al. |
| 2006/0128931 A1* | 6/2006 | Kumar et al. ................. 528/183 |
| 2006/0128939 A1 | 6/2006 | Kumar et al. |
| 2006/0154818 A1 | 7/2006 | Destro et al. |
| 2006/0189820 A1 | 8/2006 | Rehm et al. |
| 2006/0189824 A1 | 8/2006 | Kumar et al. |
| 2006/0208227 A1 | 9/2006 | Shiraki |
| 2006/0233741 A1 | 10/2006 | Kumar et al. |
| 2007/0010632 A1 | 1/2007 | Kaplan et al. |
| 2007/0106059 A1 | 5/2007 | Cholli et al. |
| 2007/0135539 A1 | 6/2007 | Cholli et al. |
| 2007/0149660 A1 | 6/2007 | Kumar et al. |
| 2007/0154430 A1 | 7/2007 | Cholli et al. |
| 2007/0154608 A1 | 7/2007 | Cholli et al. |
| 2007/0154720 A1 | 7/2007 | Cholli et al. |
| 2007/0161522 A1 | 7/2007 | Cholli et al. |
| 2008/0249335 A1 | 10/2008 | Cholli et al. |
| 2008/0293856 A1 | 11/2008 | Kumar et al. |
| 2008/0311065 A1 | 12/2008 | Cholli |
| 2009/0184294 A1 | 7/2009 | Cholli et al. |

FOREIGN PATENT DOCUMENTS

| | | |
|---|---|---|
| DE | 197 47 644 A1 | 5/1999 |
| DE | 198 43 875 A1 | 3/2000 |
| EP | 0 181 023 A1 | 5/1986 |
| EP | 0 289 077 A2 | 11/1988 |
| EP | 0 358 157 | 3/1990 |
| EP | 0 404 039 A1 | 12/1990 |
| EP | 0 618 203 A1 | 10/1994 |
| EP | 0 688 805 A1 | 12/1995 |
| EP | 1 067 144 A1 | 1/2001 |
| EP | 1 468 968 A1 | 10/2004 |
| FR | 2 183 973 | 1/1974 |
| GB | 1 283 103 | 7/1972 |
| GB | 1 320 169 | 6/1973 |
| GB | 1 372 042 | 10/1974 |
| GB | 1 389 442 | 4/1975 |
| GB | 1 469 245 | 4/1977 |
| GB | 1 482 649 | 8/1977 |
| JP | 69002715 B | 1/1966 |
| JP | 43016520 B4 | 7/1968 |
| JP | 44024274 | 10/1969 |
| JP | 44028850 | 11/1969 |
| JP | 45 2980 | 1/1970 |
| JP | 49 29339 | 3/1974 |
| JP | 57085366 A | 5/1982 |
| JP | 59025814 | 2/1984 |
| JP | 59197447 | 11/1984 |
| JP | 60-199832 | 10/1985 |
| JP | 05 199858 | 8/1993 |
| JP | 06135876 A | 5/1994 |
| JP | 06 247959 | 9/1994 |
| JP | 08027226 A | 1/1996 |
| JP | 09262069 | 10/1997 |
| JP | 09 328519 | 12/1997 |
| JP | 09 328521 | 12/1997 |
| JP | 9322784 A | 12/1997 |
| JP | 11-80063 | 3/1999 |
| JP | 11-158103 | 6/1999 |
| JP | 2003138258 | 5/2003 |
| NL | 7 905 000 | 3/1980 |
| WO | WO 92/20734 | 11/1992 |
| WO | WO 2000/39064 | 7/2000 |
| WO | WO 01/18125 A1 | 3/2001 |
| WO | WO 01/48057 A1 | 7/2001 |
| WO | WO 02/079130 A1 | 10/2002 |
| WO | WO 2003/087260 A1 | 10/2003 |
| WO | WO 03/102004 A1 | 12/2003 |
| WO | WO 2004/024070 A2 | 3/2004 |
| WO | WO 2004/050795 A2 | 6/2004 |
| WO | WO 2005/025513 A2 | 3/2005 |
| WO | WO 2005/025646 A2 | 3/2005 |
| WO | WO 2005/060500 A2 | 7/2005 |
| WO | WO 2005/070974 A2 | 8/2005 |
| WO | WO 2005/071005 A1 | 8/2005 |
| WO | WO 2006/018403 A1 | 2/2006 |
| WO | WO 2006/060801 A2 | 6/2006 |
| WO | WO 2006/104957 A2 | 10/2006 |
| WO | WO 2008/005358 A2 | 1/2008 |

OTHER PUBLICATIONS

Belyaev, A., et al., "Structure-Activity Relationship of Diaryl Phosphonate Esters as Potent Irreversible Dipeptidyl Peptidase IV Inhibitors," *J. Med. Chem.*, 42(6):1041-1052 (1998).

Blokhin, Y.I, et al., "Phosphorylation of Dihydric Phenols with Amides of Phosphorous Acid," *Russian Chem. Bulletin*, 45(9):2250-2251 (1996).

Bruno, F.F., et al., "Enzymatic Template Synthesis of Polyphenol," Materials Research Society Symposium Proceedings vol. 600, Electroactive Polymers (EAP):255-259 (1999).

Chandra, K.G. And Sharma, M.M., "Alkylation of Phenol with MTBE and Other tert-butyl-ethers: Cation Exchange Resins as Catalysts," *Catal. Lett.* 19(4):309-317 (1993).

Ciric-Marjanovic, et al., Chemical Oxidative Polymerization of Aminodiphenylamines, Journal of Physical Chemistry B, 112, 23: 6976-6987 (2008).

Coppinger, G.B., et al., "Photo-Fries Rearrangement of Aromatic Esters. Role of Steric and Electronic Factors" *J. of Phy. Chem.*, 70(11):3479-3489 (1966).

Database CA [online] Chemical Abstracts Service, Columbus, Ohio, US, XP-002429584, Database Accession No. 81::153647, Organic Phosphate Stabilizers for Polyamides and Polyurethanes, abstract, Minagawa, M. (1974).

Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.

Devassy, B.M., et al., "Zirconia Supported Phosphotungstic Acid as an Efficient Catalyst for Resorcinol Cert-Butylation and n-Heptane Hydroisomerization," *J. Mol. Catalysis A: Chemical* 221:113-119 (2004).

Ding, et al., "Chemical Trapping Experiments Support a Cation-Radical Mechanism for the Oxidative Polymerization of Aniline," Journal of Polymer Science, Part A: Polymer Chemistry, vol. 37: 2569-2579 (1999).

Dordick, J.S., "Enzymatic Catalysis in Monophasic Organic Solvents," *Enzyme Microb. Technol.*, 11(4):194-211 (1989).

Dordick, J.S., et al., "Polymerization of Phenols Catalyzed by Peroxidase in Nonaqueous Media," *Biotechnology and Bioengineering*, 30(1):31-36 (1987).

English Abstract of Kovalev, G. I., et al., "Study of the Effectiveness of Inhibitors in Oxidation of Jet Fuel in a Closed Volume, "*Deposited Doc.*, VINITI: 443-82 (1981).

English Abstract of Kovalev, G.I., et al., "Effectiveness of Inhibitors in the Oxidation of Jet Fuel With an Initiator," *J. Neftekhimiya (Petroleum Chemistry)*, 21(2): 287-298 (1981).

Faber, K., "Biotransformations in Organic Chemistry," A Textbook, Fourth Completely Revised and Extended Edition, Springer-Verlag pp: 347-349 (1953).

Hatayama, K., et al., "Anti-ulcer Effect of Isoprenyl Flavonoids. III[1]. Synthesis and Anti-ulcer Activity of Metabolites of 2'-Carboxymethoxly-4,4'-bis(3-methyl-2-butenyloxy)chalcone[2])," *Chemical & Pharmaceutical Bulletin*, 33(4), 1327-1333(Apr. 1985).

Heidekum, A., et al., "Nafion/Silica Composite Material Reveals High Catalytic Potential in Acylation Reactions," *J. Catal.* 188:230-232 (1999).

Hidalgo, M.E., et al., "Antioxidant Activity of Depsides and Depsidones," Phytochemistry, 37(6):1585-1587 (1994).

Hofer, K., et al., "[[(Anilinooxalyl)amino]phenyl] Phosphite Stabilizers for Polypropylene," Chemical Abstracts Service, ZCAPLUS, document No. 77:62780 (1972).

Ikeda, R., et al., "Novel Synthetic Pathway to a Poly(phenylene oxide). Laccase-Catalyzed Oxidative Polymerization of Syringic Acid," *Macromolecules*, 29:3053-3054 (1996).

International Search Report for related foreign application PCT/US2007/015177, mailed on Jun. 13, 2008.

International Search Report for related foreign application PCT/US2005/044021, mailed on May 22, 2006.

International Search Report for related foreign application PCT/US2005/044022, mailed on May 2, 2006.

International Search Report for related foreign application PCT/US2005/044023, mailed on Nov. 3, 2006.

International Search Report for related foreign application PCT/US2005/044019, mailed on Apr. 28, 2006.

International Search Report for related foreign application PCT/US2005/025646, mailed on Mar. 13, 2006.

International Search Report for related foreign application PCT/US2005/025513, mailed on Mar. 13, 2006.

International Search Report for related foreign application PCT/US2006/006355, mailed on Jul. 31, 2006.

International Search Report for related foreign application PCT/US2006/010985, mailed on Dec. 19. 2006.

International Search Report for related foreign application PCT/US2006/042240, mailed on May 3, 2007.

International Search Report for related foreign application PCT/US2006/042235, mailed on Apr. 27, 2007.

International Search Report for related foreign application PCT/US2006/045929, mailed on Apr. 20, 2007.

Ismail, M.N. and Wazzan, A.A., "Evaluation of New Thermal Stabilizers and Antifatigue Agents for Rubber Vulcanizates," *Polymer-Plastics Tech. And Eng.*, 45:751-758 (2006).

Jayaprakasha, G.K., et al., "Antioxidant Activity of Grape Seed (*Vitis vinifera*) Extracts on Peroxidation Models in Vitro," *Food Chemistry*, 73:285-290 (2001).

Jialanella, G.And Pilrma, I., "Synthesis of Poly(vinyl alcohol-co-vinyl gallate) by the Chemical Modification of Poly(vinyl alcohol)," Polymer Bulletin 18:385-389 (1987).

Joossens, J., et al., "Diphenyl Phosphonate Inhibitors for the Urokinase-Type Plasminogen Activator: Optimization of the P4 Position," *J. Med. Chem.*, 49:5785-5793 (2006).

Kamitori, Y., et al., "Silica Gel as an Effective Catalyst for the Alkylation of Phenols and Some Heterocylic Aromatic Compounds," *J Org. Chem.* 49: 4161-4165 (1984).

Kazandjian, R.Z., et al., "Enzymatic Analyses in Organic Solvents," *Biotechnology and Bioengineering*, XXVIII:417-421 (1986).

Khan, K.M., et al., "An Expedient Esterification of Aromatic Carboxylic Acids Using Sodium Bromate and Sodium Hydrogen Sulfite," *Tetrahedron* 59(29):5549-5554 (2003).

Kim, T. H., et al., "Melt Free-Radical Grafting of Hindered Phenol Antioxidant onto Polyethylene," *J. Applied Polymer Science*, 77:2968-2973 (2000).

Klibanov, A.M., et al., "Enzymatic Removal of Toxic Phenols and Anilines from Waste Waters," *J. of Applied Biochemistry*, 2(5):414-421 (1980).

Koshchii, V.A., et al. "Alkylation of Phenol by Alcohols in the Presence of Alumium Phenolate," *Org. Chem.* 24(7):1358-1361 (1988).

Lalancette, J.M., et al. "Metals Intercalated in Graphite. II. The Friedel-Crafts Reactions with ALCL3-Graphite," *Can. J. Chem.* 52:589-591 (1974).

Li, et al., "Novel Multifunctional Polymers from Aromatic Diamines by Oxidative Polymerizations," Chemical Reviews, vol. 102(9): pp. 2925-2943 (2002).

Maki, M., et al., "Weather-Resistant Colored Polypropylene," Chemical Abstracts Service, ZCAPLUS, document No. 89:111364 (1978).

Mar., J., Advanced Organic Chemistry, McGraw Hill Book Company, New York, pp. 251-259 (1977).

Masada, H. And Oishi, Y., "A New Synthesis of aryl t-butyl Ethers," *Chem. Letters*, 57-58 (1978).

Masada, H. et al., "A New Heterogeneous Williamson Synthesis of Ethers Using t-alkyl Substrates," *The Chemical Society of Japan* 3:275-282 (1996).

Masada, H., et al., "A New Method for the Williamson Ether Synthesis Using t-alkyl Halides in Nonpolar Solvents," *The Chemical Society of Japan*, 2:164-166 (1995).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Mejias, L., et al "New Polymers From Natural Phenols Using Horseradish or Soybean Peroxidase," *Macromol. Biosci.*, 2:24-32 (2002).

Ol'dekop, Yu. A., et al. "Simple Synthesis of the tert-butyl Ether of Phenol" Inst. Fiz-Org. Khim., Minsk, Ussr. *Zhurnal Obshchei Khimii*, 50(2):475-6 (1980).

Overgaag, M., et al., "Rearrangement of Alkyl Phenyl Ethers Over Dealuminated Hy Zeolites Under Liquid-Phase Conditions," *Applied Catalysis A: General, Elsevier Sci.*, 175(1-2):139-146 (1998).

Pätoprsty, V., et al., "I-3C Nmr Study of 3,9-Di(alkylphenoxy)-2,4,8,10-tetraoxa-3,9- diphosphaspiro[5.5]undecanes," *Magnetic Resonance in Chem*, 23(2):122-126 (1985).

Pirozhenko, V.V., et al., "Nmr Study of Topomerization of N-Aroyl-pBenzoquinonemonoimines," *Russian J of Organic Chem.*, 31(11):1514-1519 (1995).

Quaschning, V., et al., "Properties of Modified Zirconia Used as Friedel-Crafts-Acylation Catalysts," *J Catal.* 177:164-174 (1998).

Ryu, K., et al., "Peroxidase-Catalyzed Polymerization of Phenols," Biocatalysis in Agricultural Biotechnology, Chapter1 0:141-157 (1988).

Sakthivel, A., et al., "Vapour Phase Tertiary Butylation of Phenol Over Sulfated Zirconia Catalyst," *Catal. Lett.*, 72(3-4):225-228 (2001).

Sartori G., et al., "Highly Selective Mono-tert-butylation of Aromatic Compounds," *Chem. Ind.*, (London), (22):762-763 (1985).

Scharpe, S.L., et al., "Serine Peptidase Modulators, Their Preparation, and Their Therapeutic Use," Chemical Abstracts Service, ZCAPLUS, document No. 131:223514 (1999).

Notification Concerning Transmittal of Copy of International Search Report and Written Opinion of the International Searching Authority, or the Declaration for application PCT/US2006/042251, mailed on Feb. 22, 2007.

RN 85650-63-1, 1984.

Singh, A. and Kaplan, D. L., "Biocatalytic Route to Ascorbic Acid-Modified Polymers for Free- Radical Scavenging," *Adv. Matter.*, 15(15):1291-1294 (2003).

Spano, R., et al., "Substituted Anilides of 3-Monoethyl Ester of 4 Hydroxyisophthalic Acid," *J. of Med. Chem.*, 15(5):552-553.

Thompson, C. Ray, "Stability of Carotene in Alfalfa Meal: Effect of Antioxidants," *Industrial & Engineering Chemistry*, 24(5): 922-925 (1950).

Tsvetkov, O.N., et al., "Alkylation of Phenols with Higher Olefins. Part I," *Int. Chem. Eng.* 7(1):104-121 (1967).

XP-002419239, "Discover Our World of Effects for Polyolefins," *Ciba Speciality Chemicals*, (2003).

Notification of Transmittal of the International Search Report and the Written Opinion of the International Searching Authority, or the Declaration for related foreign application PCT/US2007/015177, mailed on Jun. 13, 2008.

Notification Concerning Transmittal of Copy of International Preliminary Report on Patentability for related foreign application PCT/US2007/015177, mailed on Jan. 15, 2009.

Al-Malaika, S and Suharty, N., "Reactive Processing of Polymers: Mechanisms of Grafting Reactions of Functional Antioxidants on Polyolefins in the Presence of a Coagent," Polymer Degradation and Stability 49: 77-89 (1995).

Notification Concerning Transmittal of Copy of International Preliminary Report on Patentability for application PCT/US2006/042251, mailed on May 8, 2008.

Written Opinion for related foreign application PCT/US2005/025646, mailed on Nov. 14, 2006.

Notification Concerning Transmittal of Copy of International Preliminary Report on Patentability for related foreign application PCT/US2005/025646, mailed on Dec. 20, 2006.

*U.S. Appl. No. 12/082,967: Office Action mailed Jan. 27, 2009.

*U.S. Appl. No. 12/082,967: Office Action mailed Aug. 4, 2009.

U.S. Appl. No. 12/082,967: Request for Continued Examination, Amendment and Remarks mailed Jan. 4, 2010.

*U.S. Appl. No. 12/082,967: Notice of Allowance mailed Jan. 27, 2010.

International Preliminary Report on Patentability for PCT/US2005/001946, issued Jul. 24, 2006.

International Preliminary Report on Patentability and Written Opinion for related foreign application PCT/US2005/025513, issued Jan. 23, 2007.

* cited by examiner

STABILIZED POLYOLEFIN COMPOSITIONS

RELATED APPLICATIONS

This application is a continuation of U.S. application Ser. No. 11/293,844, filed Dec. 2, 2005 now U.S. Pat. No. 7,902,317, which claims the benefit of U.S. Provisional Application No. 60/633,196, filed on Dec. 3, 2004. The entire teachings of the above applications are incorporated herein by reference.

BACKGROUND OF THE INVENTION

Antioxidants are employed to prevent oxidation in a wide range of materials, for example, plastics, elastomers, lubricants, petroleum based products (lubricants, gasoline, aviation fuels, and engine oils), cooking oil, cosmetics, processed food products, and the like. While many antioxidants exist, there is a continuing need for new antioxidants that have improved properties.

SUMMARY OF THE INVENTION

The present invention relates to compositions comprising antioxidants and stabilizers, such as, acid scavengers or organic phosphorus stabilizers and optionally further comprising co-stabilizers. These compositions are useful as stabilizers for polyolefins and other polymeric materials.

In one embodiment the present invention is a composition comprising an antioxidant, and at least one additive selected from the group consisting of a phosphorus stabilizer (e.g., a phosphate or phosphite stabilizer), an acid stabilizer and a co-stabilizer.

In another embodiment, the present invention is a polyolefin composition comprising a polyolefin or a mixture of polyolefins, an antioxidant, and at least one additive selected from the group consisting of a phosphorus stabilizer (e.g., a phosphate or phosphite stabilizer), an acid stabilizer and a co-stabilizer.

In yet another embodiment, the present invention is a method of preventing oxidation in a polyolefin or a mixture of polyolefins comprising combining the polyolefin or mixture of polyolefins with an antioxidant, and at least one additive selected from the group consisting of a phosphorus stabilizer (e.g., a phosphate or phosphite stabilizer), an acid stabilizer and a co-stabilizer.

The compositions and methods of the present invention generally provide longer shelf life and better oxidative resistance to materials than currently available antioxidants.

DETAILED DESCRIPTION OF THE INVENTION

Figure 1:
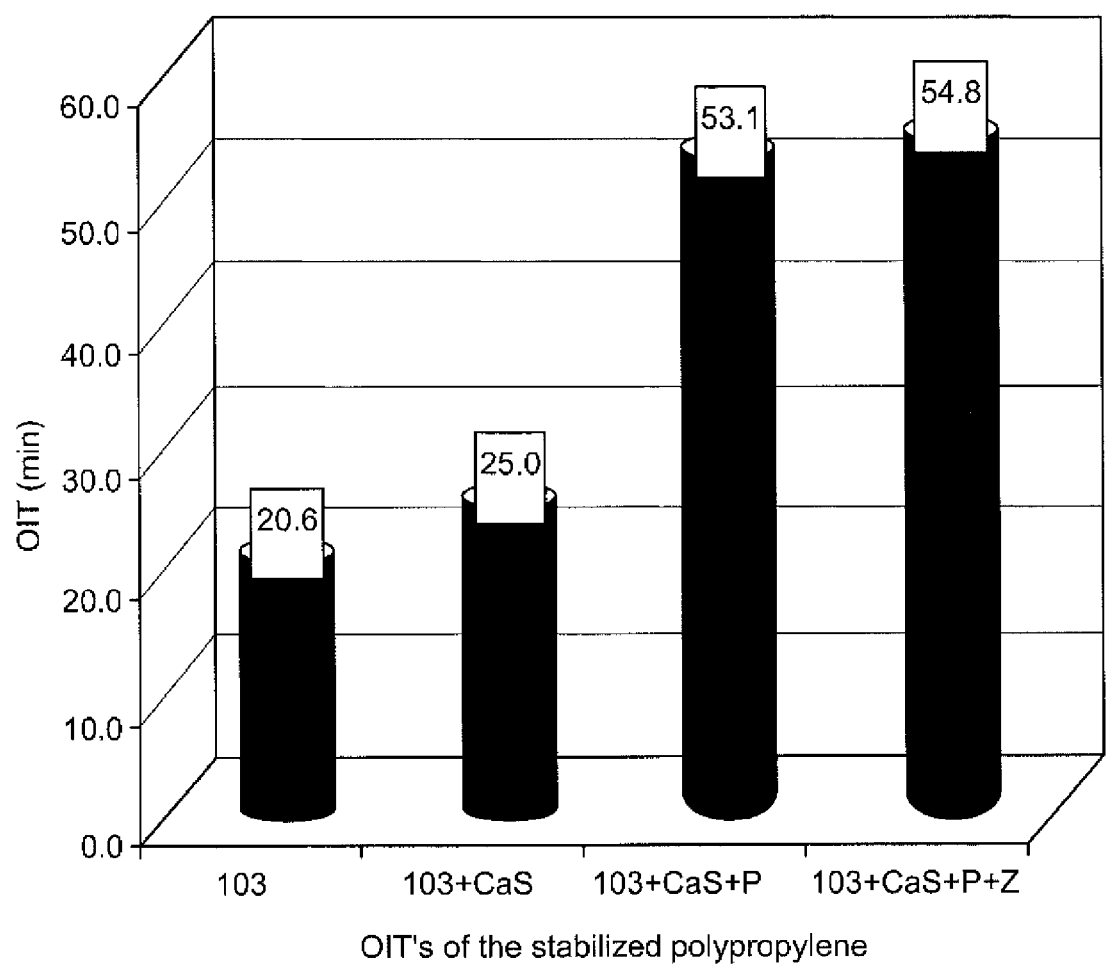
FIG. 1, is a comparison of an oxidative induction time (OIT) of polypropylene in combination with one embodiment of the invention, namely, benzenepropanamide, 3,5-bis(1,1-dimethylethyl)-4-hydroxy-N-(4-hydroxyphenyl); i) alone, ii) in combination with calcium stearate (CasS), iii) in combination with calcium stearate and phosphate (P) and iv) in combination with calcium sulfide, phosphite and zinc oxide (Z).

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention relates to compositions, such as, polymer processing formulations involving i) antioxidants described in Provisional Patent Application Nos.: 60/632,893, 60/633,197, 60/633,252, 60/633,196, 60/665,638 and 60/655,169, U.S. patent application Ser. Nos.: 11/184,724 (U.S. Patent Publication No. 2006/0041094), 11/184,716 (U.S. Patent Publication No. 2006/0041087), 11/040,193 (U.S. Pat. No. 7,323,511), 10/761,933 (U.S. Pat. No. 7,595,074), 10/408,679 (U.S. Pat. No. 7,223,432) and 10/761,933 (U.S. Pat. No. 7,595,074),; Provisional Patent Application, filed Oct. 27, 2005, Title: Macromolecular Antioxidants And Polymeric Macromolecular Antioxidants, by Ashok L. Cholli, et al.; Provisional Patent Application, filed October 27, 2005, Title: Macromolecular Antioxidants Based On Sterically Hindered Phenols and Phosphites, by Ashok L. Cholli, et al. PCT Patent Application Nos.: PCT/US2005/001948 (WO 2005/070974), PCT/US2005/001946 (WO 2005/071005) and PCT/US03/10782 (WO 2003/087260), the entire contents of each of which are incorporated herein by reference, along with ii) stabilizers such as acid scavengers or organic phosphorus stabilizers and/or iii) co-stabilizers used in polyolefins and other polymeric materials.

In one embodiment, the antioxidants which are suitable for use in the compositions and methods of the present invention include but are not limited to polyalkyl phenol based antioxidants, sterically hindered phenol based antioxidants, sterically hindered phenol based macromolecular antioxidants, nitrogen and hindered phenol containing dual functional macromolecular antioxidants, alkylated macromolecular antioxidants, sterically hindered phenol and phosphite based macromolecular antioxidants.

In one embodiment, the antioxidants which are suitable for use in the compositions and methods of the present invention include antioxidant polymers which comprises repeat units that include one or both of Structural Formulas (I) and (II):

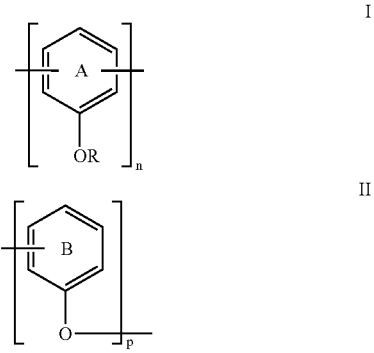

where:
R is —H or a substituted or unsubstituted alkyl, substituted or unsubstituted acyl or substituted or unsubstituted aryl group;

Ring A is substituted with at least one tert-butyl group or substituted or unsubstituted n-alkoxycarbonyl group, and optionally one or more groups selected from the group consisting of —OH, —NH, —SH, a substituted or unsubstituted alkyl or aryl group, and a substituted or unsubstituted alkoxycarbonyl group;

Ring B is substituted with at least one —H and at least one tert-butyl group or substituted or unsubstituted n-alkoxycarbonyl group and optionally one or more groups selected from the group consisting of —OH, —NH, —SH, a substituted or unsubstituted alkyl or aryl group, and a substituted or unsubstituted alkoxycarbonyl group;

n is an integer equal to or greater than 2; and p is an integer equal to or greater than 0.

In another embodiment, the antioxidants which are suitable for use in the compositions and methods of the present invention include polymers with repeat units represented by one or both of Structural Formulas (III) and (IV);

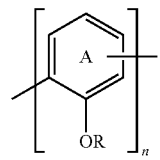

(III)

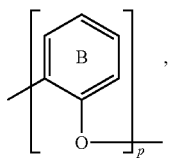

(IV)

where Rings A and B are substituted as described above and n and p are as defined above.

Preferably, Ring A and Ring B in Structural Formulas (I) to (IV) are each substituted with at least one tert-butyl group.

In another embodiment, the antioxidants which are suitable for use in the compositions and methods of the present invention include polymers with repeat units represented by one or more of Structural Formulas (Va), (Vb), (Vc), (VIa), (VIb) and (VIc):

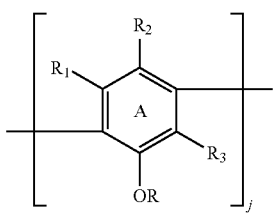

(Va)

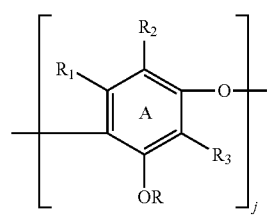

(Vb)

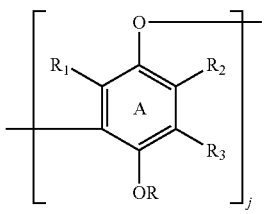

(Vc)

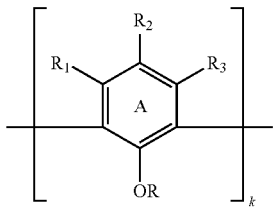

(VIa)

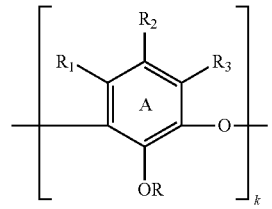

(VIb)

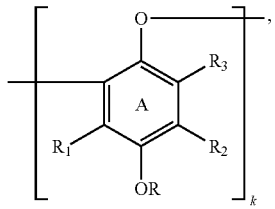

(VIc)

where $R_1$, $R_2$ and $R_3$ are independently selected from the group consisting of —H, —OH, —NH, —SH, a substituted or unsubstituted alkyl or a substituted or unsubstituted aryl group, and a substituted or unsubstituted alkoxycarbonyl group, provided that at least one of $R_1$, $R_2$ and $R_3$ is a tert-butyl group; and j and k are independently integers of zero or greater, such that the sum of j and k is equal to or greater than 2.

In a particular embodiment, R is —H or —CH$_3$; $R_2$ is —H, —OH, or a substituted or unsubstituted alkyl group; or both.

Specific examples of repeat units included in polymers which are suitable for use in the compositions and methods of the present invention are represented by one of the following structural formulas:

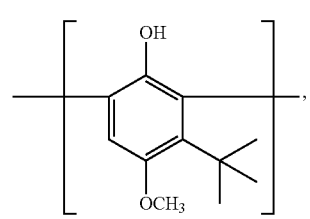

(VII)

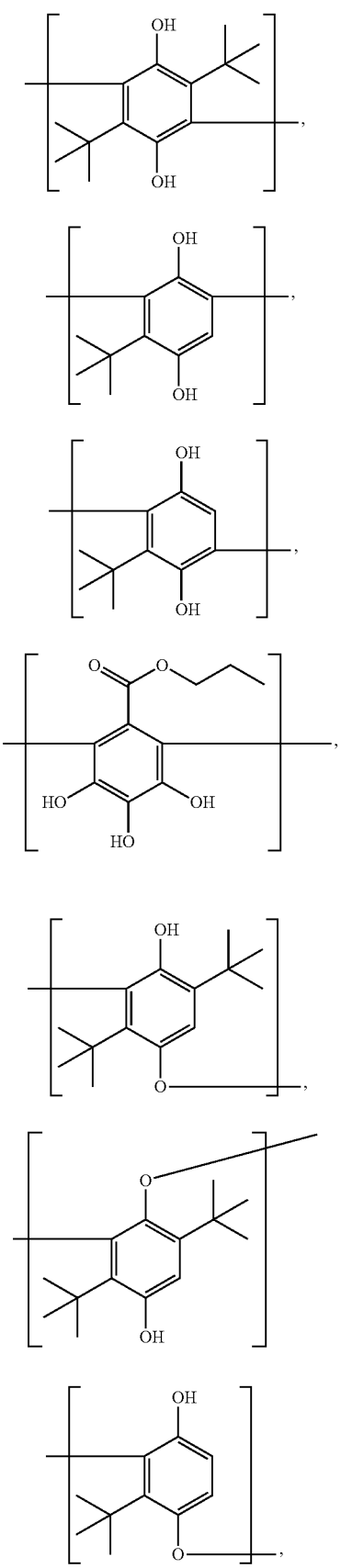
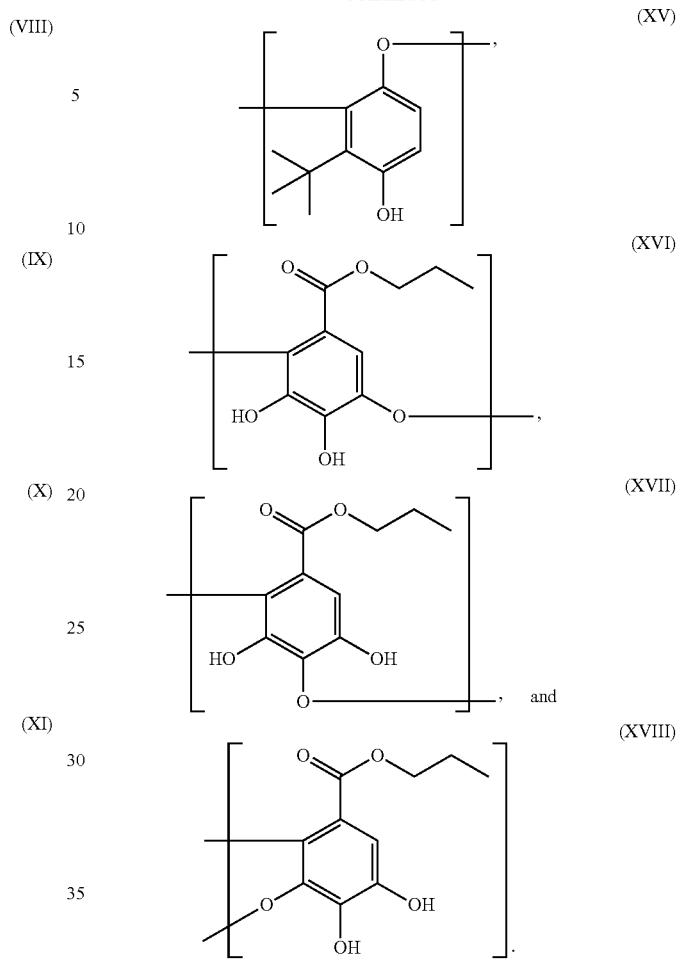

Antioxidant polymers as described immediately above which are suitable for use in the compositions and methods of the present invention have two or more repeat units, preferably greater than about five repeat units. The molecular weight of the polymers disclosed above is generally selected to be appropriate for the desired application. Typically, the molecular weight is greater than about 500 atomic mass units (amu) and less than about 2,000,000 amu, greater than about 1000 amu and less than about 100,000, greater than about 2,000 amu and less than about 10,000, or greater than about 2,000 amu and less than about 5,000 amu.

Antioxidant polymers as described immediately above which are suitable for use in the compositions and methods of the present invention can be either homopolymers or copolymers. A copolymer preferably contains two or more or three or more different repeating monomer units, each of which has varying or identical antioxidant properties. The identity of the repeat units in a copolymer can be chosen to modify the antioxidant properties of the polymer as a whole, thereby giving a polymer with tunable properties. The second, third and/or further repeat units in a copolymer can be either a synthetic or natural antioxidant.

Antioxidant polymers as described immediately above which are suitable for use in the composition and methods of the present invention are typically insoluble in aqueous media. The solubility of the antioxidant polymers in non-aqueous media (e.g., oils) depends upon the molecular weight of the polymer, such that high molecular weight polymers are typically sparingly soluble in non-aqueous media. When an antioxidant polymer of the invention is insoluble in a particular medium or substrate, it is preferably well-mixed with that medium or substrate.

Antioxidant polymers as described immediately above which are suitable for use in the compositions and methods of the present invention can be branched or linear, but are preferably linear. Branched antioxidant polymers can only be formed from benzene molecules having three or fewer substituents (e.g., three or more hydrogen atoms), as in Structural Formulas (XX), (XXI) and (XXIV).

In another embodiment, the antioxidants which are suitable for use in the compositions and methods of the present invention include polymers with repeat units represented by one or both of Structural Formulas (I) and (II):

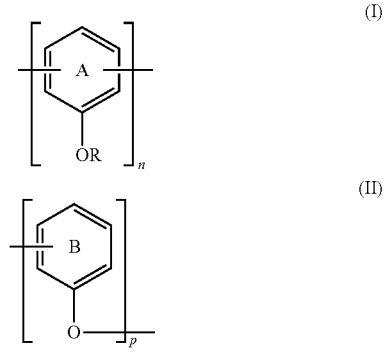

where:
R is —H or a substituted or unsubstituted alkyl, acyl or aryl group;
Ring A is substituted with at least one tert-butyl group, 1-ethenyl-2-carboxylic acid group or ester thereof, substituted or unsubstituted alkenedioxy group, or substituted or unsubstituted n-alkoxycarbonyl group and zero, one or more additional functional groups;
Ring B is substituted with at least one —H and at least one tert-butyl group, 1-ethenyl-2-carboxylic acid group or ester thereof, substituted or unsubstituted alkylenedioxy substituted, or substituted or unsubstituted n-alkoxycarbonyl group and zero, one or more additional functional groups;
n is an integer equal to or greater than 2; and
p is an integer equal to or greater than 0,
where the polymer includes two or more repeat units represented by one or both of Structural Formulas (I) and (II) that are directly connected by a C—C or C—O—C bond between benzene rings.

Polymers as described immediately above which are suitable for use in the compositions and methods of the present invention that do not include any repeat units represented by Structural Formula (I) are preferably substituted on Ring B with one or more hydroxyl or acyloxy groups.

Repeat units of the antioxidant polymers as described immediately above which are suitable for use in the compositions and methods of the present invention include substituted benzene molecules. These benzene molecules are typically based on phenol or a phenol derivative, such that they have at least one hydroxyl, ester or ether functional group. Preferably, the benzene molecules have a hydroxyl group. The hydroxyl group is not restricted to being a free hydroxyl group, and the hydroxyl group can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant polymer is able to exert its antioxidant effect.

Substituted benzene repeat units of an antioxidant polymer as described immediately above which are suitable for use in the compositions and methods of the present invention are also typically substituted with a bulky alkyl group, a 1-ethenyl-2-carboxylic acid group, a substituted or unsubstituted alkenedioxy group, or an n-alkoxycarbonyl group. Preferably, the benzene monomers are substituted with a bulky alkyl group. More preferably, the bulky alkyl group is located ortho or meta to a hydroxyl group on the benzene ring. A "bulky alkyl group" is defined herein as an alkyl group that is branched alpha- or beta- to the benzene ring. Preferably, the alkyl group is branched alpha to the benzene ring. More preferably, the alkyl group is branched twice alpha to the benzene ring (i.e., to form an alpha-tertiary carbon), such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. The bulky alkyl groups are preferably unsubstituted, they they can be substituted with a functional group that does not interfere with the antioxidant activity of the molecule or the polymer.

Substituted benzene repeat units that are substituted with a substituted or unsubstituted alkylenedioxy group typically have an unsubstituted alkylenedioxy group. Substituted alkylenedioxy groups are also suitable, although the substituents should not interfere with the antioxidant activity of the molecule or the polymer. Typically, an alkylenedioxy group is a lower alkylenedioxy group, such as a methylenedioxy group or an ethylenedioxy group. A methylenedioxy group is preferred (as in sesamol).

Straight chained alkoxycarbonyl groups typically have an alkyl chain of one to sixteen carbon atoms, and include methoxycarbonyl, ethoxycarbonyl, n-propoxycarbonyl, n-butoxycarbonyl and n-pentoxycarbonyl, n-propoxycarbonyl is a preferred group. Similar to the bulky alkyl groups, n-alkoxycarbonyl groups are optionally substituted with a functional group that does not interfere with the antioxidant activity of the molecule or the polymer. Alkoxycarbonyl groups can also be present in their hydrolyzed form, namely as carboxy groups or carboxylic acid groups.

In substituted benzene repeat units having a 1-ethenyl-2-carboxylic acid group or an ester thereof, the 1-carbon (i.e., the carbon distal from the carboxylic acid moiety) is attached to the benzene ring.

In addition to the substituents named above, substituted benzene repeat units can have additional functional groups as substituents. For example, the additional functional groups can be selected from the group consisting of —OH, —NH, —SH, a substituted or unsubstituted alkyl or aryl group, a substituted or unsubstituted alkoxycarbonyl group, a substituted or unsubstituted alkoxy group and a saturated or unsaturated carboxylic acid group. Typically, the additional functional groups are selected from the group consisting of —OH, a substituted or unsubstituted alkoxy group and a saturated or unsaturated carboxylic acid group.

Preferably, Ring A and Ring B in Structural Formulas (I) to (IV) are each substituted with at least one tert-butyl group.

Further, specific examples of repeat units included in polymers which are suitable for use in the compositions and methods of the present invention are represented by one of the following structural formulas:

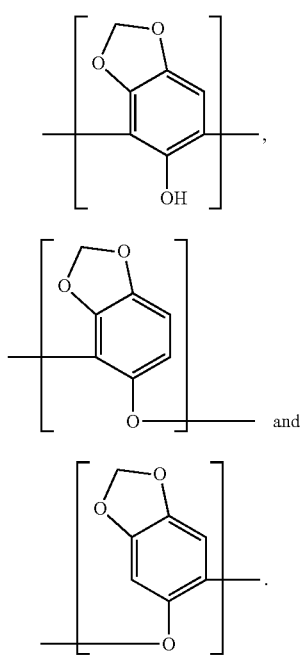

(XVIIIa)

(XVIIIb) and (XVIIIc)

Although Structural Formulas (XI), (XVI), (XVII) and (XVIII) are represented as having a propoxycarbonyl substituent, this group can generally be replaced with a different $C_1$-$C_{16}$ n-alkoxycarbonyl group or can be a carboxylate group.

A particular polymer suitable for use in the methods and compositions of the present invention is poly(2-tert-butyl-4-hydroxyanisole).

Antioxidant polymers as described immediately above which are suitable for use in the methods and compositions of the present invention have two or more repeat units, preferably greater than about five repeat units. The molecular weight of the polymers disclosed herein is generally selected to be appropriate for the desired application. Typically, the molecular weight is greater than about 500 atomic mass units (amu) and less than about 2,000,000 amu, greater than about 1000 amu and less than about 100,000, greater than about 2,000 amu and less than about 10,000 amu, or greater than about 2,000 amu and less than about 5,000 amu.

Antioxidant polymers as described immediately above which are suitable for use in the methods and compositions of the present invention can be either homopolymers of copolymers. A copolymer preferably contains two or more or three or more different repeating monomer units, each of which has varying or identical antioxidant properties (including monomers having no antioxidant activity). The identity of the repeat units in a copolymer can be chosen to modify the antioxidant properties of the polymer as a whole, thereby giving a polymer with tunable properties. The second, third and/or further repeat units in a copolymer can be either a synthetic or natural antioxidant. In one example, a composition of the invention includes one or more homopolymers and one or more copolymers (e.g., in a blend). Preferably, both homopolymers and copolymers include two or more substituted benzene repeat units that are directly connected by a C—C or C—O—C bond. Preferably, at least 50%, such as at least 70%, for example, at least 80%, but preferably about 100% of the repeat units in a copolymer are substituted benzene repeat units directly connected by a C—C or C—O—C bond.

Examples of copolymers include poly(TBHQ-co-propyl gallate), poly(TBHQ-co-BHA), poly(TBHQ-co-sesamol), poly(BHA-co-sesamol), poly(propyl gallate-co-sesamol) and poly(BHA-co-propyl gallate). The ratio of one monomer to another, on a molar basis, is typically about 100:1 to about 1:100, such as about 10:1 to about 1:10, for example, about 2:1 to about 1:2. In one example, the ratio of monomers is about 1:1.

Antioxidant polymers as described immediately above which are suitable for use in the methods and compositions of the present invention are typically insoluble in aqueous media, although certain polymers of gallic acid and its ester are water soluble. The solubility of the antioxidant polymers in non-aqueous media (e.g., oils) depends upon the molecular weight of the polymer, such that high molecular weight polymers are typically sparingly soluble in non-aqueous media. When an antioxidant polymer of the invention is insoluble in a particular medium or substrate, it is preferably well-mixed with that medium or substrate.

Antioxidant polymers as described immediately above which are suitable for use in the methods and compositions of the present invention can be branched or linear, but are preferably linear. Branched antioxidant polymers can only be formed from benzene molecules having three or fewer substituents (e.g., three or more hydrogen atoms), as in Structural Formulas (XX), (XXI) and (XXIV).

In another embodiment, the antioxidants which are suitable for use in the compositions and methods of the present invention include a polyalkylphenol antioxidant represented by Structural Formula U.

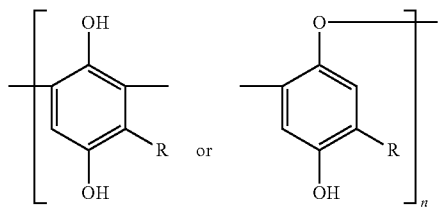

U

In Structural Formula U, n is an integer equal or greater than 2. R is a C1-C10 alkyl group, an aryl group, or a benzyl group. Typically, R is a tertiary alkyl group, or in preferred embodiments, a tertiary butyl group.

Repeat units of the antioxidant polymers as described immediately above which are suitable for use in the compositions and methods of the present invention include substituted benzene molecules. These benzene molecules are typically based on phenol or a phenol derivative, such that they have at least one hydroxyl or ether functional group. Preferably, the benzene molecules have a hydroxyl group. The hydroxyl group can be a free hydroxyl group and can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant polymer can exert its antioxidant effect. The repeat units can also include analogous thiophenol and aniline derivatives, e.g., where the phenol —OH can be replaced by —SH, —NH—, and the like.

Substituted benzene repeat units of an antioxidant polymer as described immediately above which are suitable for use in the compositions and methods of the present invention are also typically substituted with a bulky alkyl group or an n-alkoxycarbonyl group. Preferably, the benzene monomers are substituted with a bulky alkyl group. More preferably, the bulky alkyl group is located ortho or meta to a hydroxyl group on the benzene ring, typically ortho. A "bulky alkyl group" is defined herein as an alkyl group that is branched alpha- or beta- to the benzene ring. Preferably, the alkyl group is branched alpha to the benzene ring. More preferably, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. The bulky alkyl groups are preferably unsubstituted, but they can be substituted with a functional group that does not interfere with the antioxidant activity of the molecule or the polymer. Straight chained alkoxylcarbonyl groups include methoxycarbonyl, ethoxycarbonyl, n-propoxycarbonyl, n-butoxycarbonyl and n-pentoxycarbonyl, n-propoxycarbonyl is a preferred group. Similar to the bulky alkyl groups, n-alkoxycarbonyl groups are optionally substituted with a functional group that does not interfere with the antioxidant activity of the molecule or the polymer.

In another embodiment, the antioxidants which are suitable for use in the compositions and methods of the present invention include a polymer comprising repeat units represented by one or both of Structural Formulas (i) and (ii):

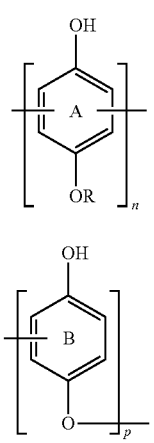

where:
Ring A is substituted with at least one tert-butyl group, and optionally one or more groups selected from the group consisting of a substituted or unsubstituted alkyl or aryl group, and a substituted or unsubstituted alkoxycarbonyl group;

Ring B is substituted with at least one —H and at least one tert-butyl group and optionally one or more groups selected from the group consisting of—a substituted or unsubstituted alkyl or aryl group, and a substituted or unsubstituted alkoxycarbonyl group;

n is an integer equal to or greater than 2; and p is an integer equal to or greater than 0.

In another embodiment, the antioxidants which are suitable for use in the compositions and methods of the present invention are polymers represented by one or both of Structural Formulas (iv) and (v):

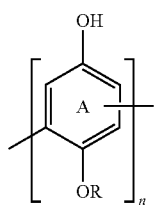

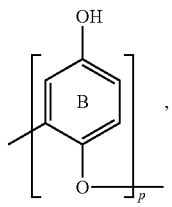

where Ring A is substituted with at least one tert-butyl group, and optionally one or more groups selected from the group consisting of a substituted or unsubstituted alkyl or aryl group, and a substituted or unsubstituted alkoxycarbonyl group; Ring B is substituted with at least one —H and at least one tert-butyl group and optionally one or more groups selected from the group consisting of a substituted or unsubstituted alkyl or aryl group, and a substituted or unsubstituted alkoxycarbonyl group; R is —H, an optionally substituted C1-C10 alkyl group, an aryl group, a benzyl group, or an acyl group n is an integer equal to or greater than 2; and p is an integer equal to or greater than 0. In one embodiment R is a C1-C10 branched or linear alkyl group.

Antioxidant polymers as described immediately above which are suitable for use in the methods of the present invention have two or more repeat units, preferably greater than about five repeat units. The molecular weight of the polymers disclosed herein can be generally selected to be appropriate for the desired application. Typically, the molecular weight can be greater than about 500 atomic mass units (amu) and less than about 2,000,000 amu, greater than about 1,000 amu and less than about 100,000, greater than about 2,000 amu and less than about 10,000, or greater than about 2,000 amu and less than about 5,000 amu.

Antioxidant polymers as described immediately above which are suitable for use in the methods of the present invention can be either homopolymers or copolymers. A copolymer preferably contains two or more or three or more different repeating monomer units, each of which has varying or identical antioxidant properties. The identity of the repeat units in a copolymer can be chosen to modify the antioxidant properties of the polymer as a whole, thereby giving a polymer with tunable properties. The second, third and/or further repeat units in a copolymer can be either a synthetic or natural antioxidant.

Antioxidant polymers as described immediately above which are suitable for use in the methods of the present invention are typically insoluble in aqueous media. The solubility of the antioxidant polymers in non-aqueous media (e.g., oils) depends upon the molecular weight of the polymer, such that high molecular weight polymers are typically sparingly soluble in non-aqueous media. When an antioxidant polymer of the invention can be insoluble in a particular medium or substrate, it can be preferably well-mixed with that medium or substrate.

Antioxidant polymers as described immediately above which are suitable for use in the methods of the present invention can be branched or linear, but are preferably linear. Branched antioxidant polymers can only be formed from benzene molecules having three or fewer substituents (e.g., three or more hydrogen atoms), as in Structural Formulas (XX), (XXI) and (XXIV).

Another specific example of a repeat unit included in polymers which are suitable for use in the compositions and methods of the present invention is represented by the following structural formula:

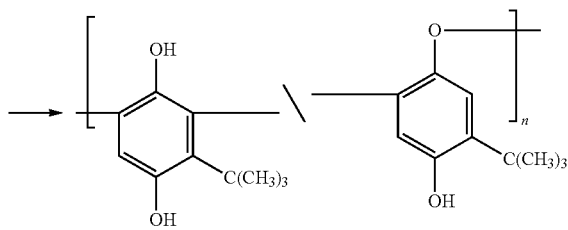

In another embodiment, the antioxidant polymers which are suitable for use in the compositions and methods of the present invention includes a macromolecule which can be represented by one or both of Structural Formulas R and S:

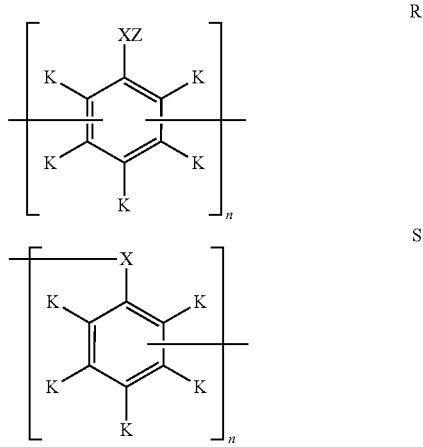

In Structural Formulas R and S, n is an integer equal to or greater than 2.

The variable X is O, NH, or S.

The variable Z is H.

Each variable K is independently —H or —OH, with at least one —OH adjacent to a —; or K is a bond when that position is involved in the polymer chain.

In another embodiment, the antioxidants which are suitable for use in the compositions and methods of the present invention includes a macromolecular antioxidant polymer represented by one or both of Structural Formulas T and V:

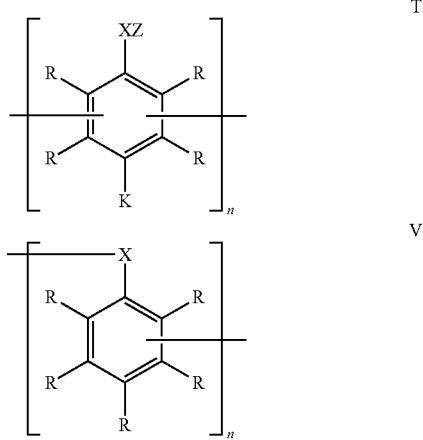

In Structural Formulas T and V, n is an integer equal to or greater than 2.

The variable X is O, NH, or S.

The variable Z is H.

Each variable R is independently —H, —OH, a C1-C10 alkyl group, or a bond when that position is involved in the polymer chain wherein at least one —OH is adjacent to a C1-C10 alkyl group, e.g., a tertiary butyl group.

These macromolecular antioxidant polymers can contain, for example, tert-butylhydroquinone, 2,5-di-tert-butylhydroquinone, BHT type repeat units and their combinations. In some embodiments, of the macromolecular antioxidants described immediately above can be homopolymers, copolymers, terpolymers, and the like Substituted benzene repeat units of an antioxidant polymer as described immediately above which are suitable for use in the methods and compositions of the present invention are typically substituted with a bulky alkyl group or an n-alkoxycarbonyl group. Preferably, the benzene monomers are substituted with a bulky alkyl group. More preferably, the bulky alkyl group is located ortho or meta to a hydroxyl group on the benzene ring, typically ortho. A "bulky alkyl group" is defined herein as an alkyl group that is branched alpha- or beta- to the benzene ring. Preferably, the alkyl group is branched alpha to the benzene ring. More preferably, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. The bulky alkyl groups are preferably unsubstituted, but they can be substituted with a functional group that does not interfere with the antioxidant activity of the molecule or the polymer. Straight chained alkoxylcarbonyl groups include methoxycarbonyl, ethoxycarbonyl, n-propoxycarbonyl, n-butoxycarbonyl and n-pentoxycarbonyl, n-propoxycarbonyl is a preferred group. Similar to the bulky alkyl groups, n-alkoxycarbonyl groups are optionally substituted with a functional group that does not interfere with the antioxidant activity of the molecule or the polymer.

Antioxidant polymers as described immediately above which are suitable for use in the methods and compositions of the present invention have two or more repeat units, preferably greater than about five repeat units. The molecular weight of the polymers disclosed herein can be generally selected to be appropriate for the desired application. Typically, the molecular weight can be greater than about 500 atomic mass units (amu) and less than about 2,000,000 amu, greater than about 1,000 amu and less than about 100,000, greater than about 2,000 amu and less than about 10,000, or greater than about 2,000 amu and less than about 5,000 amu.

Antioxidant polymers as described immediately above which are suitable for use in the methods and compositions of the present invention can be either homopolymers or copolymers. A copolymer preferably contains two or more or three or more different repeating monomer units, each of which has varying or identical antioxidant properties. The identity of the repeat units in a copolymer can be chosen to modify the antioxidant properties of the polymer as a whole, thereby giving a polymer with tunable properties. The second, third and/or further repeat units in a copolymer can be either a synthetic or natural antioxidant.

Antioxidant polymers as described immediately above which are suitable for use in the methods and compositions of the present invention are typically insoluble in aqueous media. The solubility of the antioxidant polymers in non-aqueous media (e.g., oils) depends upon the molecular weight of the polymer, such that high molecular weight polymers are typically sparingly soluble in non-aqueous media. When an antioxidant polymer of the invention can be insoluble in a particular medium or substrate, it can be preferably well-mixed with that medium or substrate.

Antioxidant polymers as described immediately above which are suitable for use in the methods and compositions of the present invention can be branched or linear, but are preferably linear. Branched antioxidant polymers can only be formed from benzene molecules having three or fewer substituents (e.g., three or more hydrogen atoms), as in Structural Formulas (XX), (XXI) and (XXIV).

Specific examples of repeat units included in polymers which are suitable for use in the compositions and methods of the present invention are represented by one of the following structural formulas:

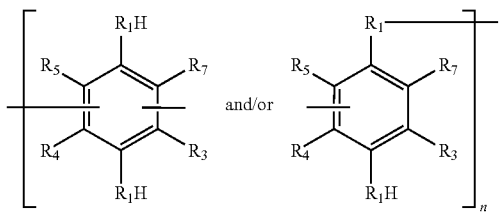

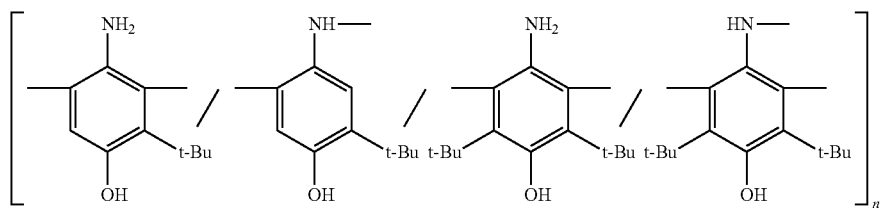

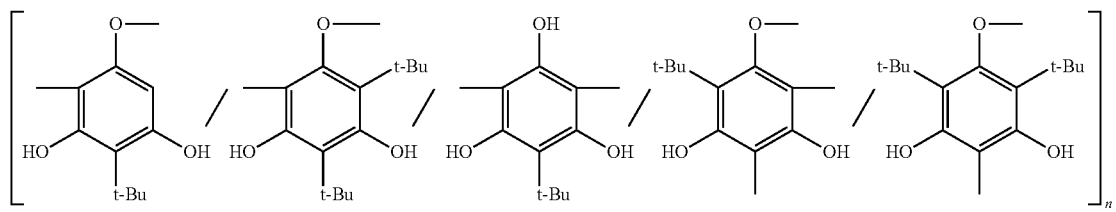

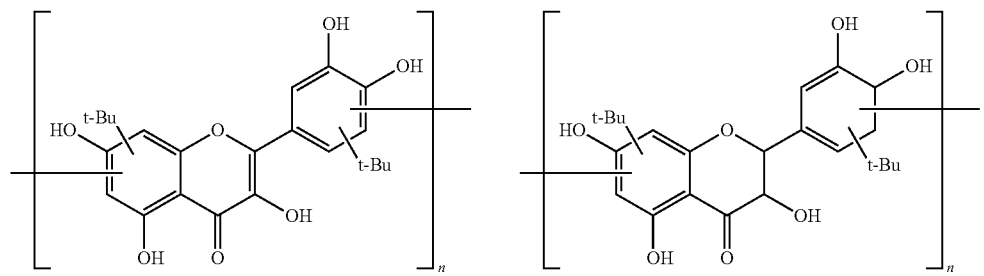

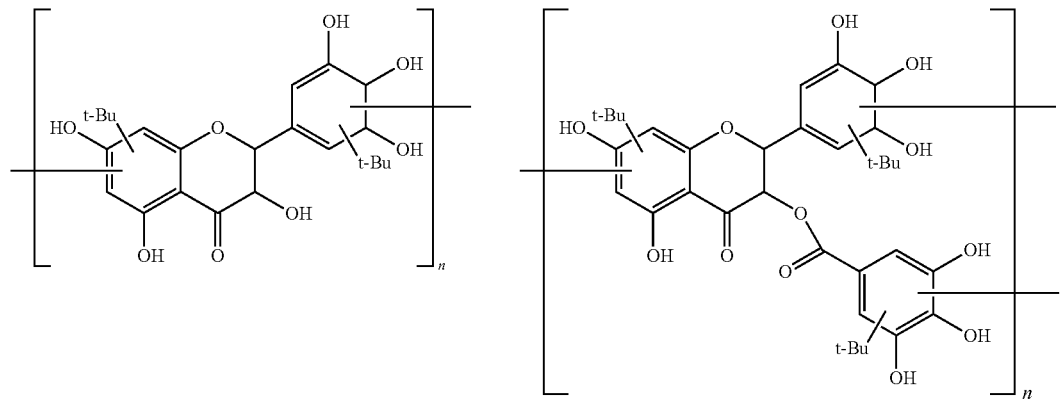

n is an integer equal to or greater than 2.

In another embodiment, the antioxidants which are suitable for use in the compositions and methods of the present invention includes an antioxidant polymer represented by Structural Formula M.

In Structural Formula M:

n is an integer equal to or greater than 2;

$R_1$ is O, S, or NH;

$R_4$, $R_5$, $R_7$ and $R_8$ are independently —H, —OH, —NH, —SH, a substituted or unsubstituted alkyl or aryl group, or a substituted or unsubstituted alkoxycarbonyl group, or a bond when part of the polymer chain, provided that:

(1) at least one of $R_4$, $R_5$, $R_7$ and $R_8$ is a tert-butyl group or a substituted or unsubstituted alkoxycarbonyl group, and at least two of $R_4$, $R_5$, $R_7$ and $R_8$ are —H; or (2) at least one of $R_4$, $R_5$, $R_7$ and $R_8$ is a tert-butyl group or a substituted or unsubstituted alkoxycarbonyl group, at least one of $R_4$, $R_5$, $R_7$ and $R_8$ is a hydroxyl, alkoxy, alkoxycarbonyl or aryloxycarbonyl group, and at least one of $R_4$, $R_5$, $R_7$ and $R_8$ is —H.

Substituted benzene repeat units of an antioxidant polymer as described immediately above which are suitable for use in the methods and compositions of the present invention are also typically substituted with a bulky alkyl group or an n-alkoxycarbonyl group. Preferably, the benzene monomers are substituted with a bulky alkyl group. More preferably, the bulky alkyl group is located ortho or meta to a hydroxyl group on the benzene ring, typically ortho. A "bulky alkyl group" is defined herein as an alkyl group that is branched alpha- or beta- to the benzene ring. Preferably, the alkyl group is branched alpha to the benzene ring. More preferably, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. The bulky alkyl groups are preferably unsubstituted, but they can be substituted with a functional group that does not interfere with the antioxidant activity of the molecule or the polymer. Straight chain alkoxylcarbonyl groups include methoxycarbonyl, ethoxycarbonyl, n-propoxycarbonyl, n-butoxycarbonyl and n-pentoxycarbonyl. n-propoxycarbonyl is a preferred group. Similar to the bulky alkyl groups, n-alkoxycarbonyl groups are optionally substituted with a functional group that does not interfere with the antioxidant activity of the molecule or the polymer.

Antioxidant polymers as described immediately above which are suitable for use in the methods and compositions of the present invention have two or more repeat units, preferably greater than about five repeat units. The molecular weight of the polymers disclosed herein can be generally selected to be appropriate for the desired application. Typically, the molecular weight can be greater than about 500 atomic mass units (amu) and less than about 2,000,000 amu, greater than about 1,000 amu and less than about 100,000, greater than about 2,000 amu and less than about 10,000, or greater than about 2,000 amu and less than about 5,000 amu.

Antioxidant polymers as described immediately above which are suitable for use in the methods and compositions of the present invention can be either homopolymers or copolymers. A copolymer preferably preferably contains two or more or three or more different repeating monomer units, each of which has varying or identical antioxidant properties. The identity of the repeat units in a copolymer can be chosen to modify the antioxidant properties of the polymer as a whole, thereby giving a polymer with tunable properties. The second, third and/or further repeat units in a copolymer can be either a synthetic or natural antioxidant.

Antioxidant polymers as described immediately above which are suitable for use in the methods and compositions of the present invention are typically insoluble in aqueous media. The solubility of the antioxidant polymers in non-aqueous media (e.g., oils) depends upon the molecular weight of the polymer, such that high molecular weight polymers are typically sparingly soluble in non-aqueous media. When an antioxidant polymer of the invention can be insoluble in a particular medium or substrate, it can be preferably well-mixed with that medium or substrate.

Antioxidant polymers as described immediately above which are suitable for use in the methods and compositions of the present invention can be branched or linear, but are preferably linear. Branched antioxidant polymers can only be formed from benzene molecules having three or fewer substituents (e.g., three or more hydrogen atoms), as in Structural Formulas (XX), (XXI) and (XXIV).

In another embodiment, antioxidants which are suitable for use in the compositions and methods of the present invention include a polymer having at least one repeat unit that is represented by a structure selected from the group consisting of Structural Formulas (A), (B), (C), (D) and combinations thereof:

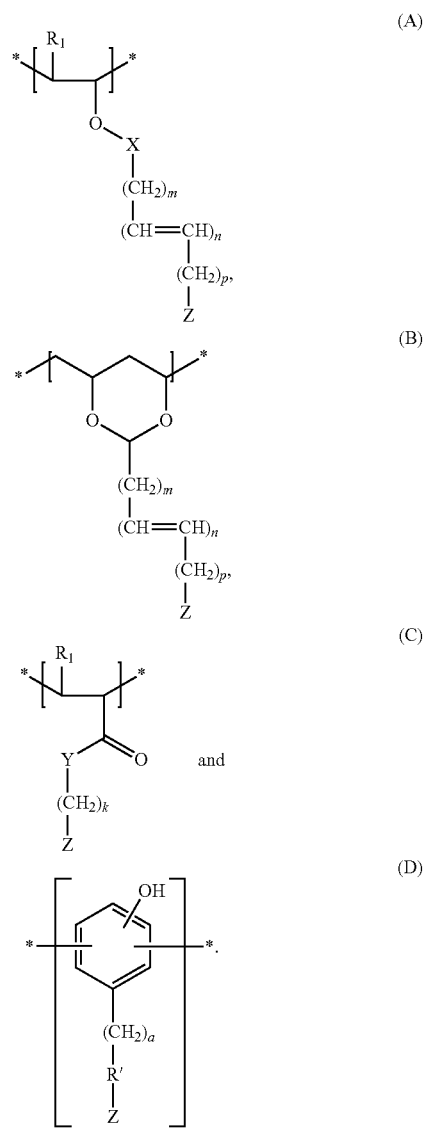

R' is a covalent bond, —O—, —C(O)O—, —C(O)N—, —C(O)—, —CH═CH—, —S— or —N—, $R_1$ is —H or an alkyl group, or —$(CH_2)_k$—O—X—Z. Typically, $R_1$ is —H or alkyl.

Each X is independently a covalent bond, —C(O)—, —C(O)O— or —C(O)N—.

Y is —O—, —N— or —S—.

Each Z is an independently selected antioxidant.

a is an integer from 0 to 12.

Each k is independently an integer from 0 to 12.

m is an integer from 0 to 6.

n is 0 or 1.

p is an integer from 0 to 6.

In one embodiment, the polymer does not include cyclic anhydride repeat units.

An antioxidant can be attached to the polymer by one or more linkages or bonds. Examples of suitable linkages include acetal, amide, amine, carbamate, carbonate, ester, ether and thioether linkage. Carbon-carbon bonds can be also suitable. As used herein, an amide is distinguished from a diacyl hydrazide.

There are many examples of polymers that can be derivatized with an antioxidant. One type of such polymer has pendant hydroxyl groups, such as poly(vinyl alcohol) and copolymers thereof (e.g., poly(ethylene-co-vinyl alcohol)). The hydroxyl groups of poly(vinyl alcohol), a polyhydroxyalkyl methacrylate (e.g., polyhydroxy methyl methacrylate), and poly(ethylene-co-vinyl alcohol) react with an antioxidant to form the derivatized antioxidant polymer. Another type of derivatizable polymer contains pendant carboxylic acid groups or esters thereof, such as poly(acrylic acid), poly (alkylacrylic acid) and esters thereof. Poly(acrylic acid) is a preferred polymer; the carboxylic acid groups of poly(acrylic acid) can be derivatized, although carboxylic acid groups generally require activation before derivatization can occur.

An additional type of derivatizable polymer can be a poly (substituted phenol), where the substituted phenol has a substituent with a nucleophilic or electrophilic moiety. Such poly(substituted phenols) can include repeat units represented by the following structural formulas:

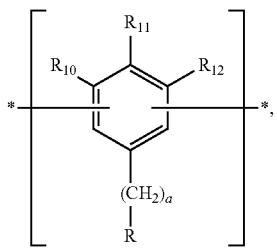

where a is an integer from 0 to 12; R is —OH, —COOH, —NH$_2$, —SH or a halogen; and R$_{10}$, R$_{11}$ and R$_{12}$ are each independently —H, —OH, —NH$_2$ or —SH, provided that at least one of R$_{10}$, R$_{11}$ and R$_{12}$ is —OH, —NH$_2$ or —SH. Preferably, one of R$_{10}$, R$_{11}$ and R$_{12}$ is —OH and the remaining two are optionally —H. More preferably, R$_{11}$ is —OH and R$_{10}$ and R$_{12}$ are —H.

The derivatizable polymers can be homopolymers or copolymers. Copolymers include, for example, block, star, hyperbranched, random, gradient block, and alternate copolymers. The derivatizable polymers can be branched or linear, but are preferably linear.

In copolymers, it is only necessary for one repeat unit to include a pendant reactive group. Second and further repeat units of a copolymer can optionally include a pendant reactive group. For example, about 1% to 100%, such as 10% to 50% or 50% to 100%, of the repeat units of a polymer include pendant functional groups.

All or a fraction of the pendant reactive groups of a derivatizable polymer can be derivatized with an antioxidant. In one example, about 100% of the pendant reactive groups can be derivatized. In another example, about 5% to about 90%, such as about 20% to about 80% (e.g., about 50% to about 80%) of the pendant reactive groups can be derivatized.

These polymers can be minimally derivatized with a single type of antioxidant, but can be derivatized with two or more antioxidants (e.g., chemically distinct antioxidants). When there can be two or more antioxidants, they can be in the same class, as described below, or can be in different classes. The ratio of antioxidants can be varied in order to obtain a polymer having a desired set of properties. For example, when a polymer can be derivatized with two antioxidants, the ratio of a first antioxidant to a second antioxidant can be from about 20:1 to about 1:20, such as from about 5:1 to about 1:5 (e.g., about 1:1).

Many antioxidants can be suitable, provided that they can be attached to a polymer and retain their antioxidant activity. One class of suitable antioxidants can be phenolic antioxidants. Phenolic antioxidants typically have one or more bulky alkyl groups (alkyl groups having a secondary or tertiary carbon alpha to the phenol ring) ortho or meta, preferably ortho, to the phenol hydroxyl group. Phenolic antioxidants can alternatively have an alkylenedioxy substituent, an alkoxycarbonyl substituent, a 1-propenyl-3-carboxylic acid substituent or an ester thereof. A preferred bulky alkyl group is a tert-butyl group. The phenol hydroxyl group can be protected by a removable protecting group (e.g., an acyl group). Phenolic antioxidants for use in the present invention also generally have a substituent that can react with the pendant reactive group of one of the polymers described above to form a covalent bond between the antioxidant and the polymer.

One group of suitable phenolic antioxidants can be represented by Structural Formula (E):

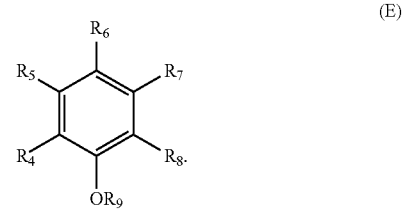

R$_9$ is —H or a substituted or unsubstituted alkyl, acyl or aryl group, preferably —H or an acyl group.

R$_4$, R$_5$, R$_6$, R$_7$ and R$_8$ are independently chosen substituent groups, such that at least one substituent can be a substituted or unsubstituted alkyl or aryl group, a substituted or unsubstituted alkoxycarbonyl group, a substituted or unsubstituted alkylenedioxy group, a 1-propenyl-3-carboxylic acid group or an ester thereof. Also, at least one of R$_4$, R$_5$, R$_6$, R$_7$ and R$_8$ must be a substituent capable of reacting with the pendant reactive group of the polymers described above, such as a substituent having a nucleophilic or electrophilic moiety. Other suitable substituents include, for example, —H, —OH, —NH and —SH. A substituent should not decrease the antioxidant activity more than two-fold; instead, substituents preferably increase the antioxidant activity of the molecule.

Specific examples of phenolic antioxidants that can be attached to a polymer include phenolic antioxidant can be selected from the group consisting of 3-(3,5-di-tert-butyl-4-hydroxyphenyl)propionic acid, 3,5-di-tert-butyl-4-hydroxybenzenethiol, 2-(3,5-di-tert-butyl-4-hydroxyphenyl)acetic acid, 3,5-di-tert-butyl-4-hydroxybenzoic acid, 3,5-di-tert-butyl-4-hydroxycinnamic acid, gallic acid, alkyl gallates, 3,5- di-tert-butyl-4-hydroxybenzyl alcohol, tert-butyl-hydroquinone, 2,5-di-tert-butyl-hydroquinone, 2,6-di-tert-butylhydroquinone, 3,5-di-tert-butyl-4-hydroxybenzaldehyde, monoacetoxy-tert-butylhydroquinone, sesamol, isoflavones, flavanoids and coumarins.

Another antioxidant that can be attached to one of the polymers described immediately above can be ascorbic acid or a molecule that contains an ascorbic acid moiety. Typically, ascorbic acid attached to a polymer has the following configuration:

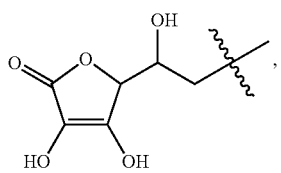

where this moiety can be attached to the polymer by an ether or ester linkage.

Polymers described immediately above which are suitable for use in the compositions and methods of the present invention can be homopolymers or copolymers. One type of copolymer includes ethylene repeat units, particularly in a copolymer containing repeat units represented by Structural Formula (A) and/or Structural Formula (B).

In one embodiment of the invention, a polymer comprises repeat units represented by Structural Formula (A). In a first group of such polymers, the sum of m and p is typically two or greater. When the sum of m and p is greater than two, Z is typically a phenolic antioxidant, as described above. One preferred phenolic antioxidant is a 3,5-di-tert-butyl-4-hydroxyphenyl group, particularly when X is —C(O)—. For these values of X and Z, m is preferably 2 and n and p are each 0. A second preferred antioxidant is a 3,4,5-trihydroxyphenyl group, particularly when X is —C(O)—. Other preferred antioxidants are mono and di-tert-butylated-4-hydroxyphenyl groups, 4-acetoxy-3-tert-butylphenyl groups and 3-alkoxycarbonyl-2,6-dihydroxyphenyl groups (e.g., 3-propoxycarbonyl-2,6-dihydroxyphenyl groups), particularly when X is a covalent bond.

In a second set of these polymer having repeat units represented by Structural Formula (A), m and p are each 0. When m and p are 0, n is also typically 0. For these values of m, n and p, Z is typically ascorbic acid. X is typically a covalent bond. Alternatively, Z is a 3,4,5-trihydroxyphenyl group or a 4-acetoxy-3-tert-butylphenyl group, particularly when X is —C(O)—.

In another embodiment of the invention, an antioxidant polymer has repeat units represented by Structural Formula (B). For these polymers, m, n and p are each typically 0. Z is preferably a phenolic antioxidant, specifically a 3,4,5-trihydroxyphenyl, 3,5-di-tert-butyl-4-hydroxyphenyl group or a 3,5-di-tert-butyl-2-hydroxyphenyl group.

A further embodiment of the invention involves polymers that include repeat units represented by Structural Formula (C). In one group of such polymers, Y is —O— and Z is preferably ascorbic acid, particularly when k is 0. In another group, Y is —O— and Z is a phenolic antioxidant, particularly when k is 0 to 3; more preferably, k is 1. A preferred phenolic antioxidant is a 3,5-di-tert-butyl-4-hydroxyphenol group. Other examples include of phenolic antioxidants include 4-acetoxy-3-tert-butylphenyl, 3-tert-butyl-4-hydroxyphenyl, 2,6-di-tert-butyl-4-mercaptophenyl and 2,6-di-tert-butyl-4-hydroxyphenyl groups.

In yet another embodiment of the invention, a polymer includes repeat units represented by Structural Formula (D). Typically, R' is a covalent bond or —OH in such polymers. Other typical values of R' are amide and ester linkages. Preferred Z groups can be phenolic antioxidants, as described above. For these polymers, the phenol hydroxyl group is typically para or meta to the group containing Z, more typically para.

Antioxidant polymers described immediately above which are suitable for use in the methods of the present invention have two or more repeat units, preferably greater than about five repeat units. The molecular weight of the polymers disclosed herein can be generally selected to be appropriate for the desired application. Typically, the molecular weight can be greater than about 500 atomic mass units (amu) and less than about 2,000,000 amu, greater than about 1000 amu and less than about 1,000,000 amu, greater than about 1000 amu and less than about 100,000 amu, greater than about 2,000 amu and less than about 10,000 amu, or greater than about 2,000 amu and less than about 5,000 amu.

Antioxidant polymers described immediately above which are suitable for use in the methods of the present invention can be typically insoluble in aqueous media. The solubility of the antioxidant polymers in non-aqueous media (e.g., oils) depends upon the molecular weight of the polymer, such that high molecular weight polymers can be typically sparingly soluble in non-aqueous media. When an antioxidant polymer of the invention can be insoluble in a particular medium or substrate, it can be preferably well-mixed with that medium or substrate.

In another embodiment, the antioxidants which are suitable for use in the compositions and methods of the present invention are represented by the following structural formula:

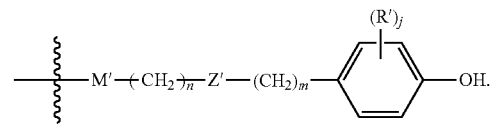

n and m in each occurrence, independently is 0 or a positive integer. Preferably 0 to 18 inclusive.

j in each occurrence, independently is 0, 1, 2, 3 or 4.

Z' in each occurrence, independently is —C(O)O—, —OC(O)—, —C(O)NH—, —NHC(O)—, —NH—, —CH═N—, —N═CH—, —C(O)—, —O—, —S—, —S—S—, —S═N—, —N═S—, —C(S)O—, —OC(S), —OP(O)(OR₄)O—, OP(OR₄)O—, —C(O)OC(O)— or a bond. In one embodiment, Z' is —C(O)O—.

R' in each occurrence, independently is C1-C6 alkyl, —OH, —NH₂, —SH, an optionally substituted aryl, an optionally substituted ester or

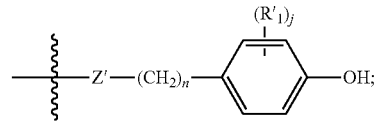

wherein at least one R' adjacent to the —OH group is an optionally substituted bulky alkyl group (e.g., butyl, sec-butyl, tert-butyl, 2-propyl, 1,1-dimethylhexyl, and the like).

$R'_1$ in each occurrence, independently is C1-C6 alkyl, an optionally substituted aryl, an optionally substituted aralkyl, —OH, —NH₂, —SH, or C1-C6 alkyl ester wherein at least one $R_1$ adjacent to the —OH group is a bulky alkyl group (e.g., butyl, sec-butyl, tert-butyl, 2-propyl, 1,1-dimethylhexyl, and the like).).

M' is H, an optionally substituted aryl, C1-C20 linear or branched alkyl chain with or without any functional group anywhere in the chain,

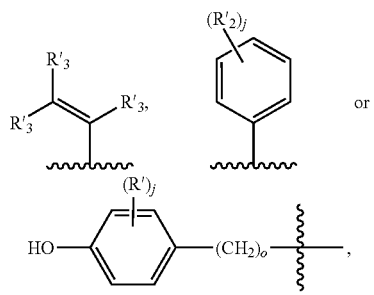

o is 0 or a positive integer, $R'_2$ in each occurrence, independently is —H, C1-C6 alkyl, —OH, —$NH_2$, —SH, optionally substituted aryl, ester, or

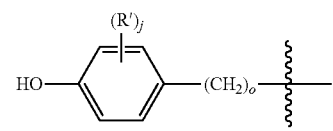

wherein at least one $R'_2$ is —OH.

$R'_3$ in each occurrence, independently is —H, C1-C6 alkyl, optionally substituted aryl, optionally substituted aralkyl —OH, —$NH_2$, —SH or ester.

In another embodiment, the antioxidants which are suitable for use in the compositions and methods of the present invention are represented by the following structural formula:

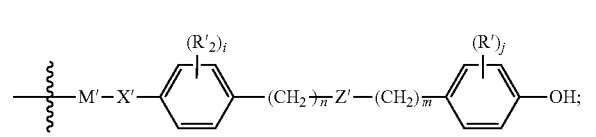

X' in each occurrence, independently is —C(O)O—, —OC(O)—, —C(O)NH—, —NHC(O)—, —NH—, —CH=N—, —C(O)—, —O—, —S—, —C(O)OC(O)— or a bond.

$R'_2$ is C1-C6 alkyl, —OH, —$NH_2$, —SH, aryl, ester, or

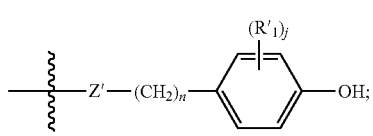

wherein at least one $R'_2$ is —OH, and the values and preferred values for the remainder of the variables are as described immediately above.

In certain embodiments Z' is —C(O)O—. In certain other embodiments Z' is —OC(O)—. In certain embodiments Z' is —C(O)NH—. In certain other embodiments Z' is —NHC(O)—. In certain other embodiments Z' is —NH—. In certain other embodiments Z' is —CH=N—. In certain other embodiments Z' is —N=CH—. In certain other embodiments Z' is —C(O)—. In certain other embodiments Z' is —O—. In certain other embodiments Z' is —S—. In certain other embodiments Z' is —S—S—. In certain other embodiments Z' is —S=N—. In certain other embodiments Z' is —N=S—. In certain other embodiments Z' is —C(S)O—. In certain other embodiments Z' is —OC(S)—. In certain other embodiments Z' is —OP(O)($OR_4$)O—. In certain other embodiments Z' is OP($OR_4$)O—. In certain other embodiments Z' is —C(O)OC(O)—. In certain other embodiments Z' is a bond.

In certain embodiments both R' groups adjacent to the —OH group is an optionally substituted bulky alkyl group. In a particular embodiment both R' groups adjacent to the —OH group are tert-butyl.

In certain embodiments M' is

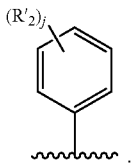

In certain embodiments M' is

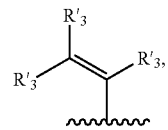

In certain embodiments, at least one R' is

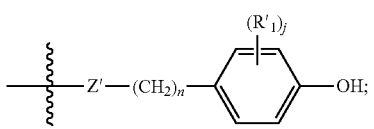

In certain embodiments n is 0.

In certain embodiments m is 1.

In certain embodiments n is 0, m is 1 and Z is —C(O)O—.

In certain embodiments n is 0, m is 1, Z is —C(O)O— and the two R' groups adjacent to the —OH are t-butyl.

In certain embodiments n is 0, m is 1, Z is —C(O)O—, the two R' groups adjacent to the —OH are t-butyl and M' is

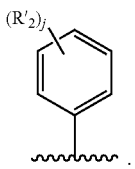

In certain embodiments n is 0, m is 1, Z is —C(O)O—, the two R' groups adjacent to the —OH are t-butyl, M' is

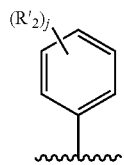

and the R'$_2$ in the para position is —OH.

In certain embodiments n is 0, m is 1, Z is —C(O)O—, the two R' groups adjacent to the —OH are t-butyl, M' is

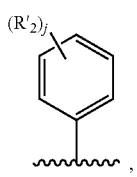, the R'$_2$ in the para position is —OH and an adjacent R'$_2$ is —OH.

In certain embodiments n is 0, m is 1, Z is —C(O)O—, the two R' groups adjacent to the —OH are t-butyl, M' is

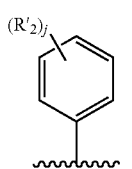, the R'$_2$ in the para position is —OH and the two adjacent R'$_2$ are —OH.

In certain embodiments n is 0, m is 1, Z is —C(O)O—, the two R' groups adjacent to the —OH are t-butyl, M' is

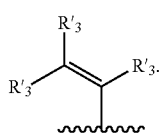

In certain embodiments n is 0, m is 1, Z is —C(O)O—, the two R' groups adjacent to the —OH are t-butyl, M' is

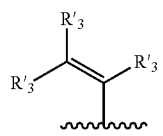

and R$_3$ is —H.

Specific examples of compounds and polymers which are suitable for use in the compositions and methods of the present invention are represented by one of the following structural formulas:

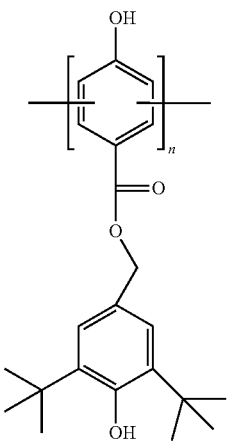
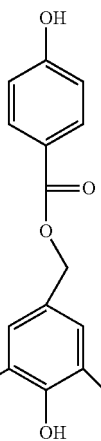

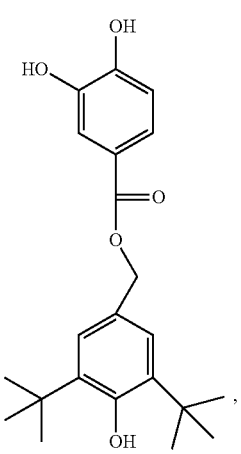
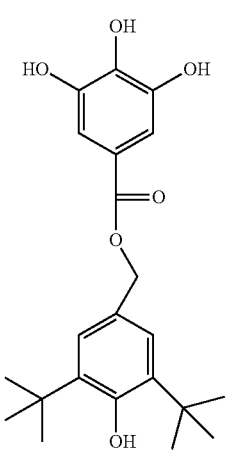

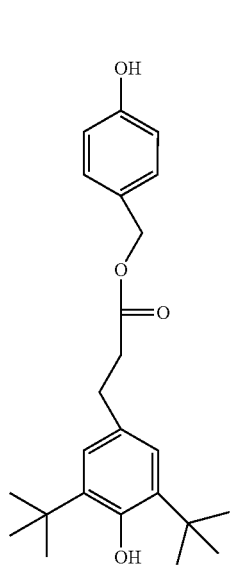
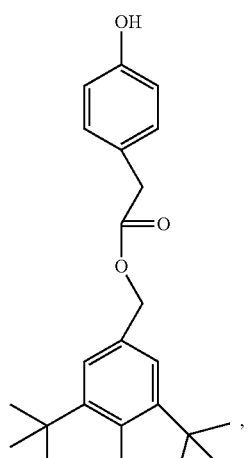

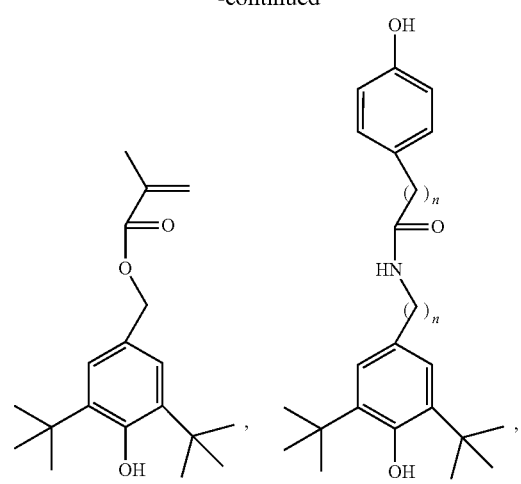

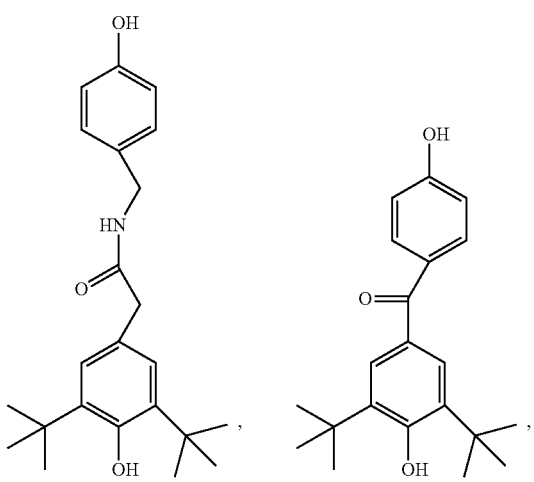

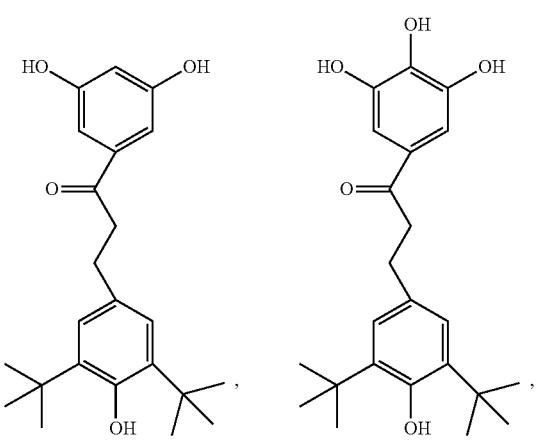

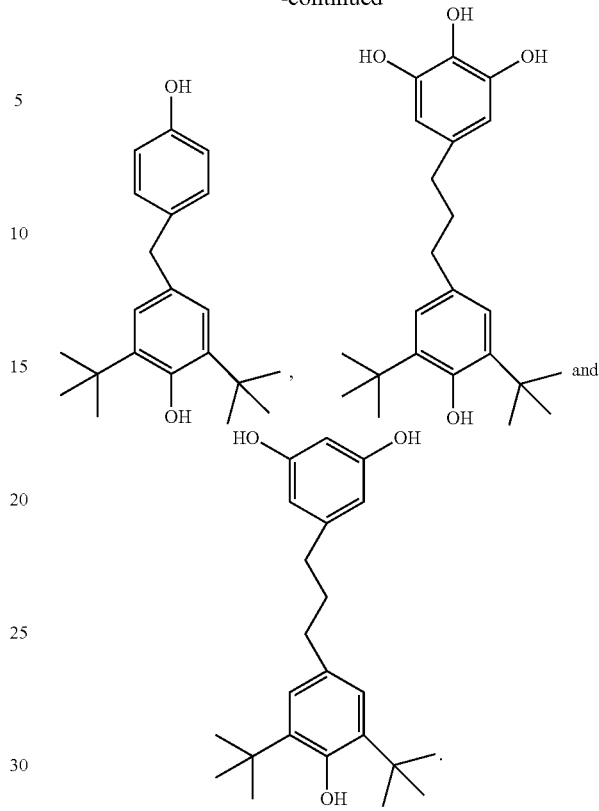

In another embodiment, the antioxidants which are suitable for use in the compositions and methods of the present invention include a macromonomer represented by Structural Formula I.

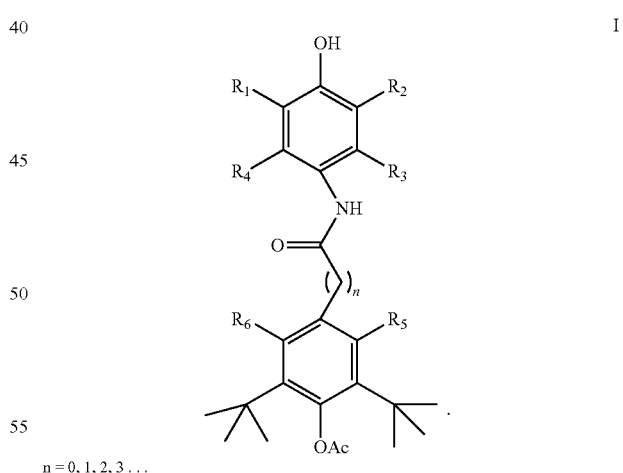

$n = 0, 1, 2, 3 \ldots$

In I, R and $R_1$-$R_6$ are independently —H, —OH, or a C1-C10 optionallyu substituted linear or branched alkyl group. n is an integer from 0 to 24.

In another embodiment, the antioxidants which are suitable for use in the compositions and methods of the present invention include a macromonomer represented by Structural Formula III and an antioxidant polymer represented by Structural Formula IV. The variables are as defined above.

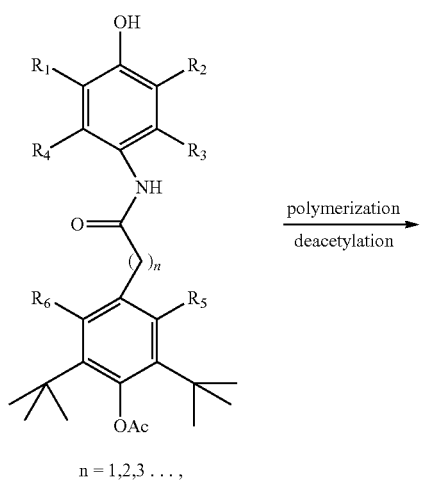

n = 1,2,3 ...,

III

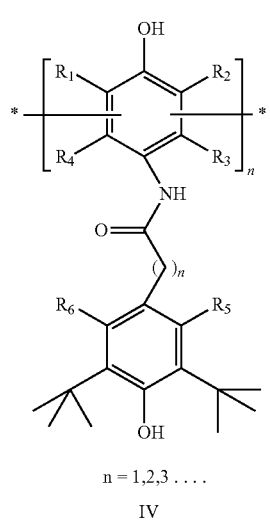

n = 1,2,3 ....

IV

Repeat units of the antioxidant polymers as described immediately above suitable for use in the compositions and methods of the present invention include substituted benzene molecules. These benzenes molecules are typically based on phenol or a phenol derivative, such that they have at least one hydroxyl or ether functional group. Preferably, the benzene molecules have a hydroxyl group. The hydroxyl group can be a free hydroxyl group and can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant polymer can exert its antioxidant effect. The repeat units can also include analogous thiophenol and aniline derivatives, e.g., where the phenol —OH can be replaced by —SH, —NH—, and the like.

Substituted benzene repeat units of an antioxidant polymer as described immediately above suitable for use in the compositions and methods of the present invention are also typically substituted with a bulky alkyl group or an n-alkoxycarbonyl group. Preferably, the benzene monomers are substituted with a bulky alkyl group. More preferably, the bulky alkyl group is located ortho or meta to a hydroxyl group on the benzene ring, typically ortho. A "bulky alkyl group" is defined herein as an alkyl group that is branched alpha- or beta- to the benzene ring. Preferably, the alkyl group is branched alpha to the benzene ring. More preferably, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. The bulky alkyl groups are preferably unsubstituted, but they can be substituted with a functional group that does not interfere with the antioxidant activity of the molecule or the polymer. Straight chained alkoxylcarbonyl groups include methoxycarbonyl, ethoxycarbonyl, n-propoxycarbonyl, n-butoxycarbonyl and n-pentoxycarbonyl, n-propoxycarbonyl is a preferred group. Similar to the bulky alkyl groups, n-alkoxycarbonyl groups are optionally substituted with a functional group that does not interfere with the antioxidant activity of the molecule or the polymer.

Antioxidant polymers as described immediately above suitable for use in the compositions and methods of the present invention have two or more repeat units, preferably greater than about five repeat units. The molecular weight of the polymers disclosed herein can be generally selected to be appropriate for the desired application. Typically, the molecular weight can be greater than about 500 atomic mass units (amu) and less than about 2,000,000 amu, greater than about 1000 amu and less than about 100,000, greater than about 2,000 amu and less than about 10,000, or greater than about 2,000 amu and less than about 5,000 amu.

Antioxidant polymers as described immediately above suitable for use in the compositions and methods of the present invention can be either homopolymers or copolymers. A copolymer preferably contains two or more or three or more different repeating monomer units, each of which has varying or identical antioxidant properties. The identity of the repeat units in a copolymer can be chosen to modify the antioxidant properties of the polymer as a whole, thereby giving a polymer with tunable properties. The second, third and/or further repeat units in a copolymer can be either a synthetic or natural antioxidant.

Antioxidant polymers as described immediately above suitable for use in the compositions and methods of the present invention are typically insoluble in aqueous media. The solubility of the antioxidant polymers in non-aqueous media (e.g., oils) depends upon the molecular weight of the polymer, such that high molecular weight polymers are typically sparingly soluble in non-aqueousu media. When an antioxidant polymer of the invention can be insoluble in a particular medium or substrate, it can be preferably well-mixed with that medium or substrate.

Antioxidant polymers as described immediately above suitable for use in the compositions and methods of the present invention can be branched or linear, but are preferably linear. Branched antioxidant polymers can only be formed from benzene molecules having three or fewer substituents (e.g., three or more hydrogen atoms).

In another embodiment, the antioxidants which are suitable for use in the compositions and methods of the present invention include macromolecule antioxidants represented by Structural Formula J:

J

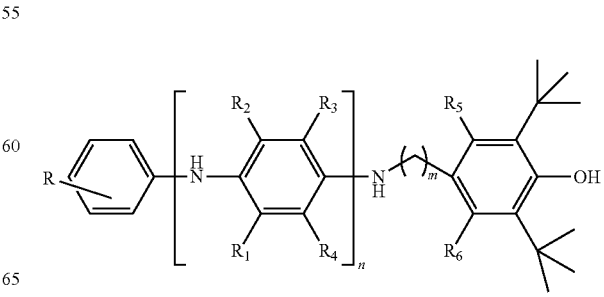

In I, R and $R_1$-$R_6$ are independently —H, —OH, or a C1-$C_{10}$ optionally substituted linear or branched alkyl group. n is an integer from 0 to 24.

Specific examples of macromolecule antioxidants represented by Structural Formula J which are suitable for use in the compositions and methods of the present invention are represented by one of the following structural formulas:

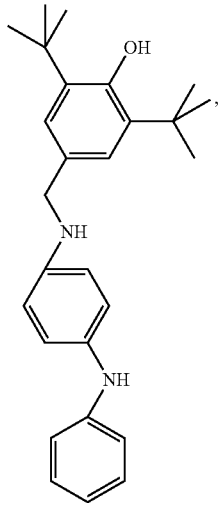 , 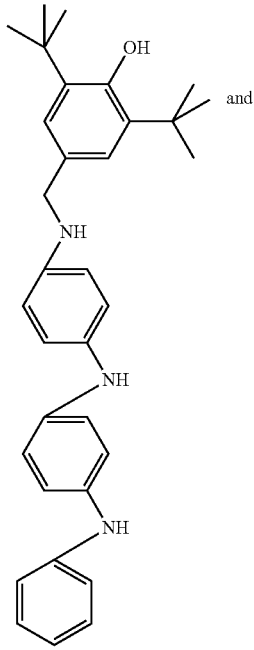 and

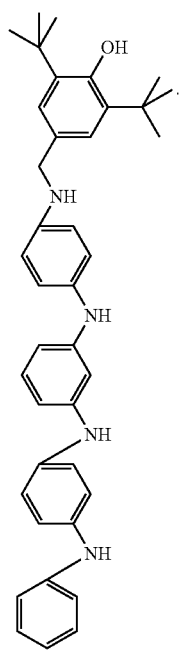

In another embodiment, the antioxidants which are suitable for use in the compositions and methods of the present invention include alkylated antioxidant macromolecules having formula K:

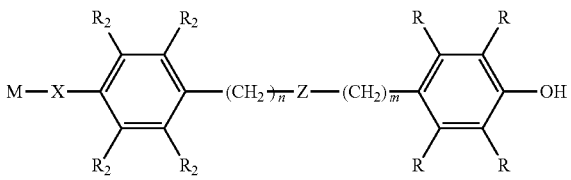

wherein, independently for each occurrence,
n and m are integers from 0 to 6, inclusive;
Z is —C(O)O—, —OC(O)—, —C(O)NH—, —NHC(O)—, —NH—, —CH=N—, —C(O)—, —O—, —S—, —C(O)OC(O)—, or a bond;
R is H, $C_{1-6}$ alkyl, —OH, —NH$_2$, —SH, aryl, aralkyl, or

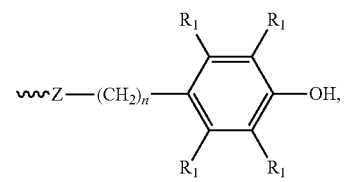

wherein at least one R adjacent to the —OH group is a bulky alkyl group (e.g., butyl, sec-butyl, tert-butyl, 2-propyl, 1,1-dimethylhexyl, and the like);
$R_1$ is H, $C_{1-6}$ alkyl, aryl, alkylaryl, —OH, —NH$_2$, —SH, or C1-C6 alkyl ester wherein at least one $R_1$ adjacent to the —OH group is a bulky alkyl group (e.g., butyl, sec-butyl, tert-butyl, 2-propyl, 1,1-dimethylhexyl, and the like); and
$R_2$ is H, $C_{1-6}$ alkyl, aryl, aralkyl, —OH, —NH$_2$, or —SH wherein at least one $R_1$ adjacent to the —OH group is a bulky alkyl group (e.g., butyl, sec-butyl, tert-butyl, 2-propyl, 1,1-dimethylhexyl, and the like);
X is —C(O)—, —OC(O)—, —C(O)NH—, —NHC(O)—, —NH—, —CH=N—, —C(O)—, —O—, —S—, —C(O)OC(O)—, or a bond;
M is H, aryl, C-1 to C-20 linear or branched alkyl chain with or without any functional group anywhere in the chain, or

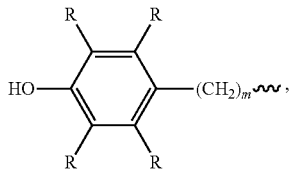

wherein m and each R is independently as described above;
wherein
$R_2$ is H, $C_{1-6}$ alkyl, —OH, —NH$_2$, —SH, aryl, ester, or

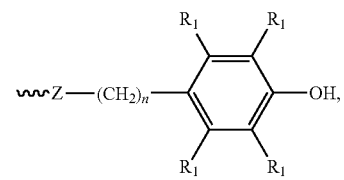

wherein at least one $R_2$ is —OH and n, Z, and each R1 are independently as described above.

In various embodiments, for compounds of formula K, Z is —OC(O)—. In another embodiment, Z is —C(O)O—. In another embodiment, Z is —C(O)NH—. In another embodiment, Z is —NHC(O)—. In another embodiment, Z is —NH—. In another embodiment, Z is —CH═N—. In another embodiment, Z is —C(O)—. In another embodiment, Z is —O—. In another embodiment, Z is —C(O)OC(O)—. In another embodiment, Z is a bond.

In another embodiment, for compounds of formula K, both R groups adjacent to —OH are bulky alkyl groups (e.g., butyl, sec-butyl, tert-butyl, 2-propyl, 1,1-dimethylhexyl, and the like). In another embodiment, both R groups are tert-butyl.

In another embodiment, for compounds of formula K, M is

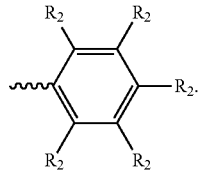

In another embodiment, for compounds of formula K, at least one R is

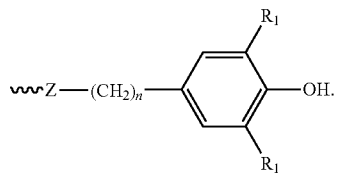

In another embodiment for compounds of formula K, n is 0.

In another embodiment, for compounds of formula K, m is 1.

In another embodiment, for compounds of formula K, n is 0 and m is 1.

In another embodiment, for compounds of formula K, n is 0, m is 1, and Z is —C(O)O—.

In another embodiment, for compounds of formula K, n is 0, m is 1, Z is —C(O)O—, and the two R groups adjacent to the OH are tert-butyl.

In another embodiment, for compounds of formula K, n is 0, m is 1, Z is —C(O)O—, the two R groups adjacent to the OH are t-butyl, and M is

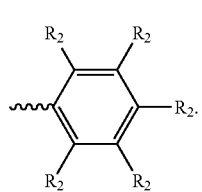

In another embodiment, for compounds of formula K, n is 0, m is 1, Z is —C(O)O—, the two R groups adjacent to the OH are t-butyl, M is

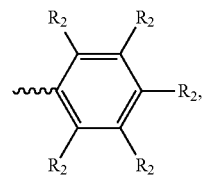

and the $R_2$ in the para position is OH.

In another embodiment, for compounds of formula K, n is 0, m is 1, Z is —C(O)O—, the two R groups adjacent to the OH are t-butyl, M is

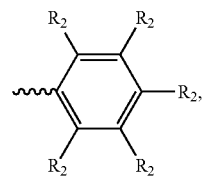

the $R_2$ in the para position is OH, and an adjacent $R_2$ is OH.

In another embodiment, for compounds of formula K, n is 0, m is 1, Z is —C(O)O—, the two R groups adjacent to the OH are t-butyl, M is

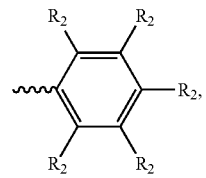

the $R_2$ in the para position is OH, and the two adjacent $R_2$ groups are —OH.

In another embodiment, the antioxidants which are suitable for use in the compositions and methods of the present invention include alkylated antioxidant macromolecules having formula L.

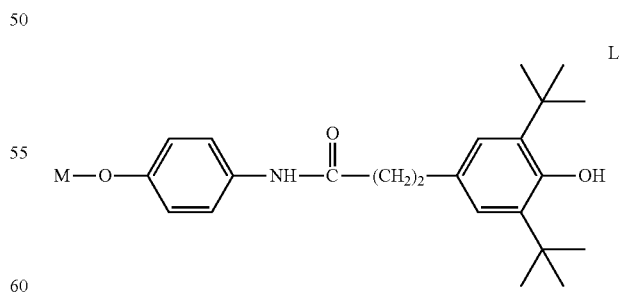

where M is C1 to C20- linear or branched alkyl chains.

In another embodiment the antioxidants which are suitable for use in the compositions and methods of the present invention are alkylated antioxidant macromolecules having formula A:

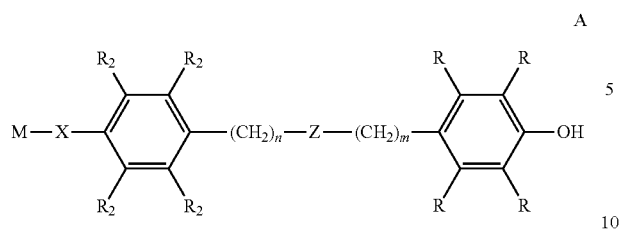

A wherein, independently for each occurrence:

n and m are integers from 0 to 6, inclusive;

Z is —C(O)O—, —OC(O)—, —C(O)NH—, —NHC(O)—, —NH—, —CH=N—, —C(O)—, —O—, —S—, —C(O)OC(O)—, or a bond;

R is H, $C_{1-6}$ alkyl, —OH, —NH$_2$, —SH, aryl, ester, or

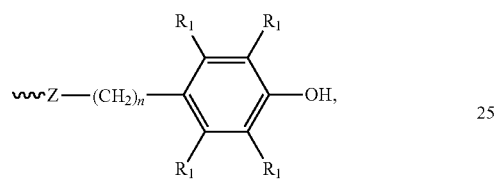

wherein at least one R adjacent to the —OH group is a bulky alkyl group (e.g., butyl, sec-butyl, tert-butyl, 2-propyl, 1,1-dimethylhexyl, and the like);

$R_1$ is H, $C_{1-6}$ alkyl, aryl, aralkyl, —OH, —NH$_2$, —SH, or C1-C6 alkyl ester wherein at least one $R_1$ adjacent to the —OH group is a bulky alkyl group (e.g., butyl, sec-butyl, tert-butyl, 2-propyl, 1,1-dimethylhexyl, and the like); and $R_2$ is H, $C_{1-6}$ alkyl, aralkyl, —OH, —NH$_2$, —SH, or ester, wherein at least one $R_1$ adjacent to the —OH group is a bulky alkyl group (e.g., butyl, sec-butyl, tert-butyl, 2-propyl, 1,1-dimethylhexyl, and the like);

X is —C(O)O—, —OC(O)—, —C(O)NH—, —NHC(O)—, —NH—, —CH=N—, —C(O)—, —O—, —S—, —C(O)OC(O)—, or a bond;

M is H, aryl, C-1 to C-20 linear or branched alkyl chain with or without any functional group anywhere in the chain, or

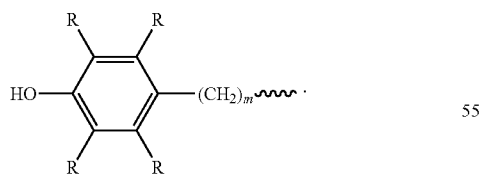

In one embodiment, the antioxidants which are suitable for use in the compositions and methods of the present invention are sterically hindered phenol and phosphite based compounds, represented by a formula selected from I-III;

Specific examples of compounds which are suitable for use in the compositions and methods of the present invention are represented by one of the following structural formulas:

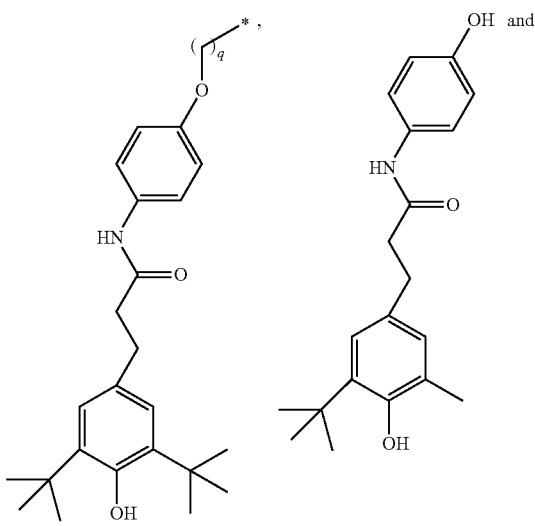

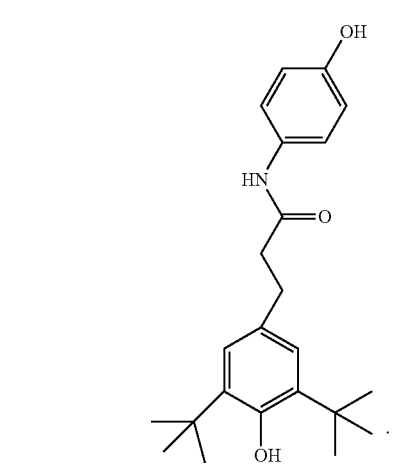

In one embodiment, the antioxidants which are suitable for use in the compositions and methods of the present invention are sterically hindered phenol and phosphate based compounds, represented by a formula selected from O, P and Q.

O

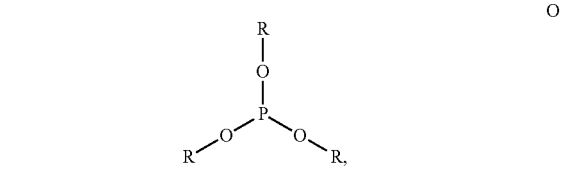

P

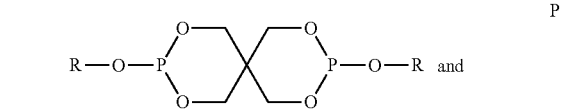 and

Q

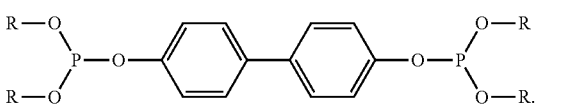

R is:

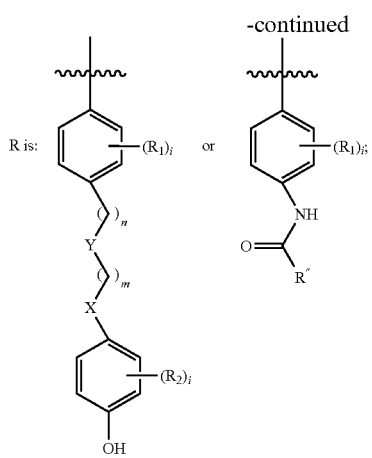

R₁ and R₂ in each occurrence, independently is an optionally substituted alkyl, optionally substituted aryl or optionally substituted aralkyl. In one embodiment, each $R_1$ and $R_2$ are independently an optionally substituted alkyl. In another embodiment, each $R_1$ and $R_2$ are independently a linear or branched C1-C6 alkyl.

In one embodiment R is:

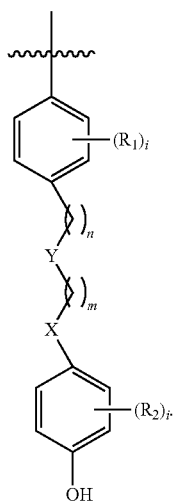

In another embodiment R is:

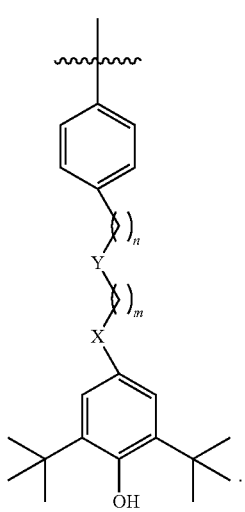

In yet another embodiment R is:

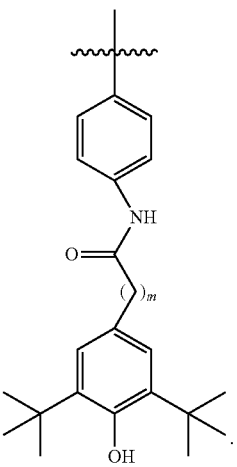

X and Y in each occurrence independently is a bond, —O—, —NH—, —C(O)NH—, —NHC(O)—, —C(O)O—, —OC(O)— or —CH₂—. In one embodiment, X and Y in each occurrence independently is a bond or —CH₂—. In another embodiment, X and Y in each occurrence independently is a bond, —O— or —CH₂—. In yet another embodiment, X and Y in each occurrence independently is a bond, —NH— or —CH₂—. In yet another embodiment, X and Y in each occurrence independently is a bond, —C(O)NH— or —CH₂—. In yet another embodiment, X and Y in each occurrence independently is a bond, —NHC(O)—, or —CH₂—. In yet another embodiment, X and Y in each occurrence independently is a bond, —C(O)O— or —CH₂—. In yet another embodiment, X and Y in each occurrence independently is a bond, —OC(O)— or —CH₂—.

n and m in each occurrence independently is 0 or a positive integer. In one embodiment, n and m in each occurrence independently is 0 to 18. In another embodiment, n and m in each occurrence independently is 0 to 12. In yet another embodiment, n and m are in each occurrence independently is 0 to 6.

i and j in each occurrence independently is 0, 1, 2, 3 or 4. In one embodiment i and j in each occurrence independently is 0, 1 or 2. In a particular embodiment, i is 0. In another particular embodiment j is 2.

R″ is an optionally substituted alkyl. In one embodiment R″ is C1-C6 alkyl.

In a particular embodiment, for compounds represented by structural formulas O, P and Q, R is:

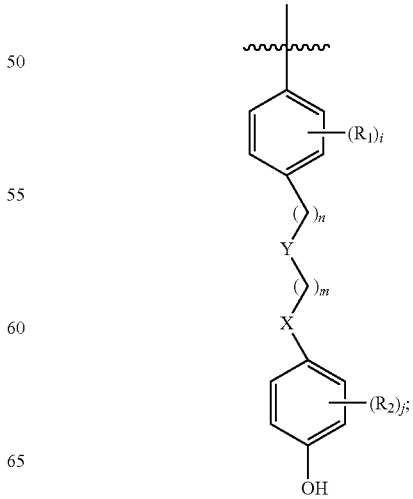

and n and m in each occurrence independently is 0 to 12, and the remainder of the variables are as described above for structural formulas O, P and Q.

In another particular embodiment, for compounds represented by structural formulas O, P and Q, R, n and m are as described immediately above, and $R_1$ and $R_2$ in each occurrence, independently is an optionally substituted alkyl; i and j in each occurrence independently is 0, 1 or 2; and the remainder of the variables are as described above for structural formulas O, P and Q.

In yet another particular embodiment, for compounds represented by structural formulas O, P and Q, $R_1$, $R_2$, i and j are as described immediately above, and R is:

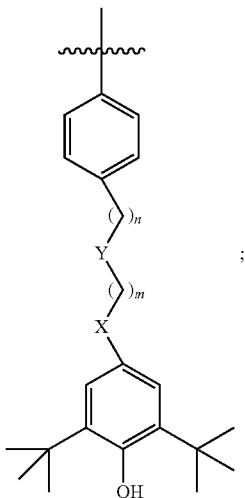

n and m in each occurrence, independently is 0 to 6; and the remainder of the variables are as described above for structural formulas O, P and Q.

In another particular embodiment, for compounds represented by structural formulas O, P and Q, $R_1$, $R_2$, i, j, R, n and m are as described immediately above, and X and Y in each occurrence, independently is bonded or —$CH_2$—; and the remainder of the variables are as described above for structural formulas O, P and Q.

In another particular embodiment, for compounds represented by structural formulas O, P and Q, $R_1$, $R_2$, i, j, R, n and m are as described immediately above, and X and Y in each occurrence, independently is a bond, —O— or —$CH_2$—; and the remainder of the variables are as described above for structural formulas O, P and Q.

In another particular embodiment, for compounds represented by structural formulas O, P and Q, $R_1$, $R_2$, i, j, R, n and m are as described immediately above, and X and Y in each occurrence, independently is a bond, —NH— or —$CH_2$—; and the remainder of the variables are as described above for structural formulas O, P and Q.

In another particular embodiment, for compounds represented by structural formulas O, P and Q, $R_1$, $R_2$, i, j, R, n and m are as described immediately above, and X and Y in each occurrence, independently is a bond, —C(O)NH— or —$CH_2$—; and the remainder of the variables are as described above for structural formulas O, P and Q.

In another particular embodiment, for compounds represented by structural formulas O, P and Q, $R_1$, $R_2$, i, j, R, n and m are as described immediately above, and X and Y in each occurrence, independently is a bond, —NHC(O)— or —$CH_2$—; and the remainder of the variables are as described above for structural formulas O, P and Q.

In another particular embodiment, for compounds of the present invention represented by structural formulas O, P and Q, $R_1$, $R_2$, i, j, R, n and m are as described immediately above, and X and Y in each occurrence, independently is a bond, —C(O)O— or —$CH_2$—; and the remainder of the variables are as described above for structural formulas O, P and Q.

In another particular embodiment, for compounds of the present invention represented by structural formulas O, P and Q, $R_1$, $R_2$, i, j, R, n and m are as described immediately above, and X and Y in each occurrence, independently is a bond, —OC(O)— or —$CH_2$—; and the remainder of the variables are as described above for structural formulas O, P and Q.

In an additional embodiment, for formulas O, P and Q R is:

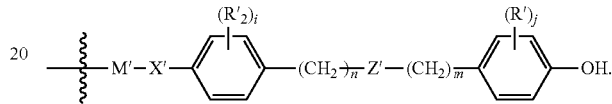

n and m in each occurrence, independently is 0 or a positive integer. In one embodiment, n and m in each occurrence, independently is 0 to 18. In another embodiment, n and m in each occurrence, independently is 0 to 12. In yet another embodiment, n and m in each occurrence, independently is 0 to 6.

i and j in each occurrence, independently is 0, 1, 2, 3 or 4. In one embodiment, i and j in each occurrence, independently is 0, 1 or 2. In a particular embodiment, i is 0. In another particular embodiment, j is 2.

Z' is —C(O)O—, —OC(O)—, —C(O)NH—, —NHC(O)—, —NH—, —CH=N—, —C(O)—, —O—, —S—, —C(O)OC(O)— or a bond. In one embodiment, Z' is —C(O)O—. In another embodiment, Z' is —OC(O)—. In yet another embodiment, Z' is —C(O)NH—. In yet another embodiment, Z' is —NHC(O)—. In yet another embodiment, Z' is —NH—. In yet another embodiment, Z' is —CH=N—. In yet another embodiment, Z' is —C(O)—. In yet another embodiment, Z' is —O—. In yet another embodiment, Z' is —S—. In yet another embodiment, Z' is —C(O)OC(O)—. In yet another embodiment, Z' is a bond.

R' is an optionally substituted C1-C6 alkyl, —OH, —$NH_2$, —SH, an optionally substituted aryl, an ester or

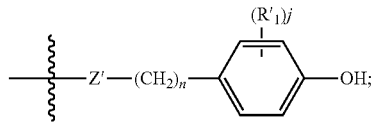

wherein at least one R' adjacent to the —OH group is an optionally substituted bulky alkyl group (e.g., butyl, sec-butyl, tert-butyl, 2-propyl, 1,1-dimethylhexyl, and the like).

$R'_1$ is an optionally substituted C1-C6 alkyl, an optionally substituted aryl, an optionally substituted aralkyl, —OH, —$NH_2$, —SH, or C1-C6 alkyl ester wherein at least one $R_1$ adjacent to the —OH group is a bulky alkyl group (e.g., butyl, sec-butyl, tert-butyl, 2-propyl, 1,1-dimethylhexyl, and the like).).

$R'_2$ is an optionally substituted C1-C6 alkyl, an optionally substituted aryl, an optionally substituted aralkyl, —OH, —$NH_2$, —SH, or ester.

X' is —C(O)O—, —OC(O)—, —C(O)NH—, —NHC(O)—, —NH—, —CH=N—, —C(O)—, —O—, —S—, —C(O)OC(O)— or a bond. In one embodiment X' is —C(O)O—. In another embodiment X' is —OC(O)—. In yet another embodiment X' is —C(O)NH—. In yet another embodiment X' is —NHC(O)—. In yet another embodiment X' is —NH—. In yet another embodiment X' is —CH=N—. In yet another embodiment X' is —C(O)—. In yet another embodiment X' is —O—. In yet another embodiment X' is —S—. In yet another embodiment X' is —C(O)OC(O)—. In yet another embodiment X' is a bond.

M' is H, an optionally substituted aryl, an optionally substituted C1-C20 linear or branched alkyl chain with or without any functional group anywhere in the chain, or

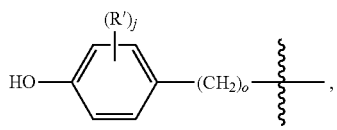

o is 0 or a positive integer. Preferably o is 0 to 18. More preferably o is 0 to 12. Even more preferably o is 0 to 6.

In yet another embodiment, for formulas O, P and Q R is:

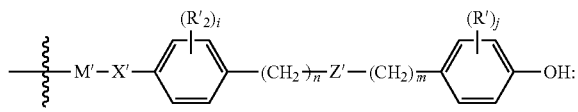

R'$_2$ is C1-C6 alkyl, —OH, —NH$_2$, —SH, aryl, ester, aralkyl or

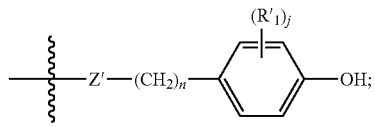

wherein at least one R'$_2$ is —OH, and the values and preferred values for the remainder of the variables for R are as described immediately above.

In yet another embodiment, the present invention relates to a compound of formula O, P and Q, wherein M is

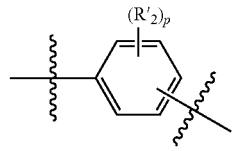

Wherein p is 0, 1, 2, 3 or 4; and the values and preferred values for the remainder of the variables are as described above for formulas O, P and Q.

Specific examples of compounds which are suitable for use in the compositions and methods of the present invention are represented by one of the following structural formulas:

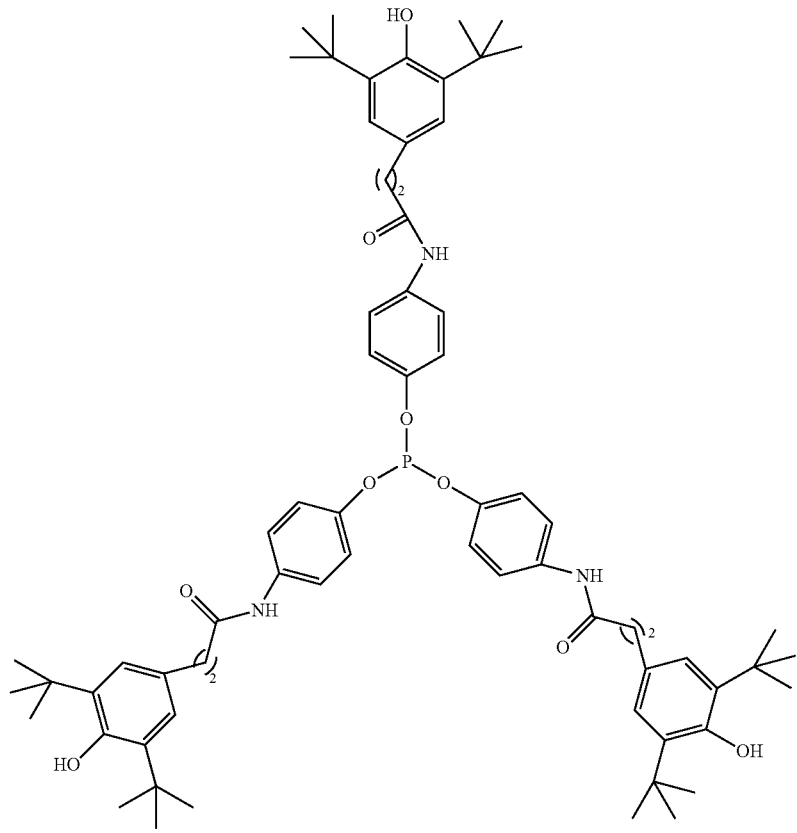

and

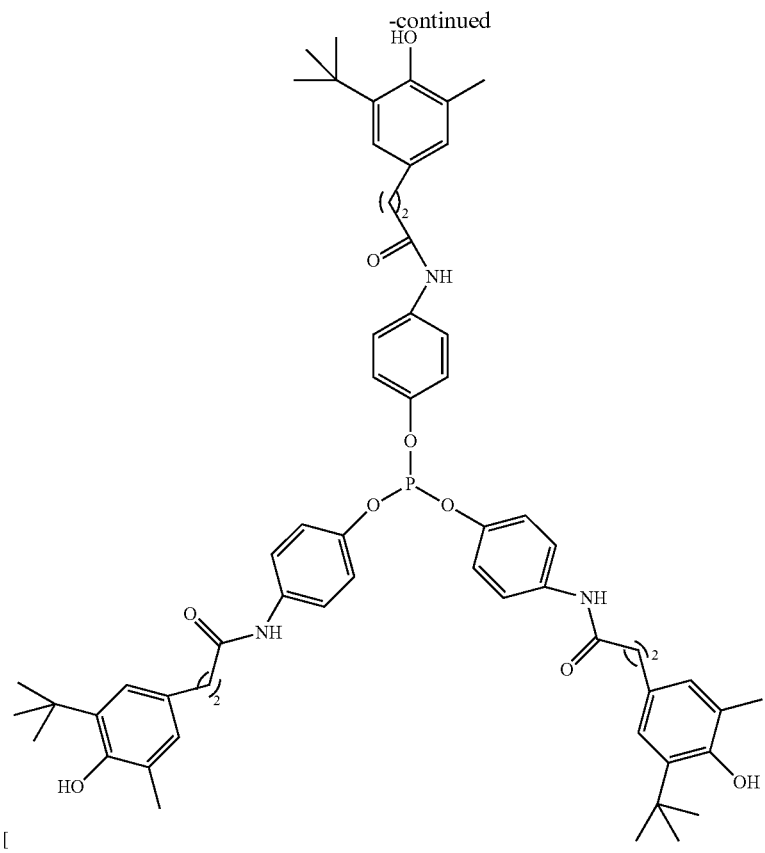

In another embodiment, the antioxidants which are suitable for use in the compositions and methods of the present invention are represented by a structural formula selected from 1-6:

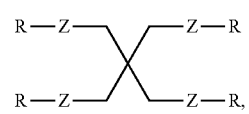

1

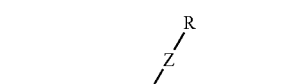

2

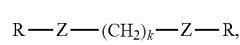

R—Z—(CH$_2$)$_k$—Z—R,

3

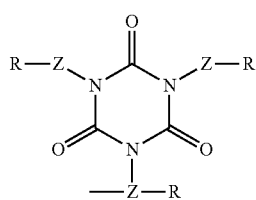

4

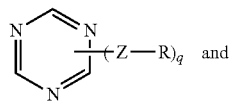

5

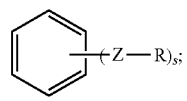

6

R is:

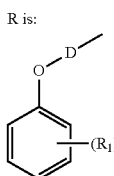

A in each occurrence, independently is a bond, —O—, —NH—, —S—, —C(O)—, —C(O)NH—, —NHC(O)—, —C(O)O—, —OC(O)—, —CH=N— or —N=CH—. In certain particular embodiments, A in each occurrence, independently is —C(O)NH— or —NHC(O)—.

B in each occurrence, independently is a bond or an optionally substituted alkylene group. In certain particular embodiments B is a C1-C6 alkyl.

C in each occurrence, independently is —H, an optionally substituted alkyl group

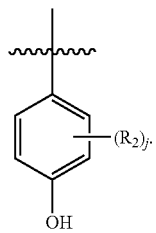

In a particular embodiment, C is:

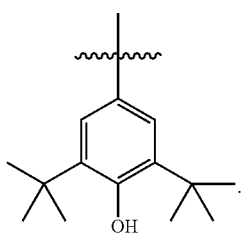

In a particular embodiment R is:

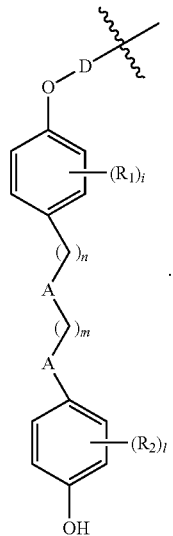

In another particular embodiment R is:

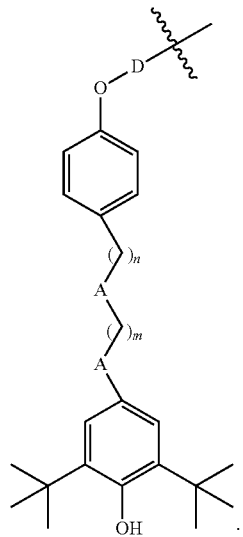

In yet another particular embodiment R is:

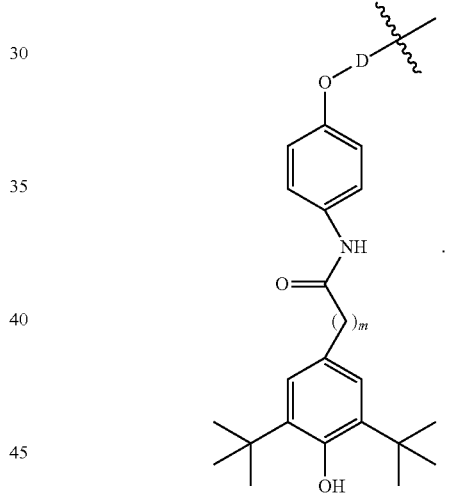

$R_1$ and $R_2$ in each occurrence, independently is an optionally substituted alkyl, optionally substituted aryl or optionally substituted aralkyl. In one embodiment, each $R_1$ and $R_2$ in each occurrence, independentlyl is an optionally substituted alkyl. In another embodiment, each $R_1$ and $R_2$ in each occurrence, independently is a C1-C6 alkyl.

D in each occurrence, independently is a bond, an optionally substituted alkylene group, —$(CH_2)_1C(O)O(CH_2)_1$—, —$(CH_2)_1NHC(O)(CH_2)_1$—, —$(CH_2)_1C(O)NH(CH_2)_1$—, —$(CH_2)_1C(O)O(CH_2)_1$—, —$(CH_2)_1OC(O)(CH_2)_1$—, —$(CH_2)_1CH=N(CH_2)_1$—, —$(CH_2)_1N=CH(CH_2)_1$—, —$(CH_2)_1NH(CH_2)_1$—, —$(CH_2)_1S-(CH_2)_1$—, —$(CH_2)_1O(CH_2)_1$— or —$(CH_2)_1C(O)(CH_2)_1$—.

Z in each occurrence, independently is a bond, an optionally substituted alkylene group, —S—, —O— or —NH—.

i and j in each occurrence, independently is 0, 1, 2, 3 or 4. In one embodiment i and j in each occurrence, independently is 0, 1 or 2. In a particular embodiment i is 0. In another particular embodiment, j is 2.

k is a positive integer from 1 to 20. In one embodiment, k is a positive integer from 1 to 12. In another embodiment, k is a positive integer from 1 to 6.

l is 0 or a positive integer from 1 to 20. In one embodiment, l is 0 or a positive integer from 1 to 12. In another embodiment, l is 0 or a positive integer from 1 to 6.

n and m in each occurrence independently is 0 or a positive integer. In one embodiment, n and m in each occurrence independently is 0 to 18. In another embodiment, n and m in each occurrence independently is 0 to 12. In yet another embodiment, n and m are in each occurrence independently is 0 to 6.

s is a positive integer from 1 to 6.

q is a positive integer from 1 to 3.

In certain other embodiments R is:

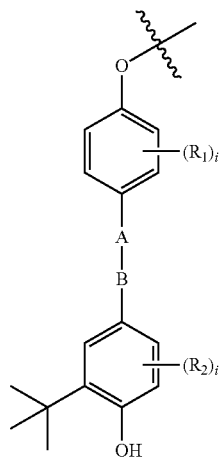

$R_1$ and $R_2$ in each occurrence, independently is —H, —OH, a C1-C10 alkyl group or a tert-butyl group; A is —NHC(O)— or —C(O)O— and B is a bond or a C1-C24 alkylene, and i and j are 0, 1, 2, 3 or 4.

In an additional embodiment, for formulas 1-6 R is:

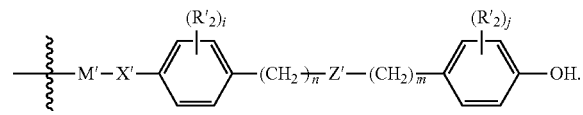

n and m in each occurrence, independently is 0 or a positive integer. In one embodiment, n and m in each occurrence, independently is 0 to 18. In another embodiment, n and m in each occurrence, independently is 0 to 12. In yet another embodiment, n and m in each occurrence, independently is 0 to 6.

i and j in each occurrence, independently is 0, 1, 2, 3 or 4. In one embodiment, i and j in each occurrence, independently is 0, 1 or 2. In a particular embodiment, i is 0. In another particular embodiment, j is 2.

Z' in each occurrence, independently is —C(O)O—, —OC(O)—, —C(O)NH—, —NHC(O)—, —NH—, —CH=N—, —C(O)—, —O—, —S—, —C(O)OC(O)— or a bond. In one embodiment, Z' is —C(O)O—. In another embodiment, Z' is —OC(O)—. In yet another embodiment, Z' is —C(O)NH—. In yet another embodiment, Z' is —NHC(O)—. In yet another embodiment, Z' is —NH—. In yet another embodiment, Z' is —CH=N—. In yet another embodiment, Z' is —C(O)—. In yet another embodiment, Z' is —O—. In yet another embodiment, Z' is —S—. In yet another embodiment, Z' is —C(O)OC(O)—. In yet another embodiment, Z' is a bond.

R' in each occurrence, independently is C1-C6 alkyl, —OH, —NH$_2$, —SH, an optionally substituted aryl, an ester or

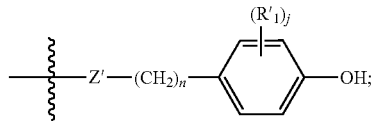

wherein at least one R' adjacent to the —OH group is an optionally substituted bulky alkyl group (e.g., butyl, sec-butyl, tert-butyl, 2-propyl, 1,1-dimethylhexyl, and the like).

$R'_1$ is each occurrence, independently is C1-C6 alkyl, an optionally substituted aryl, an optionally substituted aralkyl, —OH, —NH$_2$, —SH, or C1-C6 alkyl ester wherein at least one $R_1$ adjacent to the —OH group is a bulky alkyl group (e.g., butyl, sec-butyl, tert-butyl, 2-propyl, 1,1-dimethylhexyl, and the like).).

$R'_2$ in each occurrence, independently is C1-C6 alkyl, an optionally substituted aryl, an optionally substituted aralkyl, —OH, —NH$_2$, —SH, or ester.

X' in each occurrence, independently is —C(O)O—, —OC(O)—, —C(O)NH—, —NHC(O)—, —NH—, —CH=N—, —C(O)—, —O—, —S—, —C(O)OC(O)— or a bond. In one embodiment X' is —C(O)O—. In another embodiment X' is —OC(O)—. In yet another embodiment X' is —C(O)NH—. In yet another embodiment X' is —NHC(O)—. In yet another embodiment X' is —NH—. In yet another embodiment X' is —CH=N—. In yet another embodiment X' is —C(O)—. In yet another embodiment X' is —O—. In yet another embodiment X' is —S—. In yet another embodiment X' is —C(O)OC(O)—. In yet another embodiment X' is a bond.

M' is H, an optionally substituted aryl, C1-C20 linear or branched alkyl chain with or without any functional group anywhere in the chain, or

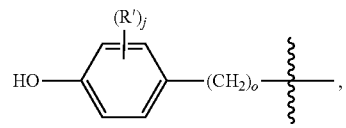

o is 0 or a positive integer. Preferably o is 0 to 18. More preferably o is 0 to 12. Even more preferably o is 0 to 6.

In yet another embodiment, for formulas 1-6 R is:

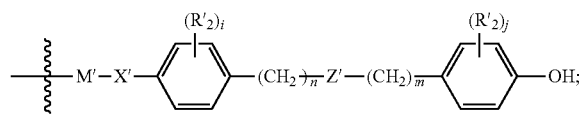

R'₂ is C1-C6 alkyl, —OH, —NH₂, —SH, aryl, aralkyl, ester, or

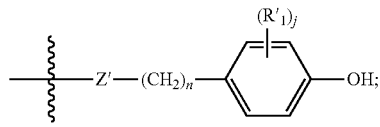

wherein at least one R'₂ is —OH, and the values and preferred values for the remainder of the variables for R are as described immediately above.

In yet another embodiment, the present invention relates to a compound of formula 1-6, wherein M is

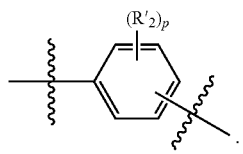

Wherein p is 0, 1, 2, 3 or 4; and the values and preferred values for the remainder of the variables are as described above for formulas 1-6.

Specific examples of macromolecular antioxidants which are suitable for use in the compositions and methods of the present invention, for example, high molecular weight dimers, and tetramers etc., are shown below.

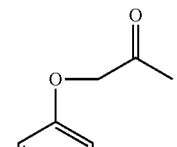

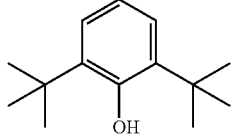

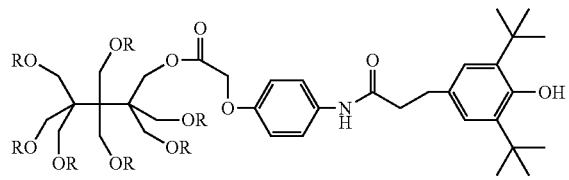

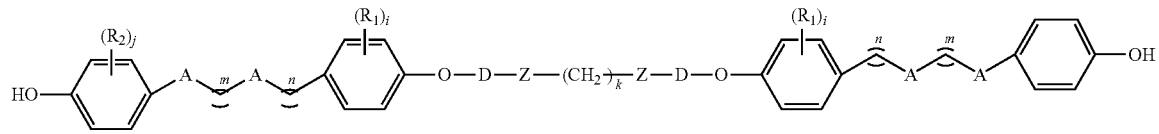

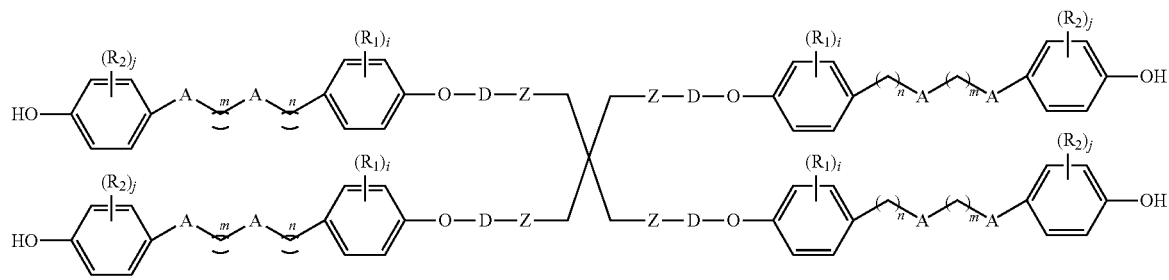

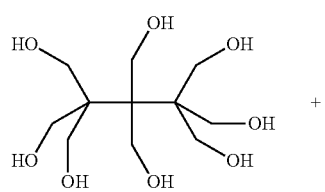

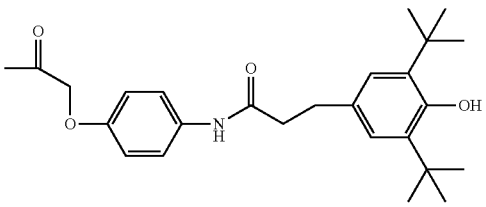

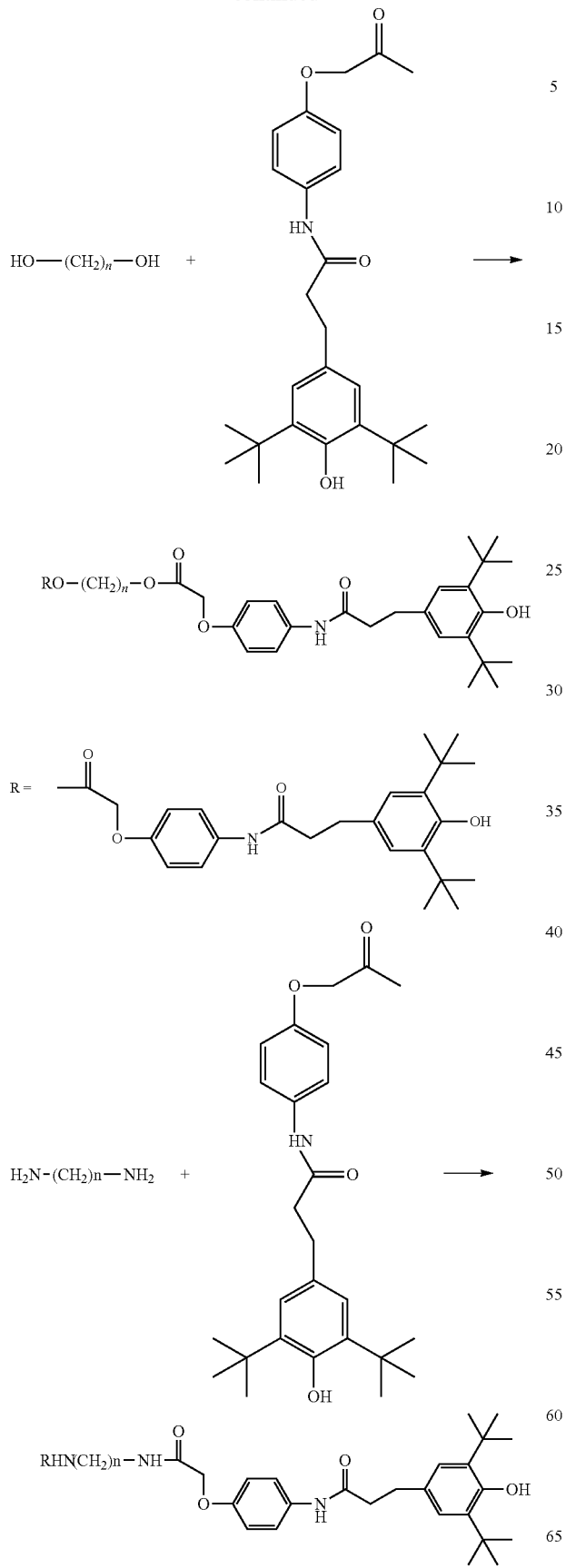
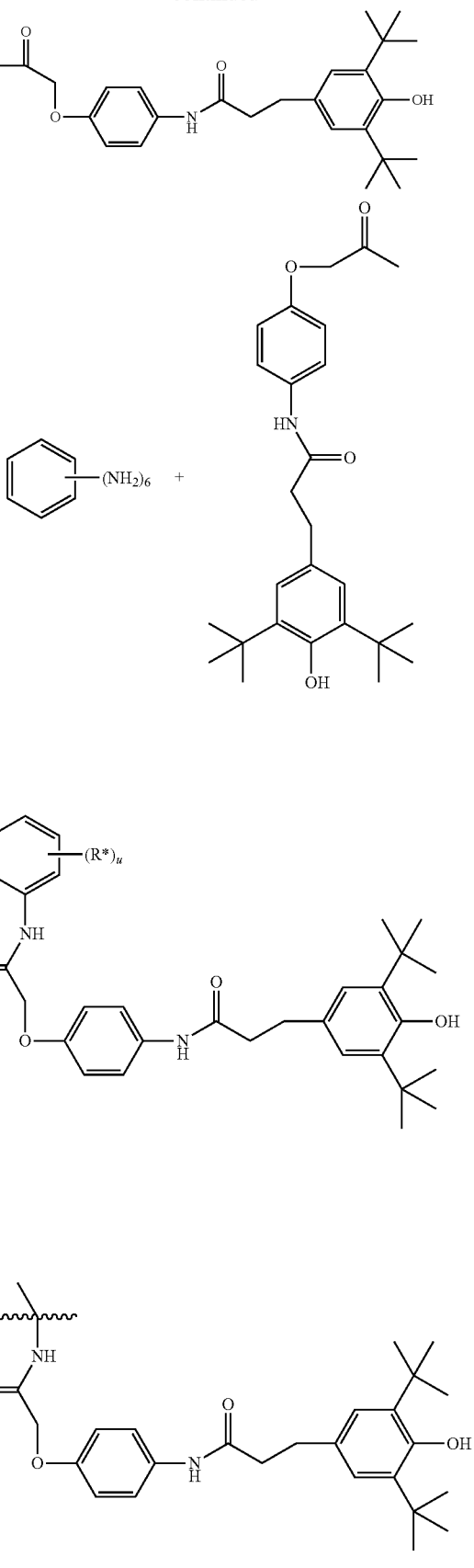

-continued

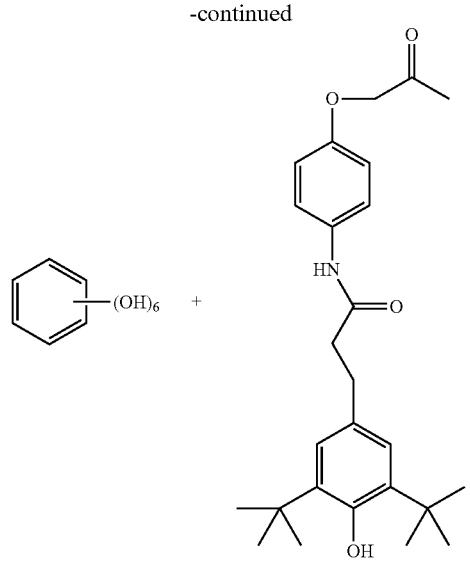

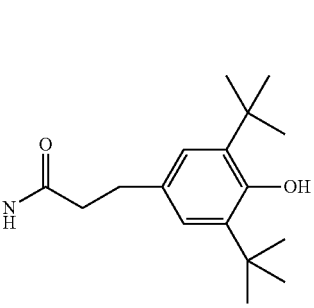

u is 1, 2, 3, 4 or 5

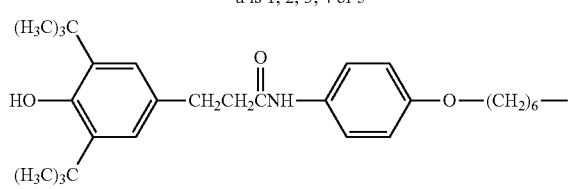

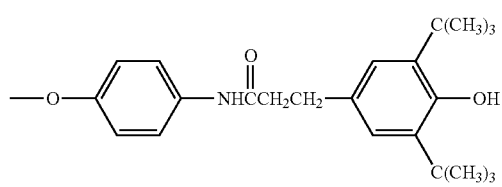

The values and preferred values for the variables are as described above.

In another embodiment, the antioxidants which are suitable for use in the compositions and methods of the present invention are represented by a structural formula selected from 7a, 7b, 8a and 8b:

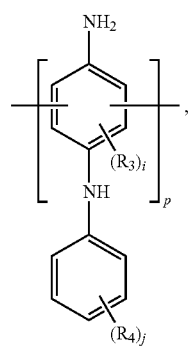
7a

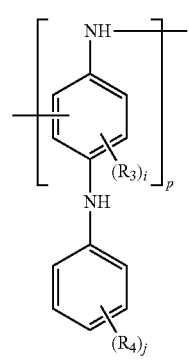
7b

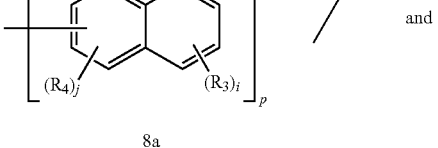
and
8a

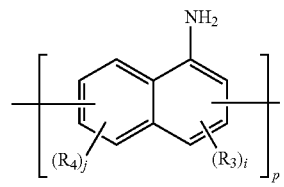
8b $R_3$ and $R_4$ in each occurrence, independently is C1-C16 alkyl, —O—(C1-C16 alkyl), —NH(aryl), —NH$_2$, —OH, or —SH.

p in each occurrence, independently is an integer equal to or greater than 2.

Specific examples of polymers which are useful in the compositions methods of the present invention include:

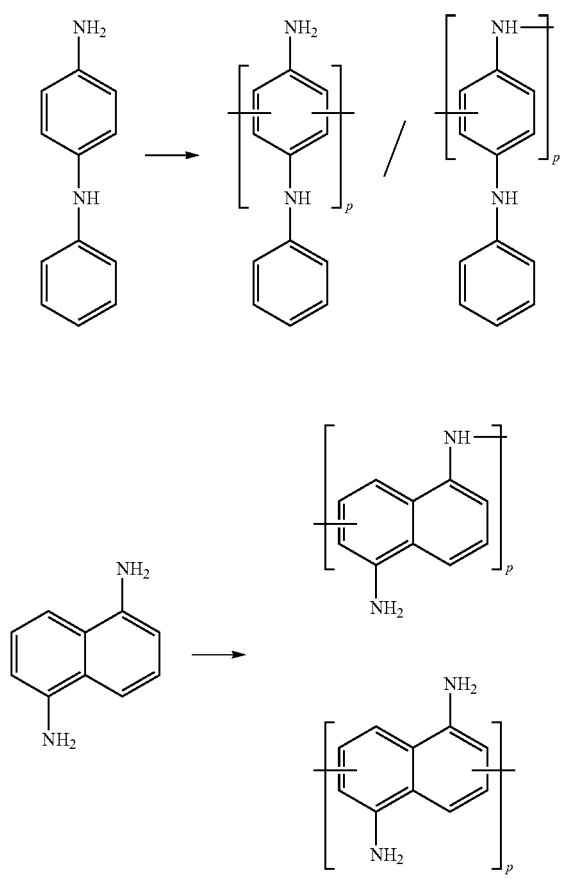

In one embodiment, of the present invention the compositions for use in stabilization of polyolefins, include but are not limited to:

a. an antioxidant (in the concentration range, from about 0.0001% to about 50%, from about 0.0005% to about 20%, from about 0.005% to about 10%, from about 0.05% to about 5% or from about 0.01% to about 1%) with acid scavengers, for example, in amounts of from about 0.0005% to about 50%, from about 0.0001% to about 20%, from about 0.005% to about 10%, from about 0.05% to about 5% or from about 0.01% to about 1% by weight, based on the weight of polyolefin to be stabilized.

b. an antioxidant (in the concentration range from about 0.0005% to about 50%, from about 0.0001% to about 20%, from about 0.005% to about 10%, from about 0.05% to about 5% or from about 0.01% to about 1%) along with organic phosphorus stabilizers. The organic phosphorus stabilizers are used for example, in amounts of, from about 0.001% to about 30%, from about 0.005% to about 20%, from about 0.01% to about 5%, from about 0.05% to about 2% or from about 0.1% to about 1%, by weight, based on the weight of the polyolefin to be stabilized.

c. an antioxidant (in the concentration range from about 0.0005% to about 50%, from about 0.0001% to about 50%, from about 0.005% to about 10%, from about 0.05% to about 5% or from about 0.01% to about 1%) along with acid scavengers and organic phosphorus stabilizers in concentrations described in a. and b. above.

d. an antioxidant in combination with other known commercially available antioxidants, such as, for example, Irganox® 1010, Irganox® 1330, Irganox® 1076 and Irganox® 1135 or other antioxidants described above or incorporated herein by reference along with the formulations described in a.-c. above.

POLYOLEFINS

In certain embodiments of the present invention, polyolefins and mixtures of polyolefins can be stabilized by contacting the polyolefin or mixture of polyolefins with a composition of the present invention. These polyolefins and mixtures of polyolefins, include, but are not limited to substituted polyolefins, polyacrylates, polymethacrylates and copolymers of polyolefins. The following are examples of some types of polyolefins which can be stabilized by the methods of the present invention:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polyethylene (VLDPE) and ultra low density polyethylene (ULDPE).

Polyolefins, i.e. the polymers of monoolefins exemplified in the preceding paragraph, for example polyethylene and polypropylene, can be prepared by different, and especially by the following, methods:

i) radical polymerization (normally under high pressure and at elevated temperature).

ii) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usally termed Phillips, Standard Oil Indiana, Ziegler (-Natta), TNZ (DuPont), metallocene or single site catalysts (SSC).

2. Mixtures of the polymers mentioned under 1., for example, mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Blends of polymers mentioned under 1, with impact modifiers such as ethylene-propylene-diene monomer copolymers (EPDM), copolymers of ethylene with higher alpha-olefins (such as ethylene-octene copolymers), polybutadiene, polyisoprene, styrene-butadiene copolymers, hydrogenated styrene-butadiene copolymers, styrene-isoprene copolymers, hydrogenated styrene-isoprene copolymers. These blends are commonly referred to in the industry as TPO's (thermoplastic polyolefins).

In certain particular embodiments polyolefins of the present invention are for example polypropylene homo- and copolymers and polyethylene homo- and copolymers. For instance, polypropylene, high density polyethylene (HDPE), linear low density polyethylene (LLDPE) and polypropylene random and impact (heterophasic) copolymers.

STABILIZERS
ACID SCAVENGERS OR ACID STABILIZERS

"Acid scvaangers or stabilizers" are defined herein as antacids or co-stabilizers which neutralize the acidic catalysts or other components present in the polymers.

In certain embodiments, of the present invention the acid scavengers which are suitable for use in the methods of the present invention include but are not limited to: zinc oxide, calcium lactate, natural and synthetic hydrotalcites, natural and synthetic hydrocalumites, and alkali metal salts and alkaline earth metal salts of higher fatty acids for example calcium stearate, zinc stearate, magnesium behenate, magnesium stearate, sodium stearate, sodium ricinoleate and potassium palmitate, antimony pyrocatecholate and zinc pyrocatecholate. Combinations of acid scavengers may also be employed.

In certain particular embodiments, the acid scavengers are used for example, in amounts of from about 0.0005% to about 50% by weight, about 0.0001% to about 20% by weight, about 0.005% to about 5% by weight, about 0.01% to about 3% by weight, about 0.05% to about 2% by weight, or about 0.1% to about 1% by weight, based on the weight of polyolefin to be stabilized.

ORGANIC PHOSPHORUS STABILIZERS

In certain embodiments of the present invention, examples of organic phosphorus stabilizers (or phosphorus stabilizers) include phosphates, phosphites and phosphonites which are suitable for use in the methods of the present invention. Specific examples of phosphorus stabilizers include but are not limited to: triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, ethanamine, 2-[[2,4,8,10-tetrakis(1,1dimethylethyl)dibenzo[d,f][1,2,3]dioxaphosphepin-6-yl]oxy]-N,N-[bis[2-[[2,4,8,10-tetrakis(1,1diemthylethyl)dibenzo[d,f][1,2,3]dioxaphepin-6-yl]oxy]ethyl] (represented by structural formula (B) diisodecyl pentaerythritol diphosphite, bis(2,4-di-tert-butylphenyl) pentaerythritol diphosphite (represented by structural formula (D) below), bis(2,6-di-tert-butyl-4-methylphenyl) pentaerythritol diphosphite (represented by structural formula (E) below), 3,9-bis(octadecylpxy)-2,4,8,10-tetraoxa-3,9-diphosphaspiro[5,5undecane (represented by structural formula (F), bisisodecyloxypentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis (2,4-di-tert-butylphenyl) 4,4'-biphenylenediphosphonite (represented by structural formula (H) below, 6-isooctyloxy-2,4,8,10-tetra-tert-butyl-dibenzo[d,f][1,3,2] dioxaphosphepin (represented by structural formula (C) below), 6-fluoro-2,4,8,10-tetra-tert-butyl-12-methyl-dibenzo[d,g][1,3,2]dioxaphosphocin (represented by structural formula (A) below), bis(2,4-di-tert-butyl-6-methylphenyl) methyl phosphite, bis(2,4-di-tert-butyl-6-methylphenyl) ethyl phosphite (represented by structural formula (G) below), (2,4,6-tri-tert-butylphenyl) 2-butyl-2-ethyl-1,3-propanediol phosphate (represented by structural formula (J) below), bis(2,4-di-cumylphenyl) pentaerythritol diphosphite (represented by structural formula (K) below), and structural formula (L) below:

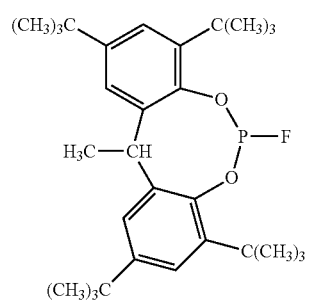

(A)

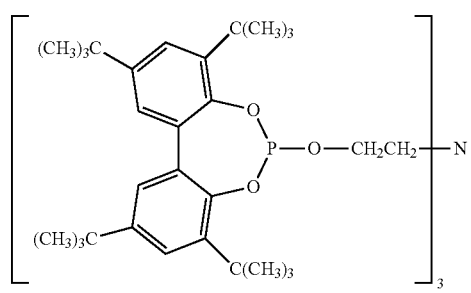

(B)

-continued
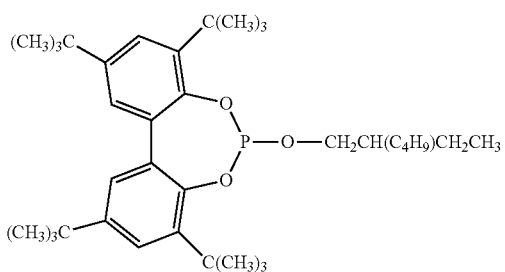
(C)
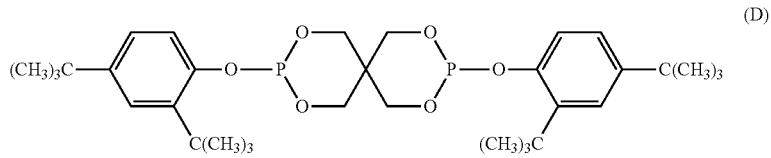
(D)
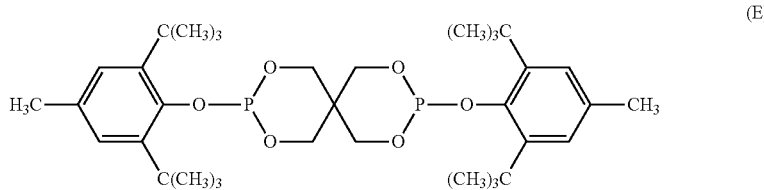
(E)
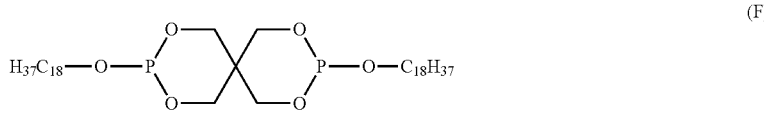
(F)
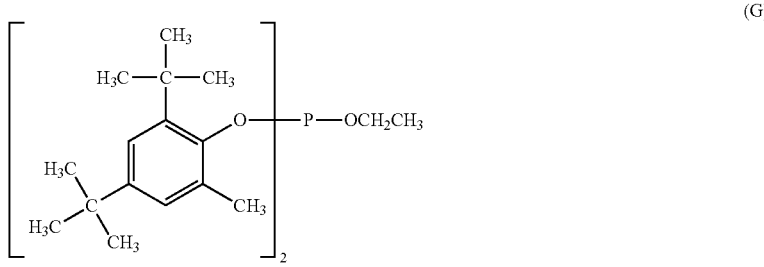
(G)
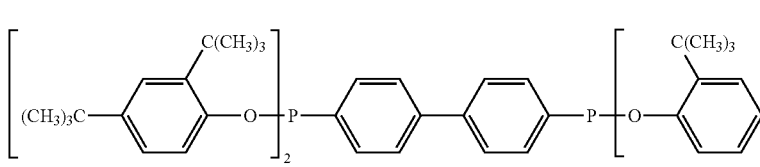
(H)
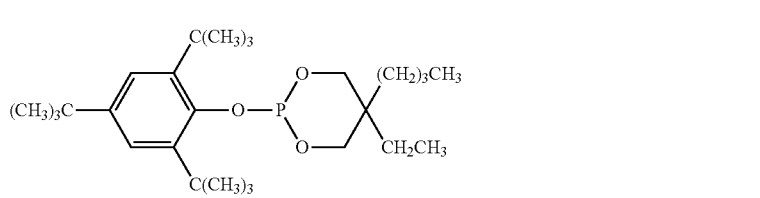
(J)
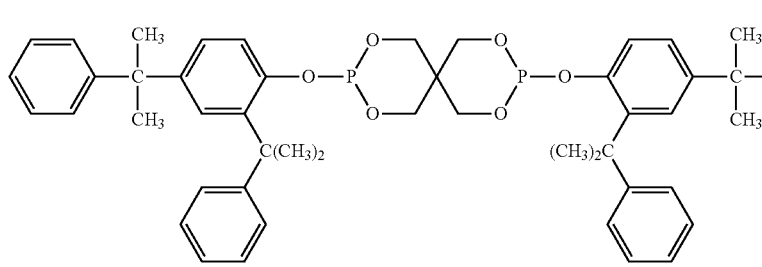
(K)

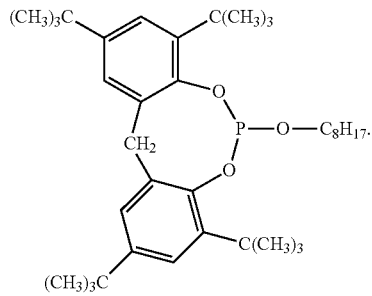

(L)

In certain other embodiments of the present invention, the following compounds are examples of organic phosphites and phosphonites which are suitable for use in the methods of the present invention as organic phosphorus stabilizers: tris (2,4-di-tert-butylphenyl) phosphite, bis(2,4-di-tert-butylphenyl) pentaerythritol diphosphite (formula (D)), tetrakis(2,4-di-tert-butylphenyl)4,4'-biphenylene-diphosphonite (formula (H)), (2,4,6-tri-tert-butylphenyl) 2-butyl-2-ethyl-1,3-propanediol phosphate (formula (J)), or bis(2,4-di-cumylphenyl) pentaerythritol diphosphite (formula (K)).

The organic phosphorus stabilizers are used, for example, in amounts of from about 0.001% to about 50% by weight, about 0.005% to about 20% by weight, about 0.01% to about 5% by weight, 0.05% to about 3% by weight, 0.1% to about 2% by weight or 0.1% to about 1% by weight based on the weight of the polyolefin to be stabilized.

CO-STABILIZERS

In certain embodiments of the present invention, in addition to antioxidants and stabilizers described above the compositions of the present invention may comprise further co-stabilizers (e.g., additives) such as, for example, the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-tert-butyl-4-octadecylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example, 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Esters of β-(3,5-di-tert-butyl-4-hydroxyphenyl)propionic acid, e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard® XL-1, Crompton Corporation).

1.18. Ascorbic Acid (Vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture or mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazin, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. Hindered Amine Stabilizers

As defined herein, "hindered amine stabilizers" are hindered amines which produce nitroxyl radicals that react with alkyl radicals produced during thermo-oxidation of the polymers.

2.1. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidinyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino) ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane and epichlorohydrin, 1,1-bis-(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described in U.S. Pat. No. 5,980,783, the entire contents of which are incorporated herein by reference, that is compounds of component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on columns 64-72 of said U.S. Pat. No. 5,980,783.

The sterically hindered amine may also be one of the compounds described in U.S. Pat. Nos. 6,046,304 and 6,297,299, the entire contents of each of which are incorporated herein by reference, for example compounds as described in claims 10 or 38 or in Examples 1-12 or D-1 to D-5 therein.

2.2. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl) sebacate, bis(1-(2-hydroxy-2-methylpropoxy)-2,2,6,6-tetramethylpiperidin-4-yl) adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl) glutarate and 2,4-bis{N-[1-(2-hydroxy-2-methylpropoxy)-2,2,6,6-tetramethylpiperidin-4-yl]-N-butylamino}-6-(2-hydroxyethylamino)-s-triazine.

3. Ultraviolet Absorbers

As defined herein "ultraviolet absorbers" essentially absorb the harmful UV radiation and dissipate it so that it does not lead to photosensitization i.e., dissipation as heat.

3.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905; 4,853,471; 5,268,450; 5,278,314; 5,280,124; 5,319,091; 5,410,071; 5,436,349; 5,516,914; 5,554,760; 5,563,242; 5,574,166; 5,607,987 and 5,977,219, the entire contents of each of which are incorporated herein by reference, such as 2-(2-hydroxy-5-methylphenyl)-2H-benzotriazole, 2-(3,5-di-tert-butyl-2-hydroxyphenyl)-2H-benzotriazole, 2-(2-hydroxy-5-tert-butylphenyl)-2H-benzotriazole, 2-(2-hydroxy-5-tert-octylphenyl)-2H-benzotriazole, 5-chloro-2-(3,5-di-tert-butyl-2-hydroxyphenyl)-2H-benzotriazole, 5-chloro-2-(3-tert-butyl-2-hydroxy-5-methylphenyl)-2H-benzotriazole, 2-(3-sec-butyl-5-tert-butyl-2-hydroxyphenyl)-2H-benzotriazole, 2-(2-hydroxy-4-octyloxyphenyl)-2H-benzotriazole, 2-(3,5-di-tert-amyl-2-hydroxyphenyl)-2H-benzotriazole, 2-(3,5-bis-α-cumyl-2-hydroxyphenyl)-2H-benzotriazole, 2-(3-tert-butyl-2-hydroxy-5-(2-(ω-hydroxy-octa-(ethyleneoxy)carbonylethyl)-, phenyl)-2H-benzotriazole, 2-(3-dodecyl-2-hydroxy-5-methylphenyl)-2H-benzotriazole, 2-(3-tert-butyl-2-hydroxy-5-(2-octyloxycarbonyl)ethylphenyl)-2H-benzotriazole, dodecylated 2-(2-hydroxy-5-methylphenyl)-2-H-benzotriazole, 2-(3-tert-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-tert-butyl-2-hydroxy-5-(2-methoxycarbonylethyl)phenyl)-5-chloro-2H-benzotriazole, 2-(3-tert-butyl-2-hydroxy-5-(2-methoxycarbonylethyl)phenyl)-2H-benzotriazole, 2-(3-tert-butyl-5-(2-(2-ethylhexyloxy)carbonylethyl)-2-hydroxyphenyl)-2H-benzotriazole, 2-(3-tert-butyl-2-hydroxy-5-(2-isooctyloxycarbonylethyl) phenyl-2H-benzotriazole, 2,2'-methylene-bis(4-tert-octyl-(6-2H-benzotriazol-2-yl)phenol), 2-(2-hydroxy-3-α-cumyl-5-tert-octylphenyl)-2H-benzotriazole, 2-(2-hydroxy-3-tert-octyl-5-α-cumylphenyl)-2H-benzotriazole, 5-fluoro-2-(2-hydroxy-3,5-di-α-cumylphenyl)-2H-benzotriazole, 5-chloro-2-(2-hydroxy-3,5-di-α-cumylphenyl)-2H-benzotriazole, 5-chloro-2-(2-hydroxy-3-α-cumyl-5-tert-octylphenyl)-2H-benzotriazole, 2-(3-tert-butyl-2-hydroxy-5-(2-isooctyloxycarbonylethyl)phenyl)-5-chloro-2H-benzotriazole, 5-trifluoromethyl-2-(2-hydroxy-3-α-cumyl-5-tert-octylphenyl)-2H-benzotriazole, 5-trifluoromethyl-2-(2-hydroxy-5-tert-octylphenyl)-2H-benzotriazole, 5-trifluoromethyl-2-(2-hydroxy-3,5-di-tert-octylphenyl)-2H-benzo-triazole, methyl 3-(5-trifluoromethyl-2H-benzotriazol-2-yl)-5-tert-butyl-4-hydroxyhydrocinnamate, 5-butylsulfonyl-2-(2-hydroxy-3-α-cumyl-5-tert-octylphenyl)-2H-benzotriazole, 5-trifluoromethyl-2-(2-hydroxy-3-α-cumyl-5-tert-butylphenyl)-2H-benzotriazole, 5-trifluoromethyl-2-(2-hydroxy-3,5-di-tert-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-tert-butylphenyl)-2H-benzotriazole and 5-phenylsulfonyl-2-(2-hydroxy-3,5-di-tert-butylphenyl)-2H-benzotriazole.

3.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

3.3. Esters of substituted and unsubstituted benzoic acids, as for example 4-tert-butyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

3.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR 25, (Clariant), dimethyl p-methoxybenzylidenemalonate (CAS#7443-25-6), and Sanduvor® PR 31 (Clariant), di-(1,2,2,6,6-pentamethylpiperidin-4-yl) p-methoxybenzylidenemalonate (CAS #147783-69-5).

3.5. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

3.6. Tris-aryl-o-hydroxyphenyl-s-triazines, for example known commercial tris-aryl-o-hydroxyphenyl-s-triazines and triazines as disclosed in, WO 96/38431, EP 434608, EP 941989, GB 2,317,893, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, the entire contents of each of which are incorporated herein by reference, for example 4,6-bis-(2,4-dimethylphenyl)-2-(2-hydroxy-4-octyloxyphenyl)-s-triazine (Cyasorb® 1164, Cytec Corp.), 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxypethoxy)phenyl]-6-(4-chlorophenyl)-s-triazine, 2,4-bis[2-hydroxy-4-(2-hydroxy-4-(2-hydroxyethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxy-propyloxy)phenyl]-s-triazine, 2,4-bis(2,4-dimethylphenyl)-6-[2-hydroxy-4-(3-benzyloxy-2-hydroxypropyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-□-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxy-phenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)-4,6-bis [2-hydroxy-4-(3-butyloxy-2-hydroxypropyloxy)-phenyl]-s-triazine, 2,4,6-tris[2-hydroxy-4-(3-sec-butyloxy-2-hydroxapropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, Tinuvin® 400, Ciba Specialty Chemicals Corp., 4,6-bis-(2,4-dimethylphenyl)-2-(2-hydroxy-4-(3-(2-ethylhexyloxy)-2-hydroxypropoxy)phenyl)-s-triazine and 4,6-diphenyl-2-(4-hexyloxy-2-hydroxyphenyl)-s-triazine.

4. Metal deactivators, as used herein are compounds which form stable complexes with metal ions and inhibit their reaction with peroxides, for example, N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

5. Peroxide scavengers, for example, esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Hydroxylamines, for example, N,N-dihydrocarbylhydroxylamines selected from the group consisting of N,N-dibenzylhydroxyamine, N,N-dimethyl-hydroxylamine, N,N-diethylhydroxylamine, N,N-bis(2-hydroxypropyl) hydroxylamine, N,N-bis(3-hydroxypropyl)hydroxylamine, N,N-bis(2-carboxyethyl)hydroxylamine, N,N-bis(benzylthiomethyl)hydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine, and N,N-di(hydrogenated tallow) hydroxylamine. The hydroxylamine may be for example the N,N-di(alkyl)hydroxlamine produced by the direct oxidation of N,N-di(hydrogenated tallow)amine. For example, the hydroxylamine prepared by direct hydrogen peroxide oxidation of bis(hydrogenated tallow alkyl) amines, that is N,N-di (hydrogenated tallow)hydroxylamine, CAS# 143925-92-2. N,N-di(hydrogenated tallow)hydroxylamine is prepared as in the working Examples of U.S. Pat. No. 5,013,510 the entire contents of which are incorporated herein by reference.

7. Nitrones, for example, N-benzyl-α-phenyl-nitrone, N-ethyl-α-methyl-nitrone, N-octyl-α-heptyl-nitrone, N-lauryl-α-undecyl-nitrone, N-tetradecyl-α-tridcyl-nitrone, N-hexadecyl-α-pentadecyl-nitrone, N-octadecyl-α-heptadecyl-nitrone, N-hexadecyl-α-heptadecyl-nitrone, N-ocatadecyl-α-pentadecyl-nitrone, N-heptadecyl-α-heptadecyl-nitrone, nitrone derived from N,N-di(hydrogenated tallow) hydroxylamine.

8. Amine-N-oxides, for example Genox™ EP, a di($C_{16}$-$C_{18}$)alkyl methyl amine oxide, CAS#204933-93-7, Crompton Corporation.

9. Benzofuranones and indolinones, for example those disclosed in U.S. Pat. Nos. 4,325,863; 4,338,244; 5,175,312; 5,216,052; 5,252,643; 5,369,159; 5,488,117; 5,356,966; 5,367,008; 5,428,162; 5,428,177; 5,516,920; DE-A-4316611; DE-A-4316622; DE-A-4316876; EP-A-0589839 or EP-A-0591102 the entire contents of each of which are incorporated herein by reference, or 3-[4-(2-acetoxyethoxy) phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

10. Polyhydric alcohols, for example pentaerythritol and glycerol.

11. Basic co-stabilizers, for example, melamine, polyvinylpyrrolidone, dicyandiamide, triallyl cyanurate, urea derivatives, hydrazine derivatives, amines, polyamides and polyurethanes.

12. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate, lithium benzoate, disodium bicycle[2.2.1]heptane 2,3-dicarboxylate; organic phosphates and salts thereof, e.g. sodium 2,2'-methylenebis(4,6-di-tert-butylphenyl)phosphate, and polymeric compounds such as ionic copolymers (ionomers).

13. Clarifiers, for example substituted and unsubstituted bisbenzylidene sorbitols.

14. Fillers and reinforcing agents, for example, calcium carbonate, silicates, glass fibers, glass bulbs, asbestos, talc, wollastonite, nanoclays, kaolin, mica, barium sulfate, metal oxides and hydroxides, carbon black, graphite, wood flour and flours or fibers of other natural products, synthetic fibers.

15. Dispersing Agents, as used herein are compounds which when added to a colloidal solution disperse the particles uniformly, such as, for example, polyethylene oxide waxes or mineral oil.

16. Other additives, for example, plasticizers, lubricants, emulsifiers, pigments, rheology additives, catalysts, flow-control agents, optical brighteners, flame retardants, antistatic agents, antimicrobials and blowing agents.

In certain embodiments of the present invention the co-stabilizers are added, for example, in concentrations of from about 0.0001% to about 50% by weight, about 0.0005% to about 20% by weight, about 0.001% to about 10% by weight, from about 0.01% to about 5% by weight, from about 0.05% to about 1% by weight from about 0.1% to about 1% by weight based on the overall weight of the polyolefin to be stabilized.

In certain other embodiments of the present invention the fillers and reinforcing agents, for example talc, calcium carbonate, mica or kaolin, are added to the polyolefins in concentrations of about 0.001% to about 80% by weight, about 0.005% to about 60% by weight, about 0.01% to about 40% by weight, of about 0.05% to about 20% by weight, of about 0.1% to about 10% by weight, of about 0.5% to about 5% by weight, based on the overall weight of the polyolefins to be stabilized.

In certain particular embodiments of the present invention the fillers and reinforcing agents, for example metal hydroxides, especially aluminum hydroxide or magnesium hydroxide, are added to the polyolefins in concentrations of about 0.001% to about 80% by weight, about 0.005% to about 70% by weight, about 0.01% to about 60% by weight, about 0.1% to about 50% by weight about 0.5% to about 40% by weight about 1% to about 20% by weight based on the overall weight of the polyolefins to be stabilized.

In certain particular embodiments of the present invention carbon black as filler is added to the polyolefins in concentrations, judiciously, of from about 0.001% to about 30% by weight, 0.005% to about 10% by weight, 0.01% to about 5% by weight, of from about 0.05% to about 3% by weight of from about 0.1% to about 2% by weight of from about 0.1% to about 1% by weight based on the overall weight of the polyolefins to be stabilized.

In certain particular embodiments of the present invention glass fibers as reinforcing agents are added to the polyolefins in concentrations, judiciously, of from of about 0.001% to about 80% by weight, about 0.005% to about 60% by weight, about 0.01% to about 40% by weight, of about 0.05% to about 20% by weight, of about 0.1% to about 10% by weight, based on the overall weight of the polyolefins to be stabilized.

The term "alkyl" as used herein means a saturated straight-chain, branched or cyclic hydrocarbon. When straight-chained or branched, an alkyl group is typically C1-C8, more typically C1-C6; when cyclic, an alkyl group is typically C3-C12, more typically C3-C7 alkyl ester. Examples of alkyl groups include methyl, ethyl, n-propyl, iso-propyl, n-butyl, sec-butyl and tert-butyl and 1,1-dimethylhexyl.

The term "alkoxy" as used herein is represented by —OR, wherein R is an alkyl group as defined above.

The term "acyl" as used herein is represented by —C(O)R, wherein R is an alkyl group as defined above.

The term "alkyl ester" as used herein means a group represented by —C(O)OR, where R is an alkyl group as defined above.

The term "aromatic group" used alone or as part of a larger moiety as in "aralkyl", includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-thiazolyl, 5-triazolyl, tetrazolyl, 2-thienyl, 3-thienyl, carbazolyl, 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl. Also included within the scope of the term "heteroaryl", as it is used herein, is a group in which an aromatic ring is fused to one or more non-aromatic rings (carbocyclic or heterocyclic), where the radical or point of attachment is on the aromatic ring.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below.

An "aralkyl group", as used herein is an alkyl groups substituted with an aryl group as defined above.

An optionally substituted aryl group as defined herein may contain one or more substitutable ring atoms, such as carbon or nitrogen ring atoms. Examples of suitable substituents on a substitutable ring carbon atom of an aryl group include —OH, C1-C3 alkyl, C1-C3 haloalkyl, —NO$_2$, C1-C3 alkoxy, C1-C3 haloalkoxy, —CN, —NH$_2$, C1-C3 alkylamino, C1-C3 dialkylamino, —C(O)NH$_2$, —C(O)NH(C1-C3 alkyl), —C(O)(C1-C3 alkyl), —NHC(O)H, —NHC(O)(C1-C3 alkyl), —C(O)N(C1-C3 alkyl)$_2$, —NHC(O)O—(C1-C3 alkyl), —C(O)OH, —C(O)O—(C1-C3 alkyl), —NHC(O)NH$_2$, —NHC(O)NH(C1-C3 alkyl), —NHC(O)N(C1-C3 alkyl)$_2$, —SO$_2$NH$_2$—SO$_2$NH(C1-C3alkyl), —SO$_2$N(C1-C3alkyl)$_2$, NHSO$_2$H or NHSO$_2$(C1-C3 alkyl). Preferred substituents on aryl groups are as defined throughout the specification. In certain embodiments optionally substituted aryl groups are unsubstituted.

Examples of suitable substituents on a substitutable ring nitrogen atom of an aryl group include C1-C3 alkyl, NH$_2$, C1-C3 alkylamino, C1-C3 dialkylamino, —C(O)NH$_2$, —C(O)NH(C1-C3 alkyl), —C(O)(C1-C3 alkyl), —CO$_2$R, —C(O)C(O)R, —C(O)CH$_3$, —C(O)OH, —C(O)O—(C1-C3 alkyl), —SO$_2$NH$_2$—SO$_2$NH(C1-C3alkyl), —SO$_2$N(C1-C3alkyl)$_2$, NHSO$_2$H, NHSO$_2$(C1-C3 alkyl), —C(=S)NH$_2$, —C(=S)NH(C1-C3 alkyl), —C(=S)N(C1-C3 alkyl)$_2$, —C(=NH)—N(H)$_2$, —C(=NH)—NH(C1-C3 alkyl) and —C(=NH)—N(C1-C3 alkyl)$_2$, An optionally substituted alkyl group as defined herein may contain one or more substituents. Examples of suitable substituents for an alkyl group include those listed above for a substitutable carbon of an aryl and the following: =O, =S, =NNHR, =NN(R)$_2$, =NNHC(O)R, =NNHCO$_2$ (alkyl), =NNHSO$_2$ (alkyl), =NR, spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

Without wishing to be bound by any theory or limited to any mechanism it is believed that macromolecule antioxidants and polymeric macromolecular antioxidants of the present invention exploit the differences in activities (ks, equilibrium constant) of, for example, homo- or hetero- type antioxidant moieties. Antioxidant moieties include, for example, hindered phenolic groups, unhindered phenolic groups, aminic groups and thioester groups, etc. of which there can be one or more present in each macromolecular antioxidant molecule. As used herein a homo- type antioxidant macromolecule comprises antioxidant moieties which are all same, for example, hindered phenolic, —OH groups. As used herein a hetero- type antioxidant macromolecule comprises at least one different type of moiety, for example, hindred phenolic and aminic groups in the one macromolecule.

This difference in activities can be the result of, for example, the substitutions on neighboring carbons or the local chemical or physical environment (for example, due to electrochemical or stereochemical factors) which can be due in part to the macromolecular nature of molecules.

In one embodiment of the present invention, a series of macromolecular antioxidant moieties of the present invention with different chemical structures can be represented by W1H, W2H, W3H, . . . to WnH. In one embodiment of the present invention, two types of antioxidant moieties of the present invention can be represented by: W1H and W2H. In certain embodiments W1H and W2H can have rate constants of k1 and k2 respectively. The reactions involving these moieties and peroxyl radicals can be represented as:

(1)

(2)

where ROO, is a peroxyl radical resulting from, for example, initiation steps involving oxidation activity, for example:

 (3)

 (4)

In one particular embodiment of the present invention k1>>k2 in equations (1) and (2). As a result, the reactions would take place in such a way that there is a decrease in concentration of W1. free radicals due their participation in the regeneration of active moiety. W2H in the molecule according equation (5):

 (5) (transfer equilibrium)

This transfer mechanism may take place either in intra- or inter-molecular macromolecules. The transfer mechanism (5) could take place between moieties residing on the same macromolecule (intra- type) or residing on different macromolecules (inter-type).

In certain embodiments of the present invention, the antioxidant properties described immediately above (equation 5) of the macromolecular antioxidants and polymeric macromolecular antioxidants of the present invention result in advantages including, but not limited to:

a) Consumption of free radicals W1. according to equation (5) can result in a decrease of reactions of W1. with hydroperoxides and hydrocarbons (RH).

b) The regeneration of W1H provides extended protection of materials. This is a generous benefit to sacrificial type of antioxidants that are used today. Regeneration of W1H assists in combating the oxidation process. The increase in the concentration of antioxidant moieties W1H (according to equation 5) extends the shelf life of materials.

In certain embodiments of the present invention, the following items are of significant interest for enhanced antioxidant activity in the design of the macromolecular antioxidants and polymeric macromolecular antioxidants of the present invention:
- a) The activity of proposed macromolecular antioxidant is dependent on the regeneration of W1H in equation (5) either through inter- or intra-molecular activities involving homo- or hetero-type antioxidant moieties.
- b) Depending on the rates constants of W1H and W2H it is possible to achieve performance enhancements by many multiples and not just incremental improvements.

In certain embodiments of the present invention, more than two types of antioxidant moieties with different rate constants are used in the methods of the present invention.

In certain embodiments, the present invention pertains to the use of the disclosed compositions to inhibit oxidation in an oxidizable material such as for example a polyolefin.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof. In particular the oxidizable material is a polyolefin, a mixture of polyolefins a substituted polyolefin, (polyacrylates, polymethacrylates) and copolymers of polyolefins as defined above.

The entire teachings of each of the following applications are incorporated herein by reference:

Docket No.: 3805.1000-000; Provisional Patent Application No.: 60/632,893, filed Dec. 3, 2004, Title: Process For The Synthesis Of Polyalkylphenol Antioxidants, by Suizhou Yang, et al;

Docket No.: 3805.1001-000; Provisional Patent Application No.: 60/633,197, filed Dec. 3, 2004, Title: Synthesis Of Sterically Hindered Phenol Based Macromolecular Antioxidants, by Ashish Dhawan, et al.;

Docket No.: 3805.1002-000; Provisional Patent Application No.: 60/633,252, filed Dec. 3, 2004, Title: One Pot Process For Making Polymeric Antioxidants, by Vijayendra Kumar, et al.;

Docket No.: 3805.1003-000; Provisional Patent Application No.: 60/633,196, filed Dec. 3, 2004, Title: Synthesis Of Aniline And Phenol-Based Macromonomers And Corresponding Polymers, by Rajesh Kumar, et al.;

Docket No.: 3805.1004-002; patent application Ser. No.: 11/184,724, filed Jul. 19, 2005 (U.S. Patent Publication No. 2006/0041094 published Feb. 23, 2006), Title: Anti-Oxidant Macromonomers And Polymers And Methods Of Making And Using The Same, by Ashok L. Cholli;

Docket No.: 3805.1004-005; patent application Ser. No. 11/184,716, filed Jul. 19, 2005 (U.S. Patent Publication No. 2006/0041087 published Feb. 23, 2006), Title: Anti-Oxidant Macromonomers And Polymers And Methods Of Making And Using The Same, by Ashok L. Cholli;

Docket No.: 3805.1005-000; Provisional Patent Application No.: 60/655,169, filed Feb. 22, 2005, Title: Nitrogen And Hindered Phenol Containing Dual Functional Macromolecules: Synthesis And Their Antioxidant Performances In Organic Materials, by Rajesh Kumar, et al.

Docket No.: 3805.1006-000; Provisional Patent Application No.: 60/655,169, filed Mar. 25, 2005, Title: Alkylated Macromolecular Antioxidants And Methods Of Making, And Using The Same, by Rajesh Kumar, et al.

Docket No.: 3805.1007-000; Provisional Patent Application No. 60/731,125, filed Oct. 27, 2005, Title: Macromolecular Antioxidants And Polymeric Macromolecular Antioxidants, by Ashok L. Cholli, et al.

Docket No.: 3805.1008-000; Provisional Patent Application No. 60/731,021, filed Oct. 27, 2005, Title:, Title: Macromolecular Antioxidants Based On Sterically Hindered Phenols And Phosphites, by Ashok L. Cholli, et al.

Docket No.: 3805.2006-003; patent application Ser. No.: 11/040,193, filed Jan. 21, 2005 (U.S. Pat. No. 7,323,511 issued Jan. 29, 2008), Title: Post-Coupling Synthetic Approach For Polymeric Antioxidants, by Ashok L. Choll, et al.;

Docket No.: 0813.2006-002; Patent Application No.: PCT/US2005/001948, filed Jan. 21, 2005 (WO 2005/070974 published Aug. 4, 2005), Title: Post-Coupling Synthetic Approach For Polymeric Antioxidants, by Ashok L. Cholli et al.;

Docket No.: 0813.2002-008; Patent Application No.: PCT/US2005/001946, filed Jan. 21, 2005 (WO 2005/071005 published Aug. 4, 2005), Title: Polymeric Antioxidants, by Ashok L. Choll, et al.;

Docket No.: 0813.2002-006; Patent Application No.: PCT/US03/10782, filed Apr. 4, 2003 (WO 2003/087260 published Oct. 23, 2003), Title: Polymeric Antioxidants, by Ashok L. Choll, et al.;

Docket No.: 0813,2002-004; patent application No.: 10/761,933, filed Jan. 21, 2004 (U.S. Pat. No. 7,595,074 published Sep. 29, 2009), Title: Polymeric Antioxidants, by Ashish Dhawan, et al.;

Docket No.: 0813.2002-001; patent application No.: 10/408,679, filed Apr. 4, 2003 (U.S. Pat. No. 7,223,432 issued May 29, 2007), Title: Polymeric Antioxidants, by Ashok L. Choll, et al.;

Tertiary Butoxy Derivatives of Phenol. (Jan Pospisil and Ludek Taimr). (1964), 2 pp. CS 111291

A New Synthesis of aryl tert-butyl Ethers. Masada, Hiromitsu; Oishi, Yutaka. Fac. Eng., Kanazawa Univ., Kanazawa, Japan. Chemistry Letters (1978), (1), 57-8.

Simple Synthesis of the tert-butyl Ether of Phenol. Ol'dekop, Yu. A.; Maier, N. A.; Erdman, A. A.; Shirokii, V. L.; Zubreichuk, Z. P.; Beresnevich, L. B. Inst. Fiz.-Org. Khim., Minsk, USSR. Zhurnal Obshchei Khimii (1980), 50(2), 475-6.

New Method for the Williamson Ether Synthesis Using tert-alkyl Halides in Nonpolar Solvents. Masada, Hiromitsu, Mikuchi, Fumio; Doi, Yasuo; Hayashi, Akira. Dep. Chem. Chem. Eng., Kanazawa Univ., Kanazawa, Japan. Nippon Kagaku Kaishi (1995), (2), 164-6.

New Heterogeneous Williamson Synthesis of Ethers Using tert-alkyl Substrates. Masada, Hiromitsu; Doi, Yasuo; Mikuchi, Fumio; Keiko, Kigoshi. Faculty Eng., Kanazawa Univ., Kanazawa, Japan. Nippon Kagaku Kaishi (1996), (3), 275-82.

Preparation of Aromatic Tertiary Ethers. Tanaka, Masato; Reddy, Nagaveri Prabacal. (Agency of Industrial Sciences and Technology, Japan). Jpn. Kokai Tokkyo Koho (1999), 3 pp. JP 080063.

Preparation of Aromatic Ethers. Watanabe, Makoto; Koie, Yasuyuki. (Tosoh Corp., Japan). Jpn. Kokai Tokkyo Koho (1999), 10 pp. JP 11158103.

o-Alkylated phenols. Firth, Bruce E.; Rosen, Terry J. (UOP Inc., USA). U.S. Pat. No. 4,447,657 (1984), 4 pp.

2-Tert-Butyl-4-alkoxy- and -4-hydroxyphenols. Firth, Bruce E.; Rosen, Terry J. (UOP Inc., USA). U.S. Pat. No. 4,465, 871 (1984), 4 pp.
Conversion of Alkyl Phenyl Ether to Alkylphenol. Klicker, James D. (Borg-Warner Corp., USA). U.S. Pat. No. 4,283, 572 (1981), 3 pp.
O. N. Tsevktov, K. D. Kovenev, Int. J. Chem. Eng. 6 (1966), 328.
Sartori Giovanni, Franca Bigi et al., Chem. Ind. (London), 1985 (22) 762-763.
V. A. Koshchii, Ya.B Kozlikovskii, A. A. Matyusha, Zh. Org. Khim. 24(7), 1988, 1508-1512.
Gokul K. Chandra, M. M. Sharma, Catal. Lett. 19(4), 1993, 309-317.
Sakthivel, Ayyamperumal; Saritha, Nellutla; Selvam, Parasuraman, Catal. Lett. 72(3), 2001, 225-228.
V. Quaschning, J. Deutsch, P. Druska, H. J. Niclas and E. Kemnitz. J. Catal. 177 (1998), p. 164.
S. K. Badamali, S. Sakthivel and P. Selvam. Catal. Today 63 (2000), p. 291.
A. Heidekum, M. A. Hamm and F. Hoelderich, J. Catal. 188 (1999), p. 230.
Y. Kamitori, M. Hojo, R. Matsuda, T. Izumi and S. Tsukamoto. J. Org. Chem. 49 (1984), p. 4165.
E. Armengol, A. Corma, H. Garcia and J. Primo. Appl. Catal. A 149 (1997), p. 411.
J. M. Lalancette, M. J. Fournier and R. Thiffault, Can. J. Chem. 52 (1974), p. 589.
Japanese Patent No. JP 145002980, 1970.
Japanese Patent No. 44028850, 1969.
Japanese Patent No. 44024274, 1969.

EXEMPLIFICATION

Figure 2:
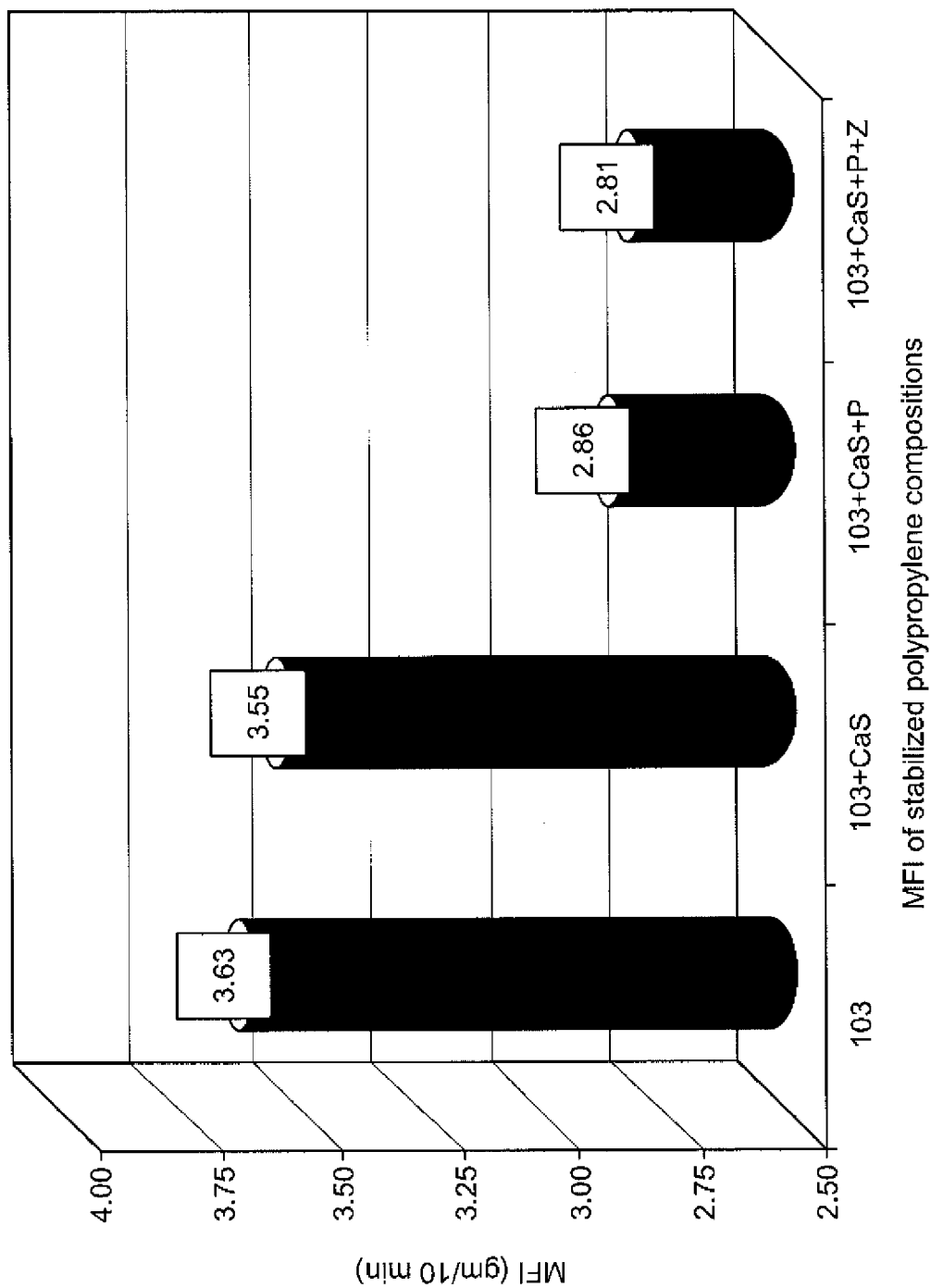
FIG. 2 is a comparison of the Melt flow Index (MFI) of polypropylene in combination with one embodiment of the invention, namely, benzenepropanamide, 3,5-bis(1,1-dimethylethyl)-4-hydroxy-N-(4-hydroxyphenyl); i) alone, ii) in combination with calcium stearate (CasS), iii) in combination with calcium stearate and phosphate (P) and iv) in combination with calcium sulfide, phosphite and zinc oxide (Z).

Polyolefin samples have been stabilized with selective additives described in this disclosure using extrusion methods. These stabilized polyolefins have been tested for their performance using techniques such as melt flow index, gas fading, oxidative induction time (OIT) (FIG. 1) and yellowness index (YI) (FIG. 2).

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising:
a) a polyolefin or a mixture of polyolefins;
b) an antioxidant represented by the following structural formula:

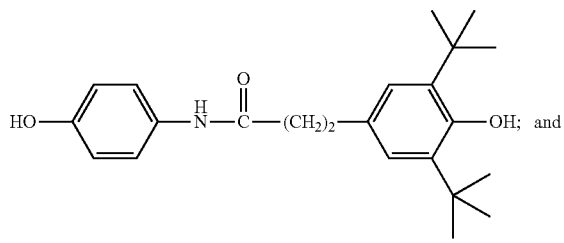

c) at least one additive selected from the group consisting of:
i) a phosphorus stabilizer selected from the group consisting of triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy-pentaerythritol bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis (2,4-di-tert-butylphenyl) 4,4'-biphenylene-diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl) methyl phosphite, bis(2,4-di-tert-butyl-6-methylphenyl) ethyl phosphite, (2,4,6-tri-tert-butylphenyl) 2-butyl-2-ethyl-1,3-propanediol phosphate, bis(2,4-di-cumylphenyl) pentaerythritol diphosphite and a compound represented by the following structural formula:

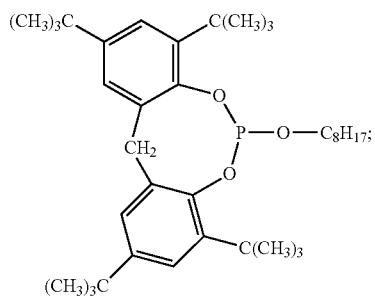

ii) at least one acid stabilizer selected from the group consisting of zinc oxide, calcium lactate, natural and synthetic hydrotalcites, natural and synthetic hydrocalumites, and alkali metal salts and alkaline earth metal salts of higher fatty acids, calcium stearate, zinc stearate, magnesium behenate, magnesium stearate, sodium stearate, sodium ricinoleate and potassium palmitate, antimony pyrocatecholate, zinc pyrocatecholate and combinations thereof; and iii) at least one co-stabilizer selected from the group consisting of an antioxidant, a hindered amine stabilizer, an ultraviolet absorber, a metal deactivator, a peroxide scavenger, a hydroxylamine, a nitrone, an amine-N-oxide, a benzafuranone, an indolinone, a polyhydric alcohol, a basic co-stabilizer, a nucleating agent, a clarifier, a filler, a dispersing agent, a plasticizer, a lubricant, an emulsifier, a pigment, a rheology additive, a catalyst, a flow-control agent, an optical brightener, a flame retardant, an antistatic agent, an antimicrobial and blowing agents.

2. The composition of claim 1 wherein the additive is at least one phosphorus stabilizer selected from the group consisting of tris(2,4-di-tert-butylphenyl) phosphite, bis(2,4-di-tert-butylphenyl) pentaerythritol diphosphite, tetrakis(2,4-di-tert-butylphenyl)4,4'-biphenylene-diphosphonite, (2,4,6-tri-tert-butylphenyl) 2-butyl-2-ethyl-1,3-propanediol phosphate and bis(2,4-di-cumylphenyl) pentaerythritol diphosphite.

3. The composition of claim 2 wherein the antioxidant is in a concentration range from 0.0001% to 10% and the phosphorus stabilizer is in a concentration range 0.01% to 5%.

4. The composition of claim 1 wherein the additive is at least one acid stabilizer selected from the group consisting of zinc oxide, and alkali metal salts and alkaline earth metal salts of higher fatty acids, calcium stearate, zinc stearate, magnesium behenate, magnesium stearate, sodium stearate, sodium ricinoleate and potassium palmitate, antimony pyrocatecholate and zinc pyrocatecholate.

5. The composition of claim 4 wherein the antioxidant is in a concentration range from 0.0001% to 10% and the acid stabilizer is in a concentration range 0.005% to 5%.

6. The composition of claim 1 wherein the additive is at least one phosphorus stabilizer selected from the group consisting of tris(2,4-di-tert-butylphenyl) phosphite, bis(2,4-di-tert-butylphenyl) pentaerythritol diphosphite, tetrakis(2,4-di-tert-butylphenyl)4,4'-biphenylene-diphosphonite, (2,4,6-tri-tert-butylphenyl) 2-butyl-2-ethyl-1,3-propanediol phosphate and bis(2,4-di-cumylphenyl) pentaerythritol diphosphite and an acid stabilizer selected from the group consisting of at least one acid stabilizer selected from the group consisting of zinc oxide, calcium lactate, natural and synthetic hydrotalcites, natural and synthetic hydrocalumites, and alkali metal salts and alkaline earth metal salts of higher fatty acids, calcium stearate, zinc stearate, magnesium behenate, magnesium stearate, sodium stearate, sodium ricinoleate and potassium palmitate, antimony pyrocatecholate and zinc pyrocatecholate.

7. The composition of claim 1, wherein the polyolefin is at least one member selected from the group consisting of polypropylene, polyisobutylene, polybut-1-ene, poly-4-methylpent-1-ene, polyisoprene, polybutadiene, cyclopentene, norbornene, polyethylene, high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polypropylene VLDPE), ultra low density polyethylene (ULDPE), mixture of polypropylene with polyisobutylene, mixtures of polypropylene with polyethylene, ethylene/propylene copolymers, linear low density polyethylene (LLDPE) and mixtures of linear low density polyethylene with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers, polypropylene/ethylene-propylene copolymers, LDPE/ethylene-vinyl acetate copolymers (EVA), LDPE/ethylene-acrylic acid copolymers (EAA), LLDPE/EVA, LLDPE/EAA, ethylene-propylene-diene monomer copolymers (EPDM), copolymers of ethylene with higher alpha-olefins, polybutadiene, polyisoprene, styrene-butadiene copolymers, hydrogenated styrene-butadiene copolymers, styrene-isoprene copolymers, hydrogenated styrene-isoprene copolymers.

8. A method of preventing oxidation comprising combining an oxidizable material with:
   a) an antioxidant represented by the following structural formula:

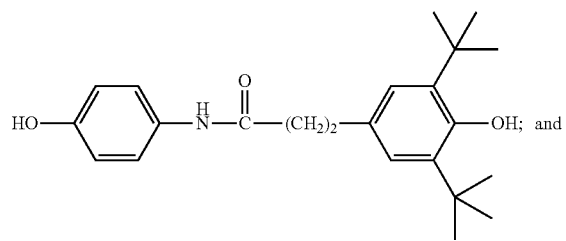

b) at least one additive selected from the group consisting of
      i) at least one phosphorus stabilizer selected from the group consisting of triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy-pentaerythritol disphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis (2,4-di-tert-butylphenyl) 4,4'-biphenylene-diphosphonite, 6-isooctyloxy-2,4,8,10-tetra-tert-butyl-dibenzo[d,f][1,3,2]dioxaphosphepin 6-fluoro-2,4,8,10-tetra-tert-butyl-12-methyl-dibenzo[d,g][1,3,2]dioxaphosphocin, bis(2,4-di-tert-butyl-6-methylphenyl) methyl phosphite, bis(2,4-di-tert-butyl-6-methylphenyl) ethyl phosphite, (2,4,6-tri-tert-butylphenyl) 2-butyl-2-ethyl-1,3-propanediol phosphate, bis(2,4-di-cumylphenyl) pentaerythritol diphosphite and a compound represented by the following structural formula:

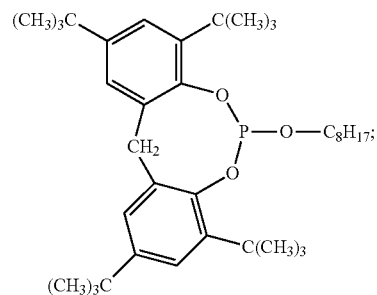

ii) at least one acid stabilizer selected from the group consisting of zinc oxide, calcium lactate, natural and synthetic hydrotalcites, natural and synthetic hydrocalumites, and alkali metal salts and alkaline earth metal salts of higher fatty acids, calcium stearate, zinc stearate, magnesium behenate, magnesium stearate, sodium stearate, sodium ricinoleate and potassium palmitate, antimony pyrocatecholate, zinc pyrocatecholate and combinations thereof; and
      iii) at least one co-stabilizer selected from the group consisting of an antioxidant, a hindered amine stabilizer, an ultraviolet absorber, a metal deactivator, a peroxide scavenger, a hydroxylamine, a nitrone, an amine-N-oxide, a benzafuranone, an indolinone, a polyhydric alcohol, a basic co-stabilizer, a nucleating agent, a clarifier, a filler, a dispersing agent, a plasticizer, a lubricant, an emulsifier, a pigment, a rheology additive, a catalyst, a flow-control agent, an optical brightener, a flame retardant, an antistatic agent, an antimicrobial and blowing agents.

9. A method of preventing oxidation in a polyolefin or a mixture of polyolefins comprising combining the polyolefin or mixture of polyolefins with:
   a) an antioxidant represented by the following structural forumula:

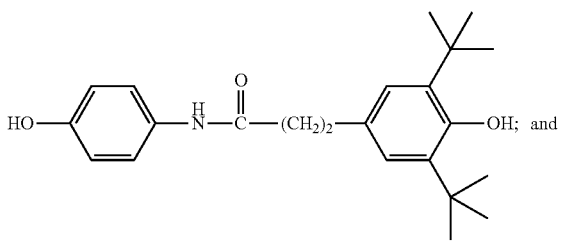

b) at least one additive selected from the group consisting of:
      i) at least one phosphorus stabilizer selected from the group consisting of triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy-pentaerythritol bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis (2,4-di-tert-butylphenyl) 4,4'-biphenylene-diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl) methyl phosphite, bis(2,4-di-tert-butyl-6-methylphenyl) ethyl phosphite, (2,4,6-tri-tert-butylphenyl) 2-butyl-2-ethyl-1,3-propanediol phosphate, bis(2,4-di-cumylphenyl) pentaerythritol diphosphite and a compound repsresented by the following structural formula:

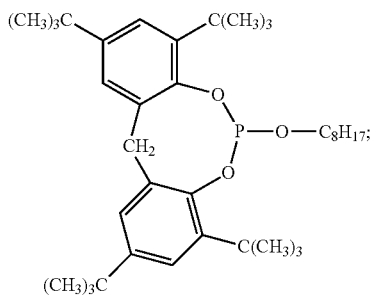

ii) at least one acid stabilizer selected from the group consisting of zinc oxide, calcium lactate, natural and synthetic hydrotalcites, natural and synthetic hydrocalumites, and alkali metal salts and alkaline earth metal salts of higher fatty acids, calcium stearate, zinc stearate, magnesium behenate, magnesium stearate, sodium stearate, sodium ricinoleate and potassium palmitate, antimony pyrocatecholate, zinc pyrocatecholate and combinations thereof; and
      iii) at least one co-stabilizer selected from the group consisting of an antioxidant, a hindered amine stabilizer, an ultraviolet absorber, a metal deactivator, a peroxide scavenger, a hydroxylamine, a nitrone, an amine-N-oxide, a benzafuranone, an indolinone, a polyhydric alcohol, a basic co-stabilizer, a nucleating agent, a clarifier, a filler, a dispersing agent, a plasticizer, a lubricant, an emulsifier, a pigment, a rheology additive, a catalyst, a flow-control agent, an optical brightener, a flame retardant, an antistatic agent, an antimicrobial and blowing agents.

10. The method of claim 9 wherein the additive is at least one phosphorus stabilizer selected from the group consisting of tris(2,4-di-tert-butylphenyl) phosphite, bis(2,4-di-tert-butylphenyl) pentaerythritol diphosphite, tetrakis(2,4-di-tert-butylphenyl)4,4'-biphenylene-diphosphonite, (2,4,6-tri-tert-butylphenyl) 2-butyl-2-ethyl-1,3-propanediol phosphate and bis(2,4-di-cumylphenyl) pentaerythritol diphosphite.

11. The method of claim 10 wherein the antioxidant is in a concentration range from 0.0001% to 10% and the phosphorus stabilizer is in a concentration range 0.01% to 5%.

12. The method of claim 9 wherein the additive is at least one acid stabilizer selected from the group consisting of zinc oxide, and alkali metal salts and alkaline earth metal salts of higher fatty acids, calcium stearate, zinc stearate, magnesium behenate, magnesium stearate, sodium stearate, sodium ricinoleate and potassium palmitate, antimony pyrocatecholate and zinc pyrocatecholate.

13. The method of claim 12 wherein the antioxidant is in a concentration range from 0.0001% to 10% and the acid stabilizer is in a concentration range 0.005% to 5%.

14. The method of claim 9 wherein the additive is at least one phosphorus stabilizer selected from the group consisting of tris(2,4-di-tert-butylphenyl) phosphite, bis(2,4-di-tert-butylphenyl) pentaerythritol diphosphite, tetrakis(2,4-di-tert-butylphenyl)4,4'-biphenylene-diphosphonite, (2,4,6-tri-tert-butylphenyl) 2-butyl-2-ethyl-1,3-propanediol phosphate and bis(2,4-di-cumylphenyl) pentaerythritol diphosphite and an acid stabilizer selected from the group consisting of at least one acid stabilizer selected from the group consisting of zinc oxide, calcium lactate, natural and synthetic hydrotalcites, natural and synthetic hydrocalumites, and alkali metal salts and alkaline earth metal salts of higher fatty acids, calcium stearate, zinc stearate, magnesium behenate, magnesium stearate, sodium stearate, sodium ricinoleate and potassium palmitate, antimony pyrocatecholate and zinc pyrocatecholate.

15. The method of claim 9, wherein the polyolefin is at least one member selected from the group consisting of polypropylene, polyisobutylene, polybut-1-ene, poly-4-methylpent-1-ene, polyisoprene, polybutadiene, cyclopentene, norbornene, polyethylene, high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polypropylene (VLDPE), ultra low density polyethylene (ULDPE), mixture of polypropylene with polyisobutylene, mixtures of polypropylene with polyethylene, ethylene/propylene copolymers, linear low density polyethylene (LLDPE) and mixtures of linear low density polyethylene with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers, polypropylene/ethylene-propylene copolymers, LDPE/ethylene-vinyl acetate copolymers (EVA), LDPE/ethylene-acrylic acid copolymers (EAA), LLDPE/EVA, LLDPE/EAA, ethylene-propylene-diene monomer copolymers (EPDM), copolymers of ethylene with higher alpha-olefins, polybutadiene, polyisoprene, styrene-butadiene copolymers, hydrogenated styrene-butadiene copolymers, styrene-isoprene copolymers, hydrogenated styrene-isoprene copolymers.

16. The composition of claim 2, wherein the additive further includes at least one co-stabilizer selected from the group consisting of a hindered amine stabilizer, an ultraviolet absorber, a metal deactivator, a peroxide scavenger and a hydroxylamine.

17. The composition of claim 4, wherein the additive further includes at least one co-stabilizer selected from the group consisting of a hindered amine stabilizer, an ultraviolet absorber, a metal deactivator, a peroxide scavenger and a hydroxylamine.

18. The composition of claim 6, wherein the additive further includes at least one co-stabilizer selected from the group consisting of a hindered amine stabilizer, an ultraviolet absorber, a metal deactivator, a peroxide scavenger and a hydroxylamine.

19. The method of claim 10, wherein the additive further includes at least one co-stabilizer selected from the group consisting of a hindered amine stabilizer, an ultraviolet absorber, a metal deactivator, a peroxide scavenger and a hydroxylamine.

20. The method of claim 12, wherein the additive further includes at least one co-stabilizer selected from the group consisting of a hindered amine stabilizer, an ultraviolet absorber, a metal deactivator, a peroxide scavenger and a hydroxylamine.

21. The method of claim 14, wherein the additive further includes at least one co-stabilizer selected from the group consisting of a hindered amine stabilizer, an ultraviolet absorber, a metal deactivator, a peroxide scavenger and a hydroxylamine.

* * * * *